US007090648B2

(12) United States Patent
Sackner et al.

(10) Patent No.: US 7,090,648 B2
(45) Date of Patent: Aug. 15, 2006

(54) EXTERNAL ADDITION OF PULSES TO FLUID CHANNELS OF BODY TO RELEASE OR SUPPRESS ENDOTHELIAL MEDIATORS AND TO DETERMINE EFFECTIVENESS OF SUCH INTERVENTION

(75) Inventors: Marvin A. Sackner, Miami Beach, FL (US); D. Michael Inman, Miami, FL (US)

(73) Assignee: Non-Invasive Monitoring Systems, Inc., Miami Beach, FL (US)

( * ) Notice: Subject to any disclaimer, the term of this patent is extended or adjusted under 35 U.S.C. 154(b) by 655 days.

(21) Appl. No.: 09/967,422

(22) Filed: Sep. 28, 2001

(65) Prior Publication Data

US 2002/0103454 A1 Aug. 1, 2002

Related U.S. Application Data

(60) Provisional application No. 60/236,221, filed on Sep. 28, 2000.

(51) Int. Cl.
*A61H 1/00* (2006.01)
(52) U.S. Cl. .............................. 601/1; 601/98; 604/500
(58) Field of Classification Search ................ 600/300; 601/1, 23–24, 89, 98, 100; 604/19
See application file for complete search history.

(56) References Cited

U.S. PATENT DOCUMENTS

| 5,674,262 A | 10/1997 | Tumey ......................... 607/48 |
| 6,155,976 A * | 12/2000 | Sackner et al. ............. 600/300 |
| 6,387,065 B1 | 5/2002 | Tumey ........................ 601/152 |
| 6,620,117 B1 * | 9/2003 | Johnson et al. ............... 601/90 |

OTHER PUBLICATIONS

Crit Care Med. 2001, vol. 29, No. 10, pp. 1983-198, "Regional Blood Flow During Periodic Acceleration", Jose A. Adams, MD et al.
C-Health, Mar. 9, 2000, "Clot Drugs May Kill 1,500 Heart Attack Patients Annually", Daniel Q. Haney.
Vasomedical, Inc., "What is EECP Treatment?" and list of treatment centers, Aug. 30, 2000, from website www.eecp.com.
Vasomedical Inc., Company Description and Background, Aug. 31, 2000, from website www.vasomedical.com.
Vasomedical Inc., A Patient's Guide to Insurance Reimbursement , Aug. 31, 2000, from website www.naturalbypass.com.
Vasomedical Inc., EECP—A Visible Improvement in Angina Treatment, Pamphlet, 1997.
EECP, A Physician's Brief Guide to EECP, Pamphlet.
J. Appl. Physiol. 89: 2447-2452, 2000, "Hemodynamic Effects of Periodic G, acceleration In Meconium Aspiration in Pigs", Jose A. Adams et. al.

Am J Vet Res, vol. 44, No. 10, pp. 1861-1866, Oct. 1983, "Distribution of Blood Flow during Moderate and Strenuous Exercise in Ponies (*Equus caballus*)".
Amer. Phy. Soc., pp. 52-59, 1989, "Blood Pressure Changes During Running in Humans: the "Beat" Phenomenon", Paolo Palatini et al.
Archives of Entironmental Health, pp. 426-432, Oct. 1961, "Vibration Studies", George N. Hoover, Ph.D., et al.
Theoretical, Experimental and Clinical Principles, pp. 420-449 (1998), "McDonald's Blood Flow in Arteries", Wilmer W. Nichols, Ph.D. et al.
Annual Review of Medicine 1997, 48:489-509, "Nitric Oxide Synthase: Role in the Genesis of Vascular Disease", John P. Cooke, MD et al.
Biochimica et. Biophysica Acta 1411 (1999) 273-289, "Nitric Oxide Metabolism and Breakdown", Malte Kelm.
Kidney Int'l., vol. 54, Suppl. 67 (1998), pp. S-100-2-108, "Shear Stress and the Endothelium", Barbara J. Ballermann et al.
Thromb. Haemost 2000; 84: 291-8, "Fluid Shear Stress Increases the Intrea-cellular Storage Pool of Tissue-Type Plasminogen Activator in Intact Human Conduit Vessels", Lena Selin Sjögren et al.
EDRF and Pulsatile Flow, pp. H257-H262, 1991, "Release of Endothelium-derived Relaxing Factor Is Modulated Both By Frequency and Amplitude of Pulsatile Flow", I. R. Hutcheson et al.
Aust. NZ J. Med. 1993; 23; p. 708-710, "The Rhythm of Running: Can the Heart Join In?", O'Rourke et al.
J. Sports Med., 18, 1978, pp. 25-32, "Cardiorespitory Responses to Maximal Treadmill and Bicycle Exercise in Trained and Untrained Subjects", Miharu Miyamura et al.
Circulation, vol. 88, No. 4, Part 1, Oct. 1993, pp. 1456-1462, "Effects of age and Aerobic Capacity on Arterial Stiffness in Healthy Adults", Peter V. Vaitkevicius, MD. et al.
Canadian Journal of Psychology, 1988, 42(2), 163-172, "The Effects of Rocking on the State and Respiration of Normal and Excessive Cryers", M. Ruth Elliott et al.

(Continued)

*Primary Examiner*—Mark Bockelman
(74) *Attorney, Agent, or Firm*—Cohen, Pontani, Lieberman & Pavane

(57) ABSTRACT

Methods of medical treatment and diagnosis using mediators released by endothelial cells stimulated by external addition of pulses to the circulation are disclosed. The external pulses produce circumferential shear stress in body fluid channels that subsequently stimulates the endothelial cells to produce mediators that become available for therapeutic and diagnostic purposes. The preferred means of adding external pulses is the mechanical inducement of periodic acceleration of the body or parts of the body by a reciprocating motion platform.

156 Claims, No Drawings

OTHER PUBLICATIONS

Child Development, pp. 122-128 (1997), "The Influence of Amplitude and Frequency of Vestibular Stimulation on the Activity of Two-Month-Old Infants", David R. Pederson et al.

Brain Research, 816 (1999) 209-219, "Endogenous Nitric Oxide in the Rat Pons Promotes Sleep", B. Hars.

Annals of Biomedical Engineering, vol. 15, pp. 319-329 (1987), "Interaction Between High Frequency Jet Ventilation and Cardiovascular Function", W. Mitzner et al.

Critical Care Medicine, vol. 12, No. 9 (1984), 729-733, "Beat Frequencies in High-Frequency Positive-Pressure Ventilation", Alfred C. Pinchank, Ph.D. et al.

Arch Environ. Health, vol. 11, Sep. 1965, 323-326, "Intravascular Pressure Measurements During Vibration", J. H. Dines, MD et al.

J. Appl. Physiol.: Respirat. Environ. Exercise Physiol. 42(5): pp. 682-689, 1977, "Parameter for Accessing Vibration-Induced Cardiovascular Responses in Awake Dogs", A. Bhattacharya et al.

Hypertension, vol. 26, No. 1, pp. 26-33, Jul. 1995., "Noninvasive Determination of Shear-Rate Distribution Across the Arterial Lumen", Arnold P.G. Hoeks et al.

J. Appl. Physiol.: Respirat. Environ. Exercise Physiol. 47(3): pp. 612-620, 1979, "Modification of Cardiac Function by Synchronized Oscillating Acceleration", A. Bhattacharya et al.

J. American College of Cardiology, vol. 13, No. 7, 1999, pp. 1833-1840, "The Multicenter Study of Enhanced External Counterpulsation (MUST-EECP): Effect of EECP on Exercise-Induced Myocardial Ischemia and Anginal Episodes", Rohit R. Arora, MD, et al.

The American Journal of Cardiology, vol. 84, pp. 950-952, Oct. 15, 1999, "Pneumatic External Counterpulsation: A New Noninvasive Method to Improve Organ Perfusion", Dierk Werner et al.

Circulation, vol. 100, No. 19 (Supplement 1), Nov. 2, 1999, "A Neurohormonal Mechanism for the Effectiveness of Enhanced External Cou9nterpulsation", Giu-Fu Wu et al.

J. of Vascular Surgery, Nov. 2000, pp. 977-987, "An In Vitro Cell Culture System to study the Influence of External Pneumatic Compression on Endothelial Function", Guohao Dai, MS, et al.

J. American College of Cardiology, vol. 37, No. 2, pp. 392-397, 2000, "Endothelial Dysfunction in Patients With Chronic Heart Failure: Systemic Effects of Lower-Limb Exercise Training", Axel Linke, MD et al.

Arterioscler. Thromb. Vasc. Biol.., Dec. 1999, pp. 2835-2840, "Platelet Glycoprotein IIB/IIIa Inhibitors", Alan T. Nurden et al.

Thrombosis Research 93 (1999) pp. 51-59, "Increased Platelet Sensitivity Toward Platelet Inhibitors During Physical Exercise in Patients with Coronary Artery Disease", Stephan Lindemann et al.

Ann. Thorac. Surg. 1997; 64: pp. 1237-1244, "Preoperative Intraaortic Balloon Pump Enhances Cardiac Performance and Improves the Outcome of Redo CABG", Jan T. Christenson, MD et al.

Circulation, vol. 89, No. 1, Jan. 1994, "Arterial Diastolic Pressure Augmentation by Intra-aortic Balloon Counterpulsation Enhances the Onset of Coronary Artery Reperfusion by Thrombolytic Therapy", Paul A. Gurbel, MD et al., pp. 361-365.

American Heart Journal, Jun. 2001, "The Use of Intra-aortic Balloon Counterpulsation in Patients with Cardiogenic Shock Complicating Acute Myocardial Infarction: Data from the National Registry of Myocardial Infarction 2", Hal V. Barron, MD et al., pp. 933-939.

Acta Pharmacol. Toxicol. 1986, vol. 59, Suppl. VI, pp. 79-96, "Digital Pulse Piethysmography (DPG) in Studies of the Hemodynamic Response to Nitrades—A Survey of Recording Methods and Principles of Analysis", Fredrik Lund.

J. of the American College of Cardiology, vol. 34, No. 7, 1999, pp. 2007-2014, "Photoplethysmographic Assessment of Pulse Wave Reflection", Philip J. Chowienczyk, FRCP, et al.

Am. J. Physiol. 251 (Heart Circ. Physiol. 20): pp. H1-H11, 1986, "Pulse-wave Model of Brachial Arterial Pressure Modulation in Aging and Hypertension", Richard S. Chadwick et al.

Circulation, vol. 75, No. 4, Apr. 1987, pp. 711-722, "Arterial Wave Reflection in Heart Failure", Warren K. Laskey, M.D. et al.

Physiologist, 2000, 22.4, p. 282, "Caroid Distension Variations as a Non-Invasive Tool to Examine Cardiac Baroreceptor Function", Kormet et al.

\* cited by examiner

EXTERNAL ADDITION OF PULSES TO FLUID CHANNELS OF BODY TO RELEASE OR SUPPRESS ENDOTHELIAL MEDIATORS AND TO DETERMINE EFFECTIVENESS OF SUCH INTERVENTION

RELATED APPLICATIONS

This application claims priority from U.S. Provisional Patent Application Ser. No. 60/236,221 which was filed on Sep. 28, 2000.

BACKGROUND OF THE INVENTION

1. Field of the Invention

The present invention relates to methods of medical treatment that use an external addition of pulses to body fluid channels in order to stimulate endothelial cells to release beneficial mediators. The circumferential shear stress within body fluid channels caused by these pulses stimulate the endothelial cells to produce mediators that become available for therapeutic and diagnostic purposes.

2. Description of the Related Art

It has become clear that the endothelial inner lining layer of the circulatory system, heart, lymphatics, interstitial spaces and bones of the body play a major role in health and disease through responses to shear stress from circulating fluids flowing across it or pulsating upon it. The recognition that vascular endothelium is a highly active metabolic organ came with the discovery that it actively liberated nitric oxide, a powerful relaxant of vascular smooth muscle as a function of shear stress and pulse frequency across the endothelial surface.

Nitric oxide is synthesized in many cell types by the conversion of L-arginine, a naturally occurring amino acid, to L-citrulline by three distinct nitric oxide synthases (NOSs) enzymes. Sustained high levels of nitric oxide are produced by macrophage or smooth muscle inducible NOS (iNOS) only after induction by certain cytokinines. Both neuronal (nNOS) and endothelial (eNOS) are calcium-dependent and produce low levels of nitric oxide constitutively. eNOS acts in the presence of nicotinamide-adenine-dinucleotide phosphate (NADPH), $Ca^{++2}$/calmodulin and tetrahydrobiopterin to oxidize the L-arginine and form nitric oxide and L-citrulline. Nitric oxide stimulates soluble guanylate cyclase in the underlying vascular smooth muscle that leads to elevation of cyclic guanosine monophosphate (cGMP) with consequent vascular relaxation.

Release of nitric oxide causes endothelium dependent vasodilation. The wrapping of a tourniquet around the upper arm for a few minutes followed by quick removal allows increased blood to flow into the lower arm, a maneuver termed reactive hyperemia; this causes local increase in flow shear stress. Increased pulse frequency acting upon the endothelium is achieved during exercise (also accompanied by increased flow shear stress) or with electrical pacing of the heart.

On the other hand, endothelin-1, a powerful vasoconstrictor substance, is released in higher amounts when shear stress diminishes. Increase of nitric oxide release suppresses endothelin-1. This interplay between these two mediators helps stabilize blood pressure levels. L-arginine, a naturally occurring amino acid, is the substrate for the enzyme in endothelium, eNOS, which converts it to nitric oxide where it acts on smooth muscle and is metabolized into serum nitrite and other NO-compounds within 5 to 10 seconds.

Circulating nitrosylated compounds are agents that take up nitric oxide to a lesser extent and slowly release nitric oxide over prolonged time periods.

Prostacyclin is liberated from endothelium by shear stress and relaxes vascular smooth muscle as an endothelium independent vasodilator. In most blood vessels, the contribution of prostacyclin to endothelial-dependent vasodilation is small and its effect is additive to nitric oxide. However, in terms of preventing platelet aggregation, leukocyte adhesion to endothelium, and susceptibility to thrombosis, the action of prostacyclin and nitric oxide are synergistic. Nitric oxide has an inhibitory effect on prostacyclin production under shear stress but vessel homeostasis is maintained through an increase in prostacyclin production when nitric oxide synthesis is impaired in endothelial cells as in atherosclerosis.

Shear stress independent of perfusion pressure increases gene expression of prostacyclin synthesis-related enzymes cyclooxygenases (COX-1 and COX-2), prostacyclin synthase (PGS), and thromboxane synthase (TXS) and their metabolites prostaglandin (PGI(2)) and thromboxane A(2) (TXA(2)) in endothelium of intact conduit vessels.

In the epicardial coronary arteries, shear stress causes release of endothelial-dependent hyperpolarizing factor (EDHF). Here, its formation plays a much greater role than either nitric oxide or prostacyclin, since in this vascular bed, endothelium-dependent vasodilation is only marginally attenuated by combined inhibition of nitric oxide synthase and cyclooxygenase. In the coronary circulation, EDHF displays the characteristics of a cytochrome P450-dependent arachnoidonic acid metabolite. Ultimately, EDHF acts through the nitric oxide-L-arginine pathway. Sinusoidal pressure oscillations (from 40 to 50 mm Hg, 4 minutes, 1.5 Hz) leads to simultaneous oscillations in the external diameter of isolated coronary artery segments, the amplitude of which were decreased by iberiotoxin and apamin and also by endothelial denudation. Thus, continuous release of EDHF may contribute to the adjustment of an adequate vascular compliance and to the control of coronary blood flow.

Tissue plasminogen activator (t-PA) is released from vascular endothelium through shear stress. Further, shear stress is a potent fluid mechanical stimulus for upregulation of the intracellular storage pool of t-PA in the vascular wall. Shear stress effect is associated with an increased t-PA gene expression. t-PA is measurable in plasma and therefore also is a marker of endothelial function. Muscarinic agents such as acetylcholine and methacholine release tissue plasminogen activator in the forearm circulation of normal subjects. In patients with hypertension, acetylcholine does not change flow and net release and concentration gradients of t-PA, but increases blood flow in normal subjects indicating that vasodilatation by increasing fluid shear stress induces t-PA release with normally functioning vascular endothelium. Marked t-PA release occurs in response to isoproterenol, a beta-adrenergic agonist that acts through the nitric oxide-L-arginine pathway. This effect is independent of the effects of shear stress due to increased blood flow because nitroprusside, an endothelium-independent vasodilator induces similar increases in blood flow without causing t-PA release. Possibly, circumferential shear stress is a more potent stimulus to t-PA release than tangential shear stress.

Elevated intraluminal pressure downregulates t-PA gene and protein expression and inhibits its release from the endothelium independently of shear stress. The defective capacity for stimulated t-PA release that is demonstrable in patients with systemic essential hypertension might thus be an effect of the elevated intraluminal pressure per se.

Activator protein-1 (AP-1) is composed of c-fos/c-jun hererodimers or c-jun/c-jun homodiamers. This is released from the vascular endothelium with shear stress and/or circumferential pulses. The AP-1 transcription factor family is important in the transcription of several genes, e.g., monocyte chemotactic protein-1 (MCP-1) and the vascular cell adhesion molecule-1. Endothelial cells subjected to disturbed laminar shear stress exhibit increased levels of nuclear localized NF-kappaB, Egr-1, c-Jun, and c-Fos, compared with cells exposed to uniform laminar shear stress or maintained under static conditions. In addition, individual cells display a heterogeneity in responsiveness to disturbed flow, as measured by the amount of NF-kappaB, Egr-1, c-Jun, and c-Fos in their nuclei. This differential regulation of transcription factor expression by disturbed versus uniform laminar shear stress indicates that regional differences in blood flow patterns in vivo-in particular, the occurrence of spatial shear stress gradients-may represent important local modulators of endothelial gene expression at anatomic sites predisposed for atherosclerotic development.

Shear stress acts at the apical cell surface to deform cells in the direction of blood flow; wall distention from cycical strain tends to deform cells in all directions. The shear stress response differs, at least partly, from the cyclical strain response, suggesting that cytoskeletal strain alone cannot explain it. Acute shear stress in vitro elicits rapid cytoskeletal remodeling and activates signaling cascades in endothelial cells, with the consequent acute release of nitric oxide, prostacyclin, t-PA and EDHF; activation of transcription factors nuclear factor (NF), kappaB, c-fos, c-jun and SP-1; and transcriptional activation of genes, including ICAM-1, MCP-1, tissue factor, platelet-derived growth factor-B (PDGF-B), transforming growth factor (TGF)-beta1, cyclooxygenase-II, and endothelial nitric oxide synthase (eNOS). Thus, the forces acting upon the vascular endothelium from laminar shear stress and pulsations cause release of a myriad of active agents.

However beneficial the effects of these mediators may be, it is difficult to dose a patient with them. For example, nitric oxide is currently administered as a gas in concentrations from 20 to 80 ppm. Since nitric oxide rapidly combines with hemoglobin competing for oxygenation, it can be considered a toxic gas. Its concentration must be carefully monitored. It undergoes rapid degradation in the pulmonary circulation and has no systemic effects. There are some benefits to inhaled nitric oxide: the pulmonary vascular hypertensive response to acute hypoxia is abolished by NO inhalation therapy. However, the pulmonary hypertensive response to aspirated meconium is only partially reversed by inhaled nitric oxide therapy despite improvements in oxygenation.

Besides inhaled nitric oxide, there are nitric oxide donors. There are substantial differences among the diverse classes of nitric oxide donors including relative importance of nonenzymatic versus enzymatic pathways for NO release, existence of competing metabolic events and the identity of the actual NO-generating enzyme systems. For example, organic nitrates are predominantly venodilators that selectively reduce cardiac preload whereas sodium nitroprusside relaxes arteries and veins equally. The sensitivity of soluble guanylate cyclase to NO donors might be regulated by the ambient concentration of NO, with increased local nitric oxide downregulation of the dilator response to NO donors.

Compounds such as nitroglycerin, nitroprusside and other organic nitrate compounds release nitric oxide through enzymatic degradation and act directly on vascular smooth muscle to cause vasodilation. These compounds are designated endothelium independent vasodilators since they relax vascular smooth muscle even though vascular endothelium may be dysfunctional or destroyed at a given site of action. However, enzymatic conversion may be incomplete at different sites or other vasoactive compounds may be formed leading to different actions on different vascular beds. This may cause drug tolerance, less effectiveness for a given dose of an organic nitrate. Tolerance to continuously administered transdermal nitroglycerin can develop with 48 hours.

Thus, there is a need for a method of providing beneficial mediators (such as nitric oxide, prostacyclin, endothelial dependent hyperpolarizing factor (EDHF), and tissue plasminogen activator (t-PA)) that are released by the endothelium, in order to aid in the treatment and diagnosis of various diseases, conditions, and injuries. Furthermore, the method must avoid the dosing problems of previous treatments.

SUMMARY OF THE INVENTION

In the present invention, a method of medical treatment is provided in which the external addition of pulses to the circulation of a patient stimulates the release of beneficial mediators. The beneficial mediators include nitric oxide, prostacyclin, tissue plasminogen activator (t-PA), endothelium derived hyperpolarizing factor, endothelial derived relaxing factor, endothelial growth factors and transcription genes. The application of external pulses according to the present invention also provides for the substantial suppression of endothelins, tissue plasminogen antigens, tissue plasminogen inhibitor, as well as modulation of vascular endothelial growth factor. In addition, he application of external pulses according to the present invention provides for the increased expression of Cu/Zn superoxide dismutase; the increased gene expression of prostacyclin synthesis-related enzymes cyclooxygenases (COX-1 and COX-2), prostacyclin synthase (PGS), and thromboxane synthase (TXS); and the increased expression of metabolites prostaglandin (PGI(2) and thromboxane A(2) (TXA(2)) in endothelial cells.

The method of medical treatment according to the present invention also regulates the endothelial release of beneficial mediators by repeatedly providing external pulses to the body's fluid filled channels such that even during periods when external addition of pulses is not being applied, bioavailability of the beneficial mediators is greater than in the pretreatment period.

The method of medical treatment according to the present invention further includes dosing the patient with a drug. The combination of dosing and providing external pulses can potentiate an effect of the drug, limit the dosing of the drug, minimize unwanted side effects, and obtain unique beneficial effects.

In the present invention, a method of medical diagnosis is provided in which external pulses are applied to the patient, thus stimulating the endothelium, and the patient's response is tested.

In the preferred embodiment, the external pulses are applied with a frequency between about 1 and 6 Hz and with a periodic acceleration up to about ±0.6 g by a reciprocating movement platform for shifting the patient to and fro in headwards-footwards direction using a horizontal platform driven by a controllable fly wheel-motor mechanism.

The various features of novelty which characterize the invention are pointed out with particularity in the claims annexed to and forming a part of the disclosure. For a better understanding of the invention, its operating advantages, and specific objects attained by its use, reference should be had to the descriptive matter in which there are illustrated and described preferred embodiments of the invention.

DETAILED DESCRIPTION OF THE PRESENTLY PREFERRED EMBODIMENT

In the methods of medical treatment and diagnosis according to the present invention, a means for externally and non-invasively adding external pulses into the body's fluid filled channels stimulates endothelial release of beneficial mediators by providing pulses to these channels over the body's own pulse.

More exactly, external addition of vascular pulses to the circulation causes release of nitric oxide, tissue plasminogen activator, prostacycline, and endothelial hyperpolarizing factor and other mediators through increased circumferential shear stress to the endothelium. Upregulation of the enzymes responsible for release of such mediators is a function of tangential shear stress to the endothelium, e.g., increased blood flow as in exercise, or circumferential shear stress, e.g., increased pulse rate during exercise. Vascular pulses and/or increased overall blood flow are the major means for release of nitric oxide from endothelium and are not dependent on localized reactions in different size vessels of donors such as nitroglycerin. The latter is ineffective in small arterioles whereas nitroprusside, another donor, is effective in all size vessels. Externally added pulses to the circulation that cause release of nitric oxide do not produce paradoxical vasoconstriction as with acetylcholine in coronary vessels where presumably acetycholine is able to penetrate dysfunctional endothelium and reach smooth muscle without acting or minimally acting through a nitric oxide-L-arginine pathway.

A blood vessel is exposed to two main stress components: 1) circumferential stress due to pulsatile blood pressure and/or flow, and, 2) shear stress, the tangential stress exerted by the flowing blood on the endothelium. Endothelial cells can distinguish between these stresses. Small, pulsatile circumferential stresses up to 10 Hz enhance release of beneficial mediators such as nitric oxide and prostacyclin, vasodilator mediators and tissue plasminogen activator, a fibrinolytic mediator, among others whereas large pulsatile blood pressure changes promote production of endothelin-1, a vasoconstrictor mediator, and tissue plasminogen inhibitor among others. Small pulsations >10 Hz do not enhance nitric oxide release and may promote endothelin-1 release. In isolated vessel preparations, peak endothelial release of nitric oxide occurs at small pulsations between 4 and 6 Hz. Tangential stress due to increased blood flow enhance release of nitric oxide, prostacyclin, and tissue plasminogen activator. The arterial response to flow is highly dependent on the mode of flow. Vasodilation induced by initiating pulsatile flow or increasing either pulse amplitude or frequency appears to be mediated by augmented nitric oxide release as result of shear stress-induced deformation of the endothelial cells.

Pulsatile and non-pulsatile blood flow have been compared in anesthetized dogs at the same mean flow rate with pulsatility set to 2 Hz. Lower blood pressure and systemic vascular resistance are achieved with pulsatile than non-pulsatile blood flow. The repayment flow and the duration are significantly larger in pulsatile flow than non-pulsatile blood flow. Plasma nitrite/nitrate was 16.2 mmmol/l in pulsatile flow and 13.9 mmmol/l in nonpulsatile flow at the same mean flow rate. Thus, pulsatile blood flow causes greater nitric oxide release from endothelium than non-pulsatile blood flow at the same mean rate.

As was discussed above, shear stress causes release of nitric oxide, prostacyclin, t-PA and EDHF; activation of transcription factors nuclear factor (NF), kappaB, c-fos, c-jun and SP-1; and transcriptional activation of genes, including ICAM-1, MCP-1, tissue factor, platelet11 derived growth factor-B (PDGF-B), transforming growth factor (TGF)-betal, cyclooxygenase-II, and endothelial nitric oxide synthase (eNOS). Thus, the result of external pulses upon the vascular endothelium from shear stress is the release of a myriad of active agents.

As an example of the benefits of the methods according to the present invention, consider previous methods of providing nitric oxide. With inhaled nitric oxide, the pulmonary hypertensive response to aspirated meconium is only partially reversed; however, the pulmonary hypertensive response to experimental meconium aspiration syndrome is completely abolished by nitric oxide liberated from endothelium using externally added pulses to the circulation with a horizontal motion platform that produces pGz. With nitric oxide donors, there are the problems of drug tolerance and less effectiveness for a given dose of an organic nitrate. As noted above, tolerance to continuously administered transdermal nitroglycerin can develop with 48 hours; however, external addition of pulses to the circulation causing release of nitric oxide from endothelium is not associated with drug tolerance.

The following description of the preferred embodiments is broken down into 5 sections:

I. The Means for Adding External Pulses
II. Treatments using Mediators produced by External Pulses
III. Treatments using Combinations of Drugs or Devices and Mediators produced by External Pulses
IV. Testing Efficacy of Treatments
V. Diagnoses using Mediators produced by External Pulses I. The Means for Adding External Pulses In the preferred embodiment, the external pulses are applied with a frequency between about 1 and 6 Hz and with a periodic acceleration up to about ±0.6 g by a reciprocating movement platform for shifting the patient to and fro in headwards-footwards direction using a horizontal platform driven by a controllable fly wheel-motor mechanism.

An example of a means for adding external pulses according to the preferred embodiment is a motion platform that imparts periodic acceleration (pGz) forces to the body non-invasively, as described in U.S. Pat. No. 6,155,976 to Sackner et al., which is hereby incorporated by reference. A study that was published in *J. Appl. Physiol* 2000; 89:2447–2452 by Adams et al., Hemodynamic effects of periodic G(z) acceleration in meconium aspiration in pigs, used a similar motion platform to ventilate anesthetized paralyzed piglets. It also produced pulmonary vasodilatation during pulmonary hypertension induced with tracheal instillation of meconium. The hypothesis that pGz causes systemic vasodilatation was tested (Adams et al., Regional blood flow during periodic Gz accleration, Critical Care Medicine, October 2001. Juvenile pigs were anesthetized and paralyzed and placed on a motion platform that oscillated at a frequency of 4 Hz and a force of ~0.4 G. A prominent feature of periodic acceleration is the generation of machine-induced pulsations of pressures and flows within the cardiovascular system that are superimposed onto the endogenous pressures and flows induced by the heartbeat. These pulsations occur at the frequency and amplitude of the motion platform and interact with those induced by the heartbeat producing periodic summing and cancellations of the two signals. The amplitude of the induced pulsations on the systemic blood pressure trace ranged from 5 to 50 mm Hg. In addition to the individual pressure and flow waveforms produced by the motion platform and the heartbeat of the animal, a third waveform of lower frequency is evident. These lower frequency waveforms are termed beat frequency events and are the arithmetic differences between the frequency of the motion platform events and those induced by the natural heartbeat.

Regional blood flows, as assessed by colored microspheres, were increased by pGz, relative to values obtained before pGz. Blood flow (ml/min/100 g) significantly increased to the epicardium (71%), endocardium (93%), cerebrum (183%), brain stem (177%), renal cortex (53%), ileal mucosa (69%), gastric antral mucosa (72%), and liver (86%). The blood flows returned to baseline 10 min after discontinuation of pGz, except in the myocardial layers where blood flow remained significantly elevated. There was no difference compared to baseline in heart rate, arterial blood gases and blood pressure, but serum nitrite concentration was significantly higher (58%) during pGz. In a second series of animals, pGz increased pulmonary artery blood flow directly proportional to the magnitude of the applied acceleration force with frequency held constant. The increased organ blood flow caused by vasodilation by stimulation of endothelium from added pulses, thus causing increased circumferential shear stress as well as increased tangential shear stress from increased cardia output both of which promoted release of nitric oxide and prostacyclin from endothelium.

The means for adding external pulses according to the preferred embodiment will be discussed in more detail below, but first, other means of adding external pulses will be described.

Locomotion

Locomotion such as jogging running, jumping and skiing introduce additional pulses into the circulation with each contact of the feet to the ground as long as sufficient acceleration intensity is imparted to the body because of that activity.

In contrast to pGz that preferentially distributes blood flow to organs and not to skeletal muscle, the opposite with exception of cardiac myocardium takes place during aerobic exercise. Blood flow to the brain, heart, kidneys, diaphragm, and skeletal muscles was studied at rest and during graded treadmill exercise, using radionuclide-labeled microspheres (15 microns diameter), in healthy adult ponies. Hemodynamic changes brought about by exercise included marked increases in cardiac output, mean aortic pressure, left ventricular end-diastolic pressure, and right ventricular systolic and end-diastolic pressures. Blood flow to the brain stem and cerebral hemispheres was unchanged during both moderate exercise (heart rate=154+/−3 beats/min) and severe exercise (heart rate=225+/−7 beats/min). Despite marked hypocapnia during severe exercise, cerebellar blood flow increased by 32% above control value. Myocardial blood flow increased transmurally with both levels of exercise. The endo:epi (inner:outer) perfusion ratio for the left ventricle and the interventricular septum decreased during exercise. It did not differ from unity. During intense exercise, renal blood flow decreased to 19% of its control value. Blood flow to the diaphragm exceeded that to the skeletal muscles during both intensities of exercise. Blood flow to the exercising muscles of the brachium and thigh increased by 31- to 38-fold during moderate exercise and by 70- to 76-fold during severe exercise. Thus, the cardiovascular response to strenuous exercise in the pony included a modest increase in blood flow to the cerebellum, no change in brain stem and cerebral blood flow and a major increase of blood flow to the myocardium, diaphragm, and exercising skeletal muscles, while blood flow was diverted away from the kidneys. The pony's cardiovascular response to severe exercise is similar to that of humans.

In Palatini.P.et al's (J. Appl. Physiol.1989;67:52–59) study of trained runners, stride frequency varied from subject to subject, but in every athlete it was related to running velocity. During warm-up, it ranged from 130–165/min, during submaximal speed, from 140–175/min, and during sprinting from 165–205/min. Intra-arterial pressure recordings showed beat frequency from the additional pulses introduced by running. Although not cited in this study, the beat frequency phenomenon depicted was similar to tracings published by Hoover,G. N.; Ashe,W. F.; Dines, J. H.; Fraser, T. M. (Arch. Environ. Health; 1961;3:426–432) using a horizontal shake table in anesthetized dogs. In another study by the Palatini group, both running on a track and cycling on a bicycle to exhaustion were performed in a crossover fashion. Beat frequency as measured with intraarterial blood pressure monitoring was observed in 23 of 25 subjects during running. The source of the stride-dependent wave was identified as shaking of the aorta and the great vessels during the running. The beat frequency pattern was never observed during bicycle exercise, where heart rates comparable to running were attained. In running, the amplitude of blood pressure swings during the runs varied from ±10 to ±62 mm Hg and their frequency equaled the runner's stride. Of interest is the study by Adams et al. Regional Blood Flow during Periodic Gz Acceleration, Critical Care Medicine, October 2001, submitted for publication, in which beat frequency was observed in anesthetized piglets with pGz generated by a motion platform. Here, the amplitude of blood pressure swings was similar to the runners, from 5 to 50 mm Hg.

Nichols W M, O'Rourke M. (McDonald's Blood Flow in Arteries: Theoretical, experimental and clinical principles, vol. 9, 4th Ed. New York: Oxford University Press; 1998. p. 421–449) noted that during exercise stress tests, arterial pressure is usually measured by sphygomomanometry using an upper arm cuff. Consistent values are routinely presented in stress test reports for treadmill exercise. But when pressure waves are measured with a catheter, or non-invasively with tonometry of Finapress, marked fluctuations are usually very obvious. Although these waves have been passed over as motion artifact, careful studies indicate that the waves are real events. Such studies cast doubt on the confidence with which blood pressure is conventionally recorded during exercise. Body movement during running and treadmill exercise generates arterial pressure waves. These are minute when body posture remains constant as with cycling, but the waves are of high amplitude—similar to those generated by ventricular ejection itself—when the body moves vertically when running on a treadmill or pathway. With running, at the peak of exercise, the arterial pressure waves caused by bodily movements can be clearly seen. In a depicted example, these waves were about 75% of the natural pulse pressure. At the peak of exercise, stride rate and heart rate are often very close (at ~140–180 per minute) and the pulse pressure rhythmically increases and decreases at a frequency of 1 to 10 beats/minute, as determined by difference in heart rate and stride rate (beat frequency phenomenon). Thus, sphygomomanometry would be inaccurate such exercising conditions.

O'Rourke M et al. (The rhythm of running: can the heart join in? Aust. N. Z. J. Med. 1993;23:708–10) studied 20 young men with ECG and Finapress finger blood pressure recordings during running that increased heart rate from 69 b/m at rest to 184 b/m. Uphead head movement of ~8 to 12 cm was noted for every subject while running. Beat frequency was observed and various patterns were seen in the Finapress recordings. A biphasic pressure waveform was seen when the pulse pressure was the lowest, similar to that generated during therapeutic counterpulsation. When the pulse pressure was the highest, a monophasic wave of high pulse pressure was similar during inappropriately timed counterpulsation. Modelling studies suggest that entrainment with optimal timing, e.g., low pulse pressure with biphasic wave, would favor cardiac performance during exercise and easily give an edge to an athlete because of reduction of left ventricular afterload, increase in coronary perfusion pressure, and modest increase in cardiac output. The authors further stated that such counterpulsation during running depending upon timing to the primary pulse wave has the potential to enhance or hinder athletic performance. However, theses authors a did not recognize that the added pulsations with running would upregulate eNOS in vascular endothelium to increase nitric oxide levels thereby promoting vasodilation.

The blood pressure during running in trained runners is lower than the blood pressure in trained cyclists during cycling. The higher blood pressure in cyclists is associated with lower maximum oxygen consumption than runners during their designated sport activity. Miyamura M,et al. (Cardiorespiratory responses to maximal treadmill and bicycle exercise in trained and untrained subjects. J. Sports Med. Phys. Fitness 1978;18:25–32) compared in 9 untrained and 11 trained subjects, the cardiorespiratory responses to maximal treadmill amd cycling exercise. Maximum oxygen consumption was higher in treadmill than cycling exercise in both groups (p<0.005). Cardiac output and heart rate and calf blood flow were also higher in running than cycling. These differences between cycling and running might relate to increased levels of nitric oxide as a result of the "counterpulsation" mechanism associated with running, information not known to the authors at that time This would lead to greater vasodilation or lessened stiffness of muscular arteries. This theory is supported by the observations that higher physical conditioning status, indexed by maximum oxygen consumption is associated with reduced arterial stiffness, both within a predominantly sedentary population and in endurance trained older men relative to their less active age peers. External addition of pulses to the circulation in a sedentary subject differs from running in that cardiac output rises only about 20–30% whereas running to exhaustion causes a rise of about 500% above baseline. Further the former is associated with preferential distribution of blood flow to the brain, heart and viscera whereas the latter with preferential blood flow to skeletal muscle.

Nitric Oxide

Exercise training improves endothelium-dependent vasodilatation both in epicardial coronary vessels and in resistance vessels in patients with atherosclerosis, coronary artery disease or chronic heart failure. Increased release of nitric oxide through continued physical exercise alleviates impairment of reactive hyperemia in patients with essential hypertension.

Basal release of endothelium-derived NO is increased with four weeks of home based training in hypercholesterolemic patients, independently of lipid profile modification. This -upregulation of eNOS contributes to the cardiovascular protective effects of exercise training including reduction of blood pressure.

Tissue Plasminogen Activator (t-PA) & Other Fibrinolytic Parameters

In normal subjects, strenuous supine cycling exercise elevates t-PA seven fold above baseline. Single acute bouts of dynamic exercise transiently increase t-PA and decrease tissue plasminogen inhibitor activity without affecting plasma fibrinogen concentration in healthy young men. Intensive exercise training enhances resting t-PA activity and reduces fibrinogen and PAI-1 activity in older men. These effects are potential mechanisms by which habitual physical activity might reduce the risk of cardiovascular disease.

Rocking Babies in Carriage or Bed

Adams et al. (unpublished observations) found that mothers push the baby carriage back and forth to sooth their babies at rates between 45 and 90 times per minute. In babies that are not crying, this motion produces pGz as measured on the top of the baby's cranium of about ±0.15 to ±0.25 g. In colicky babies who have prolonged loud crying, pGz may reach as high as ±0.9 g at rates of about 90 times per minute. These values are consistent with reports in the literature. In one study, a baby carriage with wheels driven back and forth on a wooden platform by a wooden rod connected to a motor moved the carriage at a rate of 40 or 57 times a minute. The rocking distance was 13 cm while the infant was on its back. Duration of study for rocking and non-rocking was four minutes each. Infants cried less and had less variable respiration (measured with strain gauge around abdomen) during rocking than non-rocking. In another study, in which vertical rocking was employed, viz., baby flat on its back in an aluminum bassinet with the undercarriage containing a drive mechanism, the vertical amplitude ranged between two to five inches at 30 to 90 times per minute. Observers rated the effectiveness of rocking every 15 seconds as to state, i.e., 1) quiet sleep, 2) awake or asleep with slight activity, 3) awake and active, 4) awake with restless activity, 5) upset and irritable, and 6) extremely agitated. The readings were averaged for the baseline and 5 minute consecutive periods of rocking. The lower the value of the observers' readings, the more effective the rocking. In general, readings were lower as a function of higher frequencies and larger displacements of rocking. This observer's values inversely correlated to the peak acceleration. For example, the lowest observer mean, ~1.0, was found with a frequency of 60 times per minute and displacement of 5 inches. This produced pGx of ~±0.25. The highest Gx, ~±0.28, was found for frequency of 70 times per minute and displacement of 4 inches. pGx of ±0.25 g would be expected to cause nitric oxide release nitric oxide release from vascular endothelium. Since nitric oxide modulates sleep in experimental animals and promotes NREM sleep in sleep deprivation, this may account for the beneficial effects of rocking in this study.

External addition of pulses to the circulation up to and exceeding ±0.25 g in babies and possibly adults might serve as an aid to sleep owing to the release of nitric oxide.

High Frequency Ventilation

Types

Modes of ventilation are characterized by positive pressure breathing at higher rates and lower volumes than natural breathing. Their basis is in the notion that smaller tidal volumes than those of conventional mechanical ventilation cause less barotrauma to the lungs. Techniques include among others: 1) high frequency positive ventilation (HFPPV) achieved by modifying a conventional ventilator to achieve higher rates (1.3 to 3.3 Hz) and lower tidal volumes, 2) high frequency ventilation superimposed upon conventional mechanical ventilation 3) high frequency jet ventilation (HFJV) in which gas is distributed to the trachea as a jet from a catheter at a volume less than the anatomical dead space of the ventilated subject at rates of 1 to 3.3 Hz; and 4) high frequency oscillatory ventilation (HFOV) at rates of 5 to 20 Hz in which gas is oscillated into the lungs at a volume less than the anatomic dead space from a piston pump or loud speaker with a bias flow of gas to remove accumulated carbon dioxide. The first three methods rely on passive expiration and the ratio of inspiratory/expiratory times is adjustable. HFOV provides active inspiratory and expiratory phases whose timing can also be adjusted. The shorter the expiratory phase, the more likely the development of auto-PEEP or gas trapping leading to unwanted, uncontrolled pulmonary hyperinflation. These ventilatory methods have been reported as causing beat frequencies, a phenomenon in dynamic systems where two or more oscillating frequencies or their harmonics are nearly equal in value, marking presence of externally added pulses. Therefore, ventilatory addition of pulses to the circulation have potential to stimulate endothelium to release beneficial mediators.

High Frequency Positive Pressure Ventilation

Amplitude modulation of the waveforms of several cardiovascular variables was investigated during high-frequency (1.3 to 3.3 Hz) positive-pressure ventilation (HF-PPV). The amplitude modulation of the pulmonary artery pressure wave was most prominent and its beat frequency (BF) was equal to the difference between the heart rate and the ventilation rate. No obvious pulses apart from the findamental arterial pulse appeared on the analog traces. Spectral analysis of the pulmonary artery pressure demonstrated well-defined peaks associated with the BF. No significant physiologic changes in either cardiovascular or pulmonary function were attributable to the beat phenomenon. Thus, pulses externally added to the circulation by high frequency positive ventilation are too small in amplitude to significantly stimulate vascular endothelium release of nitric oxide.

High Frequency Ventilation Superimposed on Conventional Mechanical Ventilation In experimental pulmonary hypertension induced by infusion of thrombin, high frequency volumes at 5, 15, and 20 Hz were superimposed on a slowed rate of ventilation generated by conventional mechanical ventilation. This was done to keep minute ventilation constant. This mode of adding pulses to the circulation did not change the elevated pulmonary vascular resistance that was 2× its baseline value. Thus, pulses externally added to the circulation by this means are too small in amplitude to significantly stimulate vascular endothelium to release nitric oxide.

High Frequency Jet Ventilation

During high frequency jet ventilation in normal dogs, all intrathoracic blood pressures, pulmonary artery, aorta, right and left atrium as well as systemic blood pressure show beat frequency. This is due to transmission of changes in pleural pressures to the vascular structures as evidenced by marked diminution when the chest is opened. Pleural pressure swings during high frequency jet ventilation (HFJV) in this study were about ±1.3 mm Hg. When pleural pressure swings were much lower than pulmonary arterial pressure swings, beat frequency amplitude was diminished as compared to when they were more equivalent. HFJV addition of pulses to the circulation is of insufficient amplitude to significantly release mediators from vascular endothelium. Despite beat frequency of the pressure pulses, the amplitude is only a few mm Hg and the added pulses cannot be seen on the systemic or pulmonary arterial pressure waveforms. In experimental pulmonary hypertension induced with microemboli, HFJV synchronized to any part of the cardiac cycle did not change pulmonary arterial pressure or pulmonary vascular resistance.

High Frequency Oscillatory Ventilation

Ventilation with HFOV at 10 Hz compared to conventional mechanical ventilation caused pulmonary arterial pressure and pulmonary arterial resistance to rise in both normoxic and hypoxic conditions. Hypoxia itself elevated both pulmonary arterial pressure and pulmonary arterial resistance. The basis for the pulmonary vasoconstrictive effect of HFOV is not due to release of vasoconstrictive prostaglandins. It is possible that pulses added to circulation at 10 Hz from HFOV caused release of endothelin-1 from endothelium, a known pulmonary vasoconstrictor mediator. In this regard, addition of pulses in perfused isolated vessels at different frequencies revealed that greatest vasorelaxant effect was present between 4.2–6 Hz; pulses at 10 Hz did not cause any vasorelaxation compared to baseline (Hutcheson, I. R, Griffith, T. M. J. Appl. Physiol 1991;261:H257–H262). HFOV between 4–6 Hz might cause vasorelaxation but the beat frequency amplitude is only a few mm Hg and the added pulses cannot be seen on the systemic or pulmonary arterial pressure waveforms.

Potential to Add Pulses to Circulation that Stimulate Mediator Release

The addition of pulses to the circulation by the current modes of high frequency ventilation do not produce pulses of sufficient amplitude to cause significant release of mediators from vascular endothelium. High frequency oscillatory ventilation utilizing much higher pressures than currently employed for ventilatory means has the best potential for adding pulses without causing unacceptable gas trapping since this factor can be controlled by a bias flow mechanism. In order for this modality to generate added pulses of sufficient amplitude to stimulate endothelium for mediator release, much higher pressures need to be utilized than currently employed for ventilation. In this application, an apparatus dead space must be interposed between the HFOV device and the airway to prevent unacceptable hyperventilation.

Cardiac Pacing

Cardiac pacing, e.g., baseline 89 beats/min to 195 beats/min, in intact dogs instrumented with piezoelectric crystals to measure epicardial coronary vessel diameter increased diameter but not after treatment with the eNOS inhibitor, L-NAME. Therefore, vasodilation for this vascular bed is mediated through a nitric oxide-L-arginine pathway. Coronary arterial diameter increased when blood flow increased with pulse held constant in the presence of LNAME. The latter is due to release of Endothelial Dependent Hyperpolarizing Factor (EDHF), a molecule released by shear stress of epicardial coronary vessels that ultimately relaxes vascular smooth muscle through the nitric oxide-L-Arginine pathway.

Horizontal Shake Table

Hoover, G. N.; Ashe, W. F.; Dines, J. H.; Fraser, T. M. (Arch. Environ. Health; 1961;3:426–432) using a horizontal shake table in anesthetized dogs observed beat frequencies between 2.5–5 Hz. A beat frequency is the difference between two added frequencies and is most predominant when these frequencies are close together. At a beat frequency of 6 Hz, a secondary beat frequency was observed. At >7 Hz, beat frequency was absent. The blood pressures in the aorta showed a sharp drop at 2.5 Hz and a tendency to remain 15–20 mm Hg below baseline over the 5–10 minute observation period. This was first demonstration that periodic body acceleration adds pulses to the natural arterial pulse. The authors believed that the fall in blood pressure might be the result of "some physiologic regulatory mechanism." They further stated, "Unfortunately these data do not permit elucidation of any possible mechanism involved."

Dines, J. H.; Sutphen, J. H.; Roberts, L. B.; Ashe, W. F. (Arch. Environ. Health 1965;11:323–326) applied periodic pGz with a horizontal shake table in supine, anesthetized dogs using sinusoidal, headward-footward motion at 4, 7, and 11 Hz at peak accelerations of 0.3, 0.6, and 1.3 g. The table oscillations superimposed upon the dog's arterial pressure waveform.

These superimposed oscillations were sinusoidal and appeared to fluctuate from trough to peak about 8 mm Hg. There was a fall in systemic vascular resistance immediately after onset of shaking at 4 and 7 Hz but not with 11 Hz. The cardiac output rose and blood pressure fell resulting in a fall of systemic vascular resistance. The authors speculated that the fall of systemic vascular resistance might have been due to epinephrine release. The knowledge that addition of pulses to the circulation caused release of mediators from the vascular endothelium was not known at the time these experiments were carried out.

Vertical Posture-PGZ

Bhattacharya, A.; Knapp, C. F.; McCutcheon, E. P.; Edwards, R. G. (J. Appl. Physiol. 1977;42:682–689) reported cardiovascular data in six awake, chronically instrumented canines were restrained with their spines vertical, and exposed to Gz sinusoidal vibration of 2–12 Hz for a constant peak acceleration amplitude of ±1.0 G. Vibration exposures of 30 s with intervening recovery periods of 2 min were employed. The following variables were measured:

mean heart rate (MHR), stroke volume (SV), mean aortic flow (MAF), mean aortic pressure (MAP), the peak net force transmitted to the canine/body weight (PNF/BW), and the vibration platform frequency (ft), displacement, and acceleration. The percentage change from control (no vibration) of MAF varied linearly with PNF/BW for all cases. MAF also varied linearly with the log MHR/ft for the number of dogs that primarily changed MHR during the vibration exposures.

The response of MAP was minimal in all cases, indicating a decrease in total peripheral resistance with increasing PNF. These authors utilized much higher forces of pGz, ±1.0 G, values too uncomfortable for humans to accept for more than a few minutes. This value is far greater than recommended in the following patent application using the motion platform, ~±0.2 to ±0.6 pGz. Bhattacharya et al did not consider nitric oxide release as a mechanism but attributed their findings to neural stimulation. Further, at such G levels, endothelin-1, a vasoconstrictor mediator, may be released from endothelium because of high circumferential stress of the vessels (Hoeks, A. P. G.; Samijo, S. K.; Brands, P. J.; Reneman, R. S. Hypertension 1995;26:26–33).

Synchronized Oscillating Acceleration

Bhattacharya, A.; Knapp, C. F.; McCutcheon, E. P.; Evans, J. M.: J. Appl. Physiol 1979;47:612–620) paced the heart of dogs at 2 to 3 Hz at the frequency of the oscillating force platform. This system synchronized displacement of the platform with the paced heart of the animal. A function generator produced a sinusoidally varying voltage for input to the platform and to a variable delay circuit that triggered a stimulator for cardiac pacing. This technique that was termed External Acceleration Synchronized with ECG (EASE) provided steady-state sinusoidal acceleration of any desired amplitude or frequency while simultaneously driving the heart at the same frequency with a controlled delay of synchronization time between initiation of platform motion and the point within the cardiac cycle. The animals were oscillated headward to footward at peak acceleration of ±0.75 g for 5 minutes followed by a 20-minute recovery period.

Stroke volumes increased from 15 to 32%, and mean arterial pressure from 2 to 12%. Myocardial oxygen consumption increased from 9–42%. Since increase of nitric oxide causes a decrease in myocardial oxygen consumption, perhaps other mediators were released at these higher g forces (0.75) than discussed in relation to the preferred embodiment of the present invention. Indeed, Bhattacharya et al noted that the observed cardiovascular responses could not be wholly described by the effect of the hydraulic component of the mechanical forcing function. The authors suggested that behavior of the valved venous system should also be considered but did measure properties in the venous system. They further added that neurohormonal and metabolic contributions to the response might also play a part. They indicated that changes in vagal tone might play an important role in mediation of cardiac responses to periodic body acceleration.

In comparison to EASE, the cardiovascular effects on normals were less with intra-aortic balloon pumping, intraarterial counterpulsation and external counterpulsation.

Based upon this study and others in the literature, the authors speculated as follows, ". . . use of whole-body vibration as an exercise-like substitute to prevent cardiovascular and musculoskeletal deconditioning resulting from long-term bedrest, paralysis, or weightlessness encountered during space flight. It may be reasoned that cardiovascular and musculoskeletal conditioning may be achieved by using an oscillating bed to simulate the "G profile" of normal erect adults. The technique could also be synchronous with the heartbeat if its efficacy were proven to be substantially greater than that of the nonsynchronous case." They further note the following: "The practical applications of whole-body oscillating acceleration, whether synchronous or asynchronous, whether for diagnostic/therapeutic benefits for cardiac patients or as countermeasure to deconditioning of paralysis, immobilization or weightlessness, require detailed quantitative investigations. Such studies should include determination of safe and tolerable acceleration forces for effective loading of the cardiovascular and musculoskeletal systems. The testing of whole-body oscillation as an exercise substitute and reconditioning tool for normal human subjects should be a safe area for initial evaluations of the therapeutic aspects of this technique."

In both modes of operation, synchronous and nonsynchronous, the effect on blood pressure waveforms was similar to external counterpulsation with small pulses exhibiting variable delays from the R wave trigger. This differs from external addition of pulses to the circulation in this patent application that is not limited to cardiac cycles nor triggered from the heart rate. Further, pGz recommended in the this patent application ranges from ±0.2 to ±0.6 pGz whereas Bhattacharya utilized ±0.75 in their studies. Values of pGz equal to ±0.75 are too uncomfortable for humans to accept for more than a few minutes.

External Counterpulsation

External counterpulsation (ECP), also designated enhanced external counterpulsation (EECP) involves applying cuffs to the calves, thighs, and optionally to the buttocks, sequentially inflating the calve, thigh and buttock cuffs with air to 200 to 300 mm Hg at the onset of each cardiac diastole and deflating all the cuffs at the onset of systole. There are two major manufacturers of this technology in U.S., Vasomedical and Cardiomedics. With this method, two pulses appear on the arterial waveform with each heartbeat. The first pulse occurring immediately after the QRS complex of the electrocardiogram (ECG) is due to the normal emptying of the heart with each beat and termed systole. The second pulse of similar amplitude to the first occurs after the T wave of the electrocardiogram and is produced by movement of blood upward in a retrograde manner from the lower body during compression by ECP. The digital pulse plethysmograph during EECP demonstrates that the diastolic waveform amplitude with EECP exceeds the patient's systolic amplitude, considered as optimal setting for the device. Since the compression and deflation of ECP are tied to ECG triggering, this method cannot be used in patients who have atrial fibrillation or frequent premature ventricular beats that interfere with such triggering.

The initial purpose of ECP was to achieve better coronary arterial perfusion during diastole and its beneficial effects in the relief of chronic angina pectoris have been well documented. While the heart is in diastole, the cuffs are inflated in rapid sequence from the calves upward, creating a pressure wave that increases diastolic pressure, coronary artery perfusion pressure, and blood flow to the heart muscle. This compression of the blood vessels in the legs also increases the volume of blood returned to the right side of the heart via the venous system. Instantaneous deflation of all cuffs at the onset of the heart's contraction lowers the resistance the heart must pump against, decreasing the heart's work. This latter effect, when coupled with increased venous return, significantly raises cardiac output. The overall effect is to increase the oxygen supply of the heart, while decreasing its oxygen demand. The beneficial effects on other organs such as the brain and kidney have also been observed. Thus, the mean carotid flow increased by 22% and the mean renal artery flow increased by 19%. ECP might also have a therapeutic role in 1) hypotension or shock, 2) in conjunction with thrombolytics to improve perfusion, 3) in systolic dysfunction to reduce afterload and to reduce mitral regurgitation, and 4) as an outpatient form of coronary revascularization.

External counterpulsation is a non-invasive means to add another pulse to the circulation with each heart beat whereras intraaortic balloon pumping is invasive procedure that also accomplishes the same result. The hemodynamic effects of these two methods are comparable. Toyota et al. (Endothelium-derived nitric oxide enhances the effect of intraaortic balloon pumping on diastolic coronary flow. Ann. Thorac. Surg. 1999;67:1254–1261) showed that intraaortic balloon pumping augmented coronary blood flow by dilating coronary arteries in distole through release of nitric oxide from eNOS. Thus, ECP would be expected to produce the same effects.

Basis for ECP

The basis for the long lasting effects of ECP in patients with angina pectoris was initially thought to be due to the increased blood flow attendant with each heartbeat stimulating collateral channels for coronary blood flow. However, recent evidence indicates that nitric oxide is liberated into the blood stream with each ECP treatment. Nitric oxide release relates to addition of another pulse to the circulation, a known stimulus to vascular endothelium with upregulation of eNOS.

In a pivotal study, the ECP device manufactured by Vasomed, pressure was applied to cuffs at 300 mm Hg for active group (71 patients) and 75 mm Hg for the control group (66 patients). Changes in pulse waveform were monitored by finger plethysmography. To assess hemodynamic effect of ECP, two ratios were computed, using the systolic and diastolic peak pressures or the area under the systolic and diastolic curves. The means of patients' diastolic to systolic pressure and area under the curve ratios were 1.41, SD 0.51 and 1.59, SD 0.6, respectively. Ratios greater than one correspond to diastolic greater than systolic values. The continued relief of angina beyond the actual hemodynamic effects might be related to the following: 1) opening of collaterals, 2) chronic exposure to ECP could lead to increased production of nitric oxide and prostacyclin through shear stress; in turn this leads to upregulation of eNOS gene expression, and 3) increased blood flow may release a variety of paracrine substances (e.g., estrogens) that participate in vascular remodeling and reactivity.

In ECP, an augmentation in flow volume as meaasured with duplex doppler scanning was found in the carotid, renal, and hepatic arteries from 20% to 25% and in the coronary arteries from 20% to 40%. Stroke volume increased by 12%. The augmentation of blood flow was accompanied by an increase in mean blood pressure of 15%.

Flow-mediated shear stress associated with external counterpulsation affects plasma nitric oxide and endothelin-1 levels. In the usual course of treatments of 36 hours over 18 to 36 days, there are statistically significant increases in plasma nitric oxide and reduction of endothelin-1 compared to baseline. These effects persist at a reduced level 3 months after stopping the treatments.

Erectile Dysfunction

A Vasomed ECP device was utilized to treat men with erectile dysfunction for 20 days, 1 h per day. The beneficial subjective effects of external counterpulsation revealed increased penile peak systolic blood flow that might have opened existing or led to development of new collateral channels. However, this treatment is time consuming and costly.

Alzheimer's Disease

The examination of Hasegawa's Dementia Scale (HDS), single photon emission computed tomography (SPECT) brain imaging, and some biochemical parameters in blood and cerebrospinal fluid were selected to evaluate the effect of external counterpulsation therapy for Alzheimer's disease. After of ECP, the average HDS score of the patients increased, and the cortical cerebellar ratios of SPECT brain scan, the superoxide dismutase (SOD) activity and the concentrations of somatostatin-like immunoreactivity (SLI), dynorphin AL-13 (Dyn Al-13) in blood and/or cerebrospinal fluid became significantly elevated. Thus, external counterpulsation not only improves cerebral blood flow but also makes a notable impact on biological active substances in blood and cerebrospinal fluid.

Side Effects of ECP and Relative Contraindications

External counterpulsation may be associated with the following side effects 1) skin abrasion, bruise or blister, 2% in control group (75 mm Hg cuff pressure) and 13% active ECP group (300 mm Hg cuff pressure) and 2) pain in legs and/or back 7% in control group and 20% in active ECP group. This treatment modality cannot be used in patients with chronic atrial fibrillation or frequent premature cardiac contractions because of problems in triggering counterpulsation to varying RR intervals.

Summary

ECP is a means for inducing pulses into the vascular system that is coupled to the heartbeat. The heartbeat must be regular for utilization of the technology. The effectiveness of the device probably relates to the added vascular pulses that stimulate release of mediators from the vascular endothelium, particularly nitric oxide, prostacycline and t-PA. The frequency of the added pulses is limited to the fundamental rate of the beating heart.

Intermittent Compression of Extremities

Intermittent pneumatic compression (IPC) of the foot (IPC (foot)), calf (IPC (calf)) or both (IPC (foot+calf)) augments calf inflow, and improves the walking ability and peripheral hemodynamics of claudicants (IPC (foot), IPC (foot+calf)), largely due to venous outflow enhancement. The frequency of added pulses in standard intermittent pneumatic compression therapy of the lower extremities ranges from 2 to 4 per minute. This augments flow and is associated with decreased pulsatility index signifying fall in peripheral resistance. The optimal setting for the intermittent compression device is defined as the lowest pressure, frequency and time delay that achieves an almost complete and well-sustained decrease in lower limb venous pressure. The low frequency of external addition of pulses to the circulation, e.g., 2 to 4 impulses per minute, cannot produce significant shear stress on vascular endothelium to enable release of significant amounts of nitric oxide and t-PA. However, flow dependent shear stress analogous reactive hyperemia may be operative with this treatment modality.

An intermittent pneumatic compression (IPC) is described that consists of two cuffs, one for each leg were connected to an air pump. The cuffs are fitted to the legs in a non-circumferential manner on the medial and lateral sides of the leg and held in place by rubber bands. The pump provided a pressure up to 55 mm Hg achieved within 1 second after onset of inflation. An inflation cycle consists of 5 sec of inflation followed by 25 sec of deflation. The pressure with this device operates at lower pressures than conventional circumferential compression. Cuffs used in these experiments have the following advantages over other circumferential devices: 1) non-circumferential compression of the legs more effectively empties blood vessels and allows better venous return to heart, 2) more comfortable because of lower pressures, 3) produces higher venous flow velocity, and 4) faster inflation. This device does not change heart rate or blood pressure. It produces local vasodilation that took place with commencement of IPC and disappears after its termination. ICP to the legs increases shear stress up to 200 dynes/cm$^2$ whereas resting shear stress is 15 dynes/cm$^2$. The flow mediated vasodilation is attributed to nitric oxide release because vasodilation is blocked by L-NNMA.

The standard calf-length sequential device for intermittent compression of extremities to prevent deep venous thrombosis gives a peak pressure of up to 50 mmHg with an inflation time of 12 seconds cycling at 60 sec. High pressure devices on the foot, or foot and calf give a peak pressure between 120 and 160 mm Hg with an inflation time of 1 to 2 seconds and a cycle time of 22 to 30 sec. High pressure devices cause increased tangential shear stress on the vascular endothelium because of higher maximum venous velocities. This causes release of nitric oxide and prostacyclin from venous vascular endothelium. Although high-pressure compression over the lower extremities adds a pulse at 0.5 to 1 Hz intermittently, its effects are more analogous to reactive hyperemic stimulation of the endothelium than the invention in the current application that externally adds pulses at intervals of 1 to 6 Hz onto the fundamental vascular pulse.

Intermittent compression devices in current clinical use weakly stimulate venous endothelium locally through flow shear stress. Adding pulsations to venous blood flow is a much more potent stimulus to upregulation of eNOS and increase of tissue plasminogen activator to decrease incidence of deep venous thrombosis (Dai G et al. An in vitro cell culture system to study the influence of external pneumatic compression on endothelial function. J.Vasc.Surg. 2000;32:977–87).

Motion Platform

Horizontal

As discussed above, the motion platform described in U.S. Pat. No. 6,155,976 is the means for adding external pulses in the preferred embodiment of the present invention. The platform moves on rollers and is driven by single or multiple flywheels powered by an electric motor. Frequency is regulated by a controller on the electrical motor and displacement by physically changing weights on the flywheels. The platform device can also be fabricated with two flywheels and two pairs of weights powered by a motor. Adjustment of displacement is achieved by a timing belt mechanism and this improved device can be run at frequencies from 0 to 6 Hz and with pGz from 0.1 to ±0.6. The motion platform devices add pulses to fluid channels of body as a function of the platform frequency once a critical threshold of pGz is exceeded, nominally ~±0.2 g. The body is fixed to the mattress of the platform by attaching the feet to a shoe support (e.g., Cast Boot, Darco, Huntington, W. Va.) that is bolted to a vertical board at the foot of the motion platform. The legs are fixed in the extended position voluntarily or by means of a restraining belt. This device is the preferred embodiment for generating pulses added to the fluid channels of body.

It is important that the added pulses do not entrain to the subject's own pulse wave thereby causing systolic augmentation of the primary wave without added pulses. This can be minimized by setting platform frequency to higher rates than the subject's own heart rate but entrainment can still occur as a harmonic. For example, if the subject's heart rate is 60 beats per minute and the motion platform frequency is 120 beats per min., then every other beat will be augmented thereby dissipating ½ but not all of the effects of the additional pulses. This can be further minimized by observing the vascular pulses from a vessel such as the finger on a display screen and manually or via a servo system adjusting the platform frequency to values slightly different than 120 beats per minute. For example, the motion platform could be cycle through 110, 115, 120, 125 and 130 beats per minute every minute or so.

Semi-Recumbent or Head-Down Position

The horizontal platform as described above is utilized but wedges of solid urethane or like material are placed under the head or lower body to achieve the semi-recumbent or head-down position, respectively. Alternately, the motion platform can have an adjustable break as in a hospital bed to provide the Trendelenberg or reverse Trendelenberg positions.

Seated Upright

The seated subject is strapped into a chair or into a wheel chair and a rotating adjustable cam powered with an electrical motor or a flywheel notor diven assembly moves the seat of the chair up and down at frequencies from 0.1 to 6 Hz and with pGz from 0.1 to ±0.6. This device adds pulses to fluid channels of body as a function of the seat frequency once a critical threshold of pGz is exceeded, nominally ~±0.2 g. This method requires means for head and neck support.

Platform under Feet in Seated Posture

The seated subject's feet are strapped onto a platform placed on the floor and a rotating adjustable cam powered with an electrical motor moves the platform up and down at frequencies from 0 to 6 Hz and with pGz from 0.1 to ±0.6. This moves the flexed thighs up and down. The added pulses have the highest amplitude in the lower extremity fluid channels.

"Counterpulsation" not Synchronized to Heart Beat

This device comprises two pairs of air or liquid filled bladders, attached to reservoirs and pumps, placed around the legs and thighs that inflates the legs first followed immediately by the thighs. It then empties the thigh bladders followed immediately by the leg bladders. It accomplishes this cycling at cuff pressures ~300 mm Hg and sinusoidal rates of 1 to 4 Hz. An abdominal bladder can also be used along with the leg and thigh bladders. A varient of this device combines a lower body negative pressure chamber that addresses problems of long space flights in microgravitational fields. Thus, treadmill exercise superimposing sinusoidal oscillations on 100 mmHg lower body negative pressure provides equivalent or greater physiologic stress than similar upright exercise on Earth. Exercise within a lower body negative pressure chamber may provide a cost-effective and simple countermeasure to maintain the cardiovascular and neuro-musculoskeletal systems of astronauts during long-duration flight. The external addition of pulses into the lower body negative pressure chamber improves efficiency of this countermeasure.

High Frequency Sinusoidal Compression of Extremities

This device comprises two pairs of air or liquid filled bladders, attached to reservoirs and pumps, placed around the legs. It inflates the leg bladder and deflates it cycling at cuff pressures ±300 mm Hg and sinusoidal rates of 1 to 4 Hz.

High Frequency Oscillatory Ventilation with Added Dead Space

High frequency oscillatory ventilation utilizing much larger pressures than currently employed for ventilatory means has the best potential for adding pulses without causing gas trapping. The latter can be controlled by a bias flow mechanism. In this application, an apparatus dead space must be interposed between the device and the airway to prevent unacceptable hyperventilation. The conventional frequency for this ventilatory assistance mode is about 10 to 20 Hz. However, these frequencies add pulses to the circulation that are too high to stimulate endothelial release of mediators. Therefore, the oscillatory rate needs to be set much lower, nominally 4 to 5 Hz to be effective.

II. Treatments Using Mediators Produced by External Pulses

Vascular Endothelial Growth Factor (VEGF)

Vascular endothelial growth factor (VEGF)/vascular permeability factor (VPF) is an endothelial cell (EC) mitogen. This feature is considered central to the documented role of VEGFNPF in promoting angiogenesis. Low oxygen is the key stimulus for expression of vascular endothelial growth factor (VEGF) in several adherent cells. In contrast to smooth muscle cells, VEGF release from polymorphonuclear leukocytes and platelets or VEGF mRNA expression in polymorphonuclear leukocyes is not stimulated under hypoxic conditions. Hypoor hyperthermia and acidosis, other conditions potentially associated with ischemic and inflammatory tissue injury, also did not stimulate VEGF secretion from these cells. Stimulation of platelets with thrombin induces a time-dependent release of VEGF. Rapid release of VEGF from platelets and polymorphonuclear leukocytes may occur independently of oxygenation during inflammation and hemostasis. VEGF has potent vascular permeability-enhancing properties in addition to being an endothelial cell mitogen and a chemo-attractant for mononuclear cells.

Shear stress induces a significant biphasic regulation pattern of VEGF with significant downregulation after prolonged perfusion. Thus, external addition of pulses to the circulation downregulate the VEGF release from vascular endothelium. In untrained skeletal muscle, acute exercise greatly elevates VEGF but this response to acute exercise in trained muscles is markedly attenuated. These data support the concept that VEGF is involved in exercise-induced skeletal muscle angiogenesis and is subjected to negative feedback mechanism as exercise adaptations occur. It is now believed that nitric oxide modulates VEGF release.

Patients with proliferative retinopathy demonstrate elevated peripheral markers of angiogenesis and endothelial dysfunction, suggesting a role for these processes in the pathogenesis of this condition. A fall in levels of VEGF after successful laser treatment provides opportunity for monitoring disease progression or relapse via a blood sample.

VEGF has both beneficial and detrimental actions. It has been recommended as gene therapy for promoting neogenesis in damaged myocardium but continuous expression has been found to be deleterious. On the other hand, malignant tumors and inflammatory cells secrete VEGF leading to blood supply of the tumor. Its detrimental consequences are tumor and metastatic growth and drugs are being developed to combat this effect.

Endothelial Mediation in the Heart

The major sources of nitric oxide for contractile regulation of the heart are 1) eNOS in cardiac endothelial cells and 2) eNOS in cardiac myocytes themselves. In response to pulsatility and increased shear stress, nitric oxide hastens left ventricular (LV) relaxation and increases its distensibility. Variations in the release of NO as a function of prevailing cardiac workload, signaled by preload, coronary flow, mechanical forces and heart rate, may provide an acute autoregulatory feedback that optimizes LV diastolic performance and overall pump function—possibly even on a beat by beat basis. Deficient production of nitric oxide in left ventricular hypertrophy, the cardiac allograft, and heart failure contribute to diastolic dysfunction. Here, augmentation of nitric oxide may be beneficial.

If the heart were to function as a purely systolic pump without the ability to transduce changes of preload into parallel changes of nitric oxide, then abrupt changes in preload should produce abrupt changes in cardiac output. However, this is not so—abruptly increasing or decreasing preload is gradually not abruptly followed by parallel changes in nitric oxide over several cardiac cycles, an autoregulatory system. Denuding cardiac endothelial and endocardial cells abrogates the nitric oxide signal and indicates that these cells transduce mechanical stimulation into nitric oxide production in the heart. Nitric oxide release from the beating heart may prevent thrombosis within poorly contracting hearts. Nitric oxide also diminishes myocardial oxygen consumption thereby improving efficiency of cardiac pumping capabilities and limiting extent of ischemic damage as in myocardial infarction.

External addition of pulses to the circulation that promote release of nitric oxide from cardiac endothelial cells and cardiac myocytes have potential to be beneficial in treatment of left ventricular hypertrophy, the cardiac allograft, heart failure, diastolic dysfunction, myocardial ischemia and prevention of intracardiac thrombosis.

Endothelial Mediation in Lymphatics

Nitric oxide is an endothelium-dependent relaxant factor that regulates tracheobronchial lymphatic smooth muscle tone. Lymphatic endothelium cells produce nitric oxide in response to circumferential and tangential shear stress. Nitric oxide causes sustained relaxation and dilation of the lymphatic vessels which facilitates removal of excess permeation of fluids and plasma proteins across the blood vascular capillary wall.

In supradiaphragmatic and cervical thoracic lymphatic ducts, pulses are transmitted from contiguous large arteries, the lymphatic pulse pressure representing a significant fraction of the peak lymphatic pressure. In the neck, venous pulses are also transmitted to the lymph channels. These pulses are associated with proximal flow of lymph.

External addition of pulses to the body's fluid channels causes sustained relaxation and dilation of lymphatic vessels, due to release of nitric oxide from lymphatic endothelium, which facilitates removal of excess permeation of fluids and plasma proteins across the blood vascular capillary wall, thereby being beneficial to patients with impaired lymphatic drainage.

Endothelial Mediation in Interstitial Spaces of Bone

The stress-driven flow of interstitial fluid through the bone canaliculi, the stimulus for mechanosensation in bone that causes release of nitric oxide and prostacyclin from osteoblasts. Osteoblasts in osteoporotic patients have impaired release of these mediators in response to shear stress.

External addition of pulses to the body's fluid channels causes release of nitric oxide and prostacyclin from bone osteoblasts that aid in promoting bone growth in states where mediator release is deficient such as osteoporosis.

Endothelial Mediation in Cerebrospinal Fluid

Cerebrospinal fluid (CSF) pulsations arise from change of blood volume in the closed craniospinal cavity and can be demonstrated by MRI. The blood volume changes are due to cerebrovascular and spinal vascular pulsations. Ultrastructural findings, such as gaps between endothelial cells and tubule-like endothelium-lined structures (arachnoid granulations) in proximity to the cerebrospinal fluid can be demonstrated by both transmission and scanning electron microscopy.

The pia mater of the human brain hemispheres has liquor canals that form a continuous network communicating with the cisterns of the brain base. The wall of the liquor canals is formed by a fibro-collagenous framework covered from two sides with the arachnoidendothelium. In the canal walls there are openings, through which the lumens of the canals communicate with the lumens of alveoli. The liquor canals are divided into the circulatory and excretory ones. The circulatory canals are disposed in the depth of the cerebral sulci, the secretory canals—on the surface of the convolutions. The liquor moves along the circulatory canals from the cisterns of the brain base onto the surface of cerebral hemispheres. Excretory canals adjoin the arachnoid membrane that is part of its wall (the "roof"). In the "roof" of the liquor canals the fibrocollagenous basis and the number of layers of the arachnoid-endothelium are reduced, the intercellular spaces between the cells of the arachnoidendothelium are dilated.

Through the roofs of the liquor canals the liquor is excreted from the subarachnoid space into the subdural space. Inside the liquor canals there are arteries of the pia mater hung up to the canal walls by trabeculae (cords) of a dense connective tissue.

Nitric oxide donors, such as nitroprusside, introduced into the cerebrospinal fluid cross the brain-blood barrier and are effective in treating cerebrovasospasm after subarachnoid hemorrhage. Thus, the endothelial lining of the pia matter and its proximity to pulsating cerebrospinal fluid is positioned to release similar mediators as vascular endothelium. These mediators probably play a role in cerebrospinal drainage and regulate vasomotor activity among other functions.

External addition of pulses into the cerebrospinal fluid releases mediators from endothelial pia matter to aid cerebrospinal fluid drainage as well as to provide vasodilation and increased blood flow in strokes.

Coagulation Mediators

Nitric Oxide

Nitric oxide is not only is a potent vasodilator, it also inhibits platelet adherence and aggregation, reduces adherence of monocytes and leukocytes to the endothelium, and suppresses proliferation of vascular smooth muscle cells.

Tissue Plasminogen Activator

Tissue plasminogen activator is released from vascular endothelium through shear stress. Further, shear stress is a potent fluid mechanical stimulus for upregulation of the intracellular storage pool of t-PA in the vascular wall. Shear stress effect is associated with an increased t-PA gene expression. t-PA is measurable in plasma and therefore also is a marker of endothelial function. Muscarinic agents such as acetylcholine and methacholine release tissue plasminogen activator (t-PA) in the forearm circulation of normal subjects. In patients with hypertension, acetylcholine does not change flow and net release and concentration gradients of t-PA, but increases blood flow in normal subjects indicating that vasodilatation by increasing fluid shear stress induces t-PA release with normally functioning vascular endothelium. Marked t-PA release occurs in response to isoproterenol, a beta-adrenergic agonist that acts through the nitric oxide-L-arginine pathway. This effect is independent of the effects of shear stress due to increased blood flow because nitroprusside, an endothelium-independent vasodilator induces similar increases in blood flow without causing t-PA release. Possibly, circumferential shear stress is a more potent stimulus to t-PA release than tangential shear stress.

Elevated intraluminal pressure downregulates tPA gene and protein expression and inhibits its release from the endothelium independently of shear stress. The defective capacity for stimulated tPA release that is demonstrable in patients with systemic essential hypertension might thus be an effect of the elevated intraluminal pressure per se.

External addition of pulses to the circulation causes increase storage and release of t-PA from vascular endothelium.

Substance P

Effective endogenous fibrinolysis requires rapid release of endothelial tissue plasminogen activator (t-PA). Substance P, a neuropeptide formed in sensory nerves, causes dose-dependent increases in blood flow and plasma t-PA antigen and activity concentrations, but has no effect on plasminogen activator inhibitor type I (PAI-I) or von Willebrand factor concentrations. In the presence of L-NMMA, a NOS inhibitor, substance P causes significant increases in blood flow and t-PA antigen and activity concentrations but such increases are significantly less than with substance P alone. Therefore, the L-arginine/nitric oxide pathway contributes to substance P-induced t-PA release. This provides an important potential mechanism whereby endothelial dysfunction increases risk of atherothrombosis through a reduction in the acute fibrinolytic capacity.

Effects on coagulation parameters

In patients with acute myocardial infarction or stroke, recombinant tissue plasma tissue activator (rt-PA) causes moderate decrease of fibrinogen and moderate increase of fibrinogen degradation products. Therefore, functional integrity of the vascular endothelium can be checked by measuring these parameters after external addition of pulses to the circulation. In addition, measurement of these parameters allows titration of treatment effectiveness in situations where the end-point is a desired level of fibrinolysis.

Activator Protein-1 (AP-1)

Activator protein-1 (AP-1) is composed of c-fos/c-jun hererodimers or c-jun/c-jun homodiamers. This is released from vascular endothelium with shear stress and/or circumferential pulses. The AP-1 transcription factor family is important in the transcription of several genes, e.g., monocyte chemotactic protein-1 (MCP-1) and the vascular cell adhesion molecule-1. Endothelial cells subjected to disturbed laminar shear stress exhibit increased levels of nuclear localized NF-kappaB, Egr-1, c-Jun, and c-Fos, compared with cells exposed to uniform laminar shear stress or maintained under static conditions. In addition, individual cells display a heterogeneity in responsiveness to disturbed flow, as measured by the amount of NF-kappaB, Egr-1, c-Jun, and c-Fos in their nuclei. This differential regulation of transcription factor expression by disturbed versus uniform laminar shear stress indicates that regional differences in blood flow patterns in vivo-in particular, the occurrence of spatial shear stress gradients-may represent important local modulators of endothelial gene expression at anatomic sites predisposed for atherosclerotic development.

Endothelial Dysfunction

There are several disorders associated with reduced synthesis and/or increased degradation of vascular nitric oxide and/or increased release of endothelin-1. These include among others hypercholesterolemia, hypertriglycidemia, diabetes mellitus, systemic and pulmonary hypertension, chronic heart failure and tobacco use. The endothelial dysfunction caused by these disorders contributes to the alterations in vascular function and structure observed in these conditions. Reduction of vascular nitric oxide plays a significant role in the development of atherosclerosis. Finally, reperfusion injury after myocardial ischemia or postcardiopulmonary resucitation is due to a cascade of polymorphonuclear neutrophil (PMN)mediated injury. Its magnitude is inversely correlated to the bioavailability of nitric oxide released from eNOS.

Chronic Heart Failure

Chronic heart failure (CHF) is associated with abnormal endothelium-dependent vasodilation of both small and large blood vessels. The impaired endotholial function in chronic heart failure is multifactorial, including reduced expression of eNOS (secondary to reduced flow and shear stress), activation of the renin-angiotensin system and enhanced degradation of nitric oxide caused by inactivation with free radical molecules. The relationship of these abnormalities to mild heart failure severity is near maximum with endothelium dependent vasodilation, e.g., acetylcholine administration, but is graded as to severity with endothelium independent vasodilation, e.g., nitroprusside administration, a drug that acts directly on vascular smooth muscle. In patients with stable CHF, bicycle ergometer lower limb exercise training leads to a correction of endothelial dysfunction of the upper extremity, indicating a systemic effect of local training on endothelial function (Linke A, Schoene N, Gielen S, Hofer J, Erbs S, Schuler G et al. Endothelial dysfunction in patients with chronic heart failure: systemic effects of lower-limb exercise training. J. Am. Coll. Cardiol. 2001;37:392–97). Therefore, even in CHF patients with compromised endothelial function, exercise training with cycling that increases shear stress is effective in restoring systemic endothelial function. In an analogous way to exercise training, chronic treatment with external addition of pulses to the circulation in patients with chronic heart failure upregulates basal release of nitric oxide, thereby ameliorating many symptoms of chronic heart failure.

Coronary Spasm

Patients with coronary spasm, also designated atypical or varient angina pectoris may have normal peripheral vascular endothelial function. But coronary vascular endothelium dysfunction is present. In one cause of this entity, there is $T^{-786} \rightarrow C$ mutation in the 5'-flanking region of the endothelial nitric oxide synthase gene. This genetic mutation increases basal vasomotor tone of coronary arteries and enhances the response to the vasoconstrictor effect of acetylcholine and the vasodilator effect of organic nitrates because endothelial nitric oxide synthesis is reduced. Deficiency of nitric oxide in cells with this mutation also increases synthesis of endothelin-1 and angiotensin II that produce vasoconstriction and smooth muscle proliferation.

Chronic treatment with external addition of pulses to the circulation in patients with coronary spasm does not increase myocardial oxygen consumption as does exercise—which provokes coronary spasm in such patients. In fact, myocardial oxygen consumption may diminish in the presence of nitric oxide. Thus, external addition of pulses to the circulation by upregulating coronary vascular endothelium eNOS, which is deficient in this entity, thereby diminishes the frequency and intensity of coronary spasm episodes.

Diastolic Dysfunction

Normal myocardial endothelial function maintains normal diastolic function whereas myocardial endothelial dysfunction is associated with diastolic dysfunction. In patients with anterior myocardial infarction and restrictive filling pattern with elevated E/A ratios and decreased deceleration time from echo-doppler estimation of transmitral blood flow, intravenous nitroglycerin significantly reduces the elevated E/A ratio toward normal and increases the deceleration time of the E wave toward normal.

Chronic treatment with external addition of pulses to the circulation upregulates eNOS in myocytes and endocardium thereby improving diastolic function.

Systemic Hypertension

Abnormality of endothelial release or bioactivity of nitric oxide in systemic hypertension is antecedent to vascular smooth muscle growth and eventual atherosclerosis. Testing for endothelial dysfunction identifies individuals at risk for cardiovascular events. These tests involve an impaired response of forearm blood flow after brachial arterial infusion of acetylcholine or of inhibition of nitric oxide through administration of L-NAME to induce regional and systemic vasoconstriction directly related to the magnitude of basal nitric oxide effect. Because endothelial function is directly involved in maintaining a low arterial tone and preventing vascular smooth muscle hypertrophy, maintenance of a normal arterial compliance depends on the adequacy of nitric oxide release and effect. Cardiovascular events usually result from vascular accidents superimposed on the abnormal structure of the blood vessel. Thus, the vasculature health of individual patients with hypertension differentiates the risk from the non-risk patient. This is because hypertension is only one of many factors that contribute to the incidence of vascular events.

Offspring of essential hypertensive patients often have reduced vasodilator response to acetylcholine linked to a defect in the nitric oxide pathway, suggesting that impaired nitric oxide production precedes onset of essential hypertension.

Authorities in the field have recommended that practical screening techniques are needed to assess the properties of arterial walls in an at-risk population. Further, such methods should allow monitoring of changes in properties during therapeutic interventions. Thus, a drug regimen that does not favorably affect arterial wall properties in a given patient can be replaced by another drug regimen that might be more effective. Correction of arterial wall abnormality could then serve as a guide to therapeutic efficacy rather than the employing only absolute level of blood pressure, which now serves as a surrogate marker.

External addition of pulses to the circulation along with monitoring the position of the dicrotic notch and/or Augmentation Index of the digital pulse plethysmograph can determine status of endothelial function as a practical screening test. Downward displacement of the dicrotic notch on the diastolic limb and/or reduction of Augmentation Index in systole signify release of nitric oxide from normal endothelium. These parameters show no change or minimal change when endothelial dysfunction is present. These phenomena relate to dilation of resistance vessels by nitric oxide released from normal endothelium that leads to less pulse wave reflection.

Chronic treatment with external addition of pulses to the circulation upregulates basal production of nitric oxide, prostacyclin and t-PA, all of which are reduced in systemic hypertension. Upregulation minimizes risk to cardiovascular events associated with hypertension, e.g., stroke and myocardial infarction.

Pulmonary Hypertension

Compared to normal subjects, patients with primary or secondary pulmonary hypertension have raised levels of circulating endothelin-1, a vasoconstrictor mediator and a trend toward lower levels of nitric oxide.

Chronic treatment with external addition of pulses to the circulation by stimulating endothelial release of nitric oxide, prostacylin, and tissue plasminogen activator, while suppressing endothelin-1 and tissue plasminogen inhibitor, brings pulmonary arterial pressures down toward normal levels and inhibit thrombus formation.

Raynaud's Phenomenon

In patients with Raynaud's phenomenon associated with scleroderma, endothelial dysfunction does not allow adequate nitric oxide, prostacyclin, and t-PA release. Further, such patients also have elevated levels of endothelin-1.

Chronic treatment with external addition of pulses to the circulation stimulates endothelial release of nitric oxide, prostacyclin, and t-PA release, and suppresses endothelin-1 release, thereby ameliorating this disorder.

Proliferative Retinopathy

Patients with proliferative retinopathy demonstrate elevated peripheral markers of angiogenesis and endothelial dysfunction, suggesting a role for these processes in the pathogenesis of this condition. A fall in levels of vascular endothelial growth factor (VEGF) after successful laser treatment provides opportunity for monitoring disease progression or relapse via a blood sample.

Chronic treatment with that external addition of pulses to the circulation to upregulate eNOS in endothelium of the eye is beneficial in proliferative retinopathy. In addition, release of vascular endothelial growth factor from vascular endothelium may be downregulated for further benefit.

Insulin Resistance Syndrome

Insulin resistance syndrome also known as "metabolic syndrome X" is a multifaceted syndrome, which occurs frequently in the general population. It is more common in men than in women and may be a precursor to diabetes mellitus type-2. A large segment of the adult population of industrialized countries develops this metabolic syndrome, produced by genetic, hormonal and lifestyle factors such as obesity, physical inactivity and certain nutrient excesses. This disease is characterized by the clustering of insulin resistance and hyperinsulinemia, and is often associated with dyslipidemia (atherogenic plasma lipid profile), essential hypertension, abdominal (visceral) obesity, glucose intolerance or noninsulin-dependent diabetes mellitus and an increased risk of cardiovascular events. Elevated serum triglycerides commonly associate with insulin resistance and represent a valuable clinical marker of the metabolic syndrome. Abnormalities of blood coagulation (higher plasminogen activator inhibitor type 1 and fibrinogen levels), hyperuricemia and microalbuminuria have also been found in metabolic syndrome X. All of these abnormalities are associated with endothelial dysfunction including a genetic and/or acquired defect of nitric oxide synthesis. Standard treatment includes decreasing obesity, increasing physical activity, and managing dyslipidemia. The latter may require the use of cholesterol and triglyceride-lowering drugs.

Since endothelial dysfunction forms the major basis of the insulin resistance syndrome, chronic treatment with external addition of pulses to the circulation to upregulate beneficial mediator release from vascular endothelium serves as an ancillary treatment modality.

Wide Angle Glaucoma

Deficiencies in nitric oxide or nitric oxide containing cells occur in primary open-angle glaucoma. External pulses are transmitted from the circulation to the fluid bathing the trabecular meshwork of the eye. This system regulates intraocular fluid drainage. These trabecular cells contain eNOS that release nitric oxide, which in turn regulates fluid drainage.

Chronic treatment with external addition of pulses transmitted to the trabecular meshwork of the eye to stimulate release of nitric oxide from endothelium ameliorates wide angle glaucoma by facilitiating drainage that is under nitric oxide regulation.

Myocardial Reperfusion Injury

Following myocardial ischemia secondary to coronary artery disease or after successful cardiopulmonary resuscitation, there appears to be transient endothlial dysfunction. This plays an important role in the reperfusion injury that often follows such events. Thus, experimental abolition of eNOS through a mouse model that does not carry the eNOS gene dramatically exacerbates the extent of myocardial reperfusion injury following acute coronary ischemia and reperfusion. In addition, the level of coronary P-selectin expression and polymorphonuclear leukocyte infiltration into the infarcted area increases markedly in such mice. These data support the anti-neutrophil actions of nitric oxide and suggest that nitric oxide may be of tremendous value for the treatment of myocardial infarction/reperfusion injury.

Systemic Hypertension

Elevated intraluminal pressure downregulates tPA gene and protein expression and inhibits its release from the endothelium independently of shear stress. The defective capacity for stimulated tPA release that can be demonstrated in patients with essential hypertension might therefore be an effect of the elevated intraluminal pressure per se.

Chronic treatment with external addition of pulses to the circulation in patients with essential hypertension upregulates t-PA expression and restores the defective capacity to generate this molecule.

Pulmonary Hypertension

Thrombotic lesions are frequently found in pulmonary arteries in patients with pulmonary hypertension. Thrombin activity appears to be increased in severe pulmonary hypertension. Antithrombotic pathway disorders may account for this abnormality, particularly in chronic thromboembolic pulmonary hypertension and primary pulmonary hypertension.

Injured endothelium, a constant feature in severe pulmonary hypertension, either primary or secondary, enhances thrombus formation in pulmonary vessels. This is related to decreased release of tissue plasminogen activator, and impaired prostacyclin and nitric oxide release, as well as increased release of tissue plasminogen inhibitor.

External addition of pulses to the circulation stimulates endothelium to release nitric oxide, prostacyclin, t-PA and suppresses tissue plasminogen inhibitor, actions that are counter to thrombosis formation.

Coronary Artery Disease

Platelet Glycoprotein GPIIb-IIIa Complexes mediate platelet aggregation by binding fibrinogen or von Willebrand factor, protein cofactors that form bridges between adjacent platelets. Activation of these complexes in a thrombus formed in a coronary artery during an acute myocardial infarction allows its further propagation. Agents such as abciximab (ReoPro) that block this function constitute a new class of antithrombotic drugs. They provide 1) immediate relief in the case of ongoing arterial thrombosis and 2) elimination of excessive platelet reactivity in diseased vessels so that occlusive thrombi and restenosis do not occur, while allowing sufficient hemostasis to prevent spontaneous bleeding (Nurden AT et al. Platelet glycoprotein IIb/IIIa inhibitors: basic and clinical aspects. Arterioscler. Thromb. Vasc. Biol. 1999;19:2835–40). Nitric oxide and prostacycline released from vascular endothelium during exercise inhibit activation of these fibrinogen receptors [Platelet Glycoprotein GPIIb-IIIa Complexes] (Lindemann S et al. Increased platelet sensitivity toward platelet inhibitors during physical exercise in patients with coronary artery disease. Thromb. Res. 1999;93:51–59).

External addition of pulses to the circulation stimulates endothelium to release nitric oxide, prostacyclin, t-PA, suppress tissue plasminogen inhibitor, and inhibit activation of platelet fibrinogen receptors (because of nitric oxide and prostacycline), thereby resulting in an action that is counter to thrombosis formation and propogation. This effect of adding pulses to the circulation acts as a stand alone therapy or as an adjuvant to such Platelet Glycoprotein GPIIb-IIIa Complex inhibitors such as abciximab (ReoPro) in patients with acute myocardial infarction, after arterial endoplasty and during acute strokes.

Release of Nitric Oxide

Coronary Artery Disease

Administration of organic nitrates to patients with angina pectoris to is a time-tested therapy for relief of this condition. These drugs are also used in chronic heart failure but nitrate tolerance may develop when continuous administration of nitrates is utilized, particularly with transdermal nitroglycerin patches. This phenomenon does not occur with methods that externally add pulses to the circulation. In recent years, it has been established that the vigorous exercise training over a four week period significantly improves coronary endothelial function in patients with asymptomatic coronary atherosclerosis. It is thought that this improvement relates to upregulation of eNOS and other mediator genes even during non-exercising periods as a result of the increased shear stress to the endothelium brought about by exercise. In an analogous way, improvement would be predicted for any therapy that relied on adding pulses to the circulation such as the motion platform or external counterpulsation.

Angina Pectoris

The nitric oxide donor, nitroglycerin, is the treatment of choice for relieving angina; other organic esters and inorganic nitrates are also used, but its rapid onset of action and established efficacy make it the mainstay of angina pectoris relief. Nitroglycerin does not dilate small coronary artery vessels because of a relative deficiency of available sulfhydryl groups or a lack of enzymes necessary for conversion of nitroglycerin to its active metabolites. Chronic treatment with external counterpulsation, a technology that releases nitric oxide from vascular endothelium improves patients with chronic angina pectoris refractory to medical and surgical therapies. In an analogous way, external addition of pulses to the circulation through release of nitric oxide from vascular endothelium is an effective treatment for refractory angina pectoris. Both modalities have the capability of dilating small coronary blood vessels through nitric oxide and endothelial hyperpolarizing dependent factor upregulation.

Chronic treatment with external addition of pulses to the circulation upregulates eNOS of epicardial arteries and endothelial dependent hyperpolarizing factor release to ameliorate angina pectoris.

Vasospastic Angina

Vasospastic angina (variant angina) is induced by a primary reduction in local myocardial blood flow caused by epicardial arteriospasm. The condition is characterized by chest pain at rest with significant ST segment deviation on ECG. There is deficiency in endothelial eNOS activity in vasospastic coronary arteries, which leads to the supersensitivity of the artery to the vasodilator effect of nitroglycerin and to the vasoconstrictor effect of acetylcholine. About 5 to 10% of radial arterial grafts for coronary bypass surgery develop vasospasm related to eNOS deficiency or downregulation; these are supersensitive to the vasodilator effect of nitroglycerin. Anginal chest pain without creatine kinase (CK) elevation is frequently observed in the first hours after coronary stenting. Possible causes of ischemic episodes are microembolism, side branch occlusion, coronary vasospasm, and disturbances of microvascular circulation. Intravenous nitroglycerin after coronary stenting significantly reduced the occurrence of minor myocardial necrosis. Although epicardial arterial nitric oxide release is impaired in coronary arterial vasospasm, endothelium dependent vasodilation is not impaired in peripheral blood vessels.

Chronic treatment with external addition of pulses to the circulation upregulates eNOS of epicardial arteries, endothelial dependent hyperpolarizing factor and t-PA release in vasospastic arteries that become vasospastic spontaneously or postoperatively in association with arterial grafts or stents in coronary bypass procedures.

Graft Failure in Coronary Revascularization Procedures

High pressures from the arterial circulation on saphenous venous grafts utilized in coronary revascularization procedures may cause endothelium dysfunction over time and consequent diminution of nitric oxide release. This phenomenon contributes to saphenous venous graft failures in coronary revascularization procedures. L-arginine as a single intramural injection attenuates intimal hyperplasia because of generation of nitric oxide. Nitric oxide inhibits neointimal formation after vascular injury and attenuates smooth muscle proliferation both directly and indirectly by preventing the release of growth factors.

Chronic treatment with external addition of pulses to the circulation upregulates eNOS for release of nitric oxide from endothelium as well as endothelial dependent hyperplolarizing factor and t-PA to prevent venous graft failure by maintaining patency.

Redo Coronary Bypass Grafting

Preoperative treatment with Intra-Aortic Balloon Counterpulsation 1 to 2 hours prior to surgery in high-risk redo CABG patients is an effective modality to prepare these patients to have their myocardial revascularization in an as nonischemic situation as possible, which resulted in a significantly lower hospital mortality, fewer instances of postoperative low cardiac output, and shorter stays in both the intensive care unit and the hospital (Christenson JT et al. Preoperative intraaortic balloon pump enhances cardiac performance and improves the outcome of redo CABG. Ann. Thorac. Surg. 1997;64:1237–44). Counterpulsation adds pulses to the circulation thereby upregulating eNOS for release of nitric oxide from endothelium as well as releasing endothelial dependent hyperplolarizing factor, prostacyclin and t-PA. These mediators are all beneficial to myocardial function.

Acute and chronic treatment with external addition of pulses to the circulation upregulates eNOS of coronary arteries, endothelial dependent hyperpolarizing factor and t-PA release and better prepares the myocardium for redo coronary bypass graft procedures. Nitric oxide decreases myocardial oxygen consumption thereby rendering the myocardium less susceptible to ischemia.

Endothelial Dependent Hyperpolarizing Factor (EDHF)

In the coronary bed, the formation of endothelial dependent hyperpolarizing factor (EDHF) appears to play a greater role in response to shear stress than release of either nitric oxide or prostacyclin since in this vascular bed, endothelium-dependent vasodilation is only marginally attenuated by combined inhibition of eNOS and cyclooxygenase. However, EDHF is released by endothelium at other vascular sites as well. EDHF displays characteristics of a cytochrome P450-dependent arachnoidonic acid metabolite. It induces endothelium-dependent relaxations of both large and small arteries, where K channels, especially calcium-activated K channels, appear to be involved. EDHF release is inhibited by tetrabutylammonium, a nonselective inhibitor of K channels. Chronic exercise upregulates release of EDHF that ultimately dilates arteries through the nitric oxide-L-arginine pathway.

Chronic treatment with external addition of pulses to the circulation upregulates release of endothelial dependent hyperpolarizing factor (as well as nitric oxide and t-PA) that is particuarly relevant to vasodilation in coronary arteriospasm, post-stent insertion, coronary bypass surgery with arterial or venous segments and atherosclerosis.

L-Arginine Therapy

Basal and acetylcholine-stimulated release of nitric oxide is reduced in patients with coronary artery disease, either as a result of depressed synthesis of NO or excessive degradation of NO by reactive oxygen species to biologically inactive or even toxic molecules. Serum nitric oxide, in patients given oral L-arginine (9 g/day for one month) as measured by a chemiluminescent technique, did not change. Nor was there an effect on brachial artery diameters, flow-mediated dilation nor nitroglycerin induced dilation. Higher doses of L-arginine are associated with nausea, stomach cramps and diarrhea. Therefore, both ineffectiveness and side effects of oral L-arginine treatment of coronary artery disease mitigate its use in coronary artery disease. This limitation is not present in treatment with external addition of pulses to the circulation for upregulating release of nitric oxide and EDHF.

Diastolic Dysfunction

In patients with anterior myocardial infarction and restrictive filling pattern with elevated E/A ratios and decreased deceleration time estimated from echo-doppler estimation of transmitral blood flow, intravenous nitroglycerin significantly decreased the E/A ratio toward normal and lengthens the deceleration time to normal.

Chronic treatment with external addition of pulses to the circulation upregulates release of nitric oxide and endothelial dependent hyperpolarizing factor thereby improving diastolic function in patients with diastolic dysfunction of the heart.

Diabetes Mellitus

Type II Diabetes

Endothelial function may be impaired in type-2 diabetes. Interleukin-6 (IL-6), acting on hepatocytes induces acute-phase reactants that increase blood viscosity and promote thrombus formation. Hypertrophied adipocytes present in type-2 diabetes release IL-6 and hyperglycemia evokes IL-6 production by endothelium, factors that explain why plasma fibrinogen is increased in visceral obesity and poorly controlled diabetes.

Chronic treatment with external addition of pulses to the circulation stimulates endothelial release of nitric oxide, prostacyclin and t-PA thereby improving coagulation profiles in patients with type-2 diabetes mellitus.

Insulin Resistance Syndrome

Insulin resistance syndrome (IRS), also termed "syndrome X," or "metabolic syndrome X" is a distinctive constellation of risk factors for the development of type 2 diabetes mellitus and cardiovascular disease. The syndrome's hallmarks are glucose intolerance, hyperinsulinemia, a characteristic dyslipidemia (high triglycerides; low high-density lipoprotein cholesterol, and small, dense low-density lipoprotein cholesterol), obesity, upper-body fat distribution, hypertension, and increased prothrombotic and antifibrinolytic factors. Insulin resistance, caused by a complex of genetic and environmental influences, is now recognized not just as a mechanism contributing to hyperglycemia in type 2 diabetes, but also as an early metabolic abnormality that precedes the development of overt diabetes. The clinical definition of insulin resistance is the impaired ability of insulin (either endogenous or exogenous) to lower blood glucose. In some insulin-resistant individuals, insulin secretion will begin to deteriorate under chronic stress (glucose toxicity) and overt diabetes will result. If not, individuals will remain hyperinsulinemic, with perhaps some degree of glucose intolerance, together with other hallmarks of the IRS. The statistical correlation between hypertension and impaired glucose tolerance is clear, although the mechanism is not yet fully understood. Epidemiologic evidence of insulin resistance as an independent risk factor for arterosclerosis and coronary artery disease completed the evolving concept of IRS as the common soil for the development of both diabetes and coronary artery disease. No single laboratory test exists for diagnosis of IRS. Rather, IRS remains a clinically evident syndrome that can be suspected on the basis of physical and laboratory findings. Endothelial dysfunction occurs as a non-specific sign of insulin resistance syndrome.

Chronic treatment with external addition of pulses to the circulation stimulates endothelial release of nitric oxide, prostacyclin and t-PA thereby improving the insulin resistance syndrome in patients with type-2 diabetes mellitus.

Chronic Heart Failure

Introduction.

Organic nitrates are used in the management of patients with chronic heart failure as a means to reduce preload of the heart. But nitrate tolerance may develop when continuous administration of nitrates is utilized, particularly with transdermal nitroglycerin patches. This phenomenon does not occur with methods that externally add pulses to the circulation.

Drug Synergy and Externally Added Pulses

The production of endogenous nitric oxide, which regulates myocardial oxygen consumption, is decreased in heart failure. Angiotensin-converting enzyme (ACE) inhibitors and amlodipine, a calcium antagonist, increase kinin-mediated nitric oxide production in coronary microvessels. ACE inhibitors and amlodipine act synergistically to regulate myocardial oxygen consumption by modulating kinin-mediated nitric oxide release, and this combination of drugs is useful in treatment of chronic heart failure. Certain beta blockers also upregulate eNOS and provide additive or synergistic effects.

In chronic heart failure, the combination of ACE inhibitors, calcium antagonists, and certain beta blockers along with external addition of pulses to the circulation provide additive and possibly synergistic vasodilator, antiplatelet aggregation and antileukocyte adhesion actions to endothelial release of mediators, thereby improving manifestions of this entity.

Reperfusion Injury

This potentially lethal syndrome occurs after the affected area is reperfused in the presence of myocardial ischemia due to coronary artery disease or to cardiopulmonary resuscitation following cardiac arrest. It is due to influx of activated neutrophils into the affected area along with endothelial dysfunction. These cells liberate inflammatory mediators without the modulating effect of molecules such as nitric oxide released from the endothelium that are protective against such mediators. This phenomenon causes increased size of the infarcted area or myocardial dysfunction also known as "myocardial stunning."

In recent years, it has become recognized that preconditioning the heart before the reperfusion injury takes place may be cardioprotective. The early phase of preconditioning (PC) lasts 2 to 3 hours and protects against infarction but not against stunning and the late phase of PC lasts 3 to 4 days and protects against both infarction and stunning, suggesting that it may have greater clinical relevance. It is now clear that late PC is a polygenic phenomenon that requires the simultaneous activation of multiple stress-responsive genes. Chemical signals released by a sublethal ischemic stress (such as nitric oxide, reactive oxygen species, and adenosine) trigger a complex cascade of signaling events that includes the activation of protein kinase C, Src protein tyrosine kinases, and nuclear factor kappaB and culminates in increased synthesis of inducible NO synthase, cyclooxygenase-2, aldose reductase, Mn superoxide dismutase, and probably other cardioprotective proteins. An analogous sequence of events can be triggered by a variety of stimuli, such as heat stress, exercise, and cytokines. Thus, late PC appears to be a universal response of the heart to stress in general. Importantly, the cardioprotective effects of late PC can be reproduced pharmacologically with clinically relevant agents, e.g., NO donors, adenosine receptor agonists, endotoxin derivatives, or opioid receptor agonists, suggesting that this phenomenon might be exploited for therapeutic purposes. Preconditioning can be accomplished in high-risk patients with chronic external addition of pulses to the circulation for upregulation of eNOS as a means analogous to the cardioprotective role of exercise. In patients experiencing reperfusion injury, treatment with external addition of the pulses into the circulation during that period will upregulate eNOS in endothelial cells that are still functioning and ameliorate the injury. Further, since external addition of the pulses with the motion platform as mentioned in U.S. Pat. No. 6,155,976 (Reciprocating movement platform for shifting subject to and fro in headwards-footwards direction, Marvin A. Sackner, D. Michael Inman, William J. Meichner) also serves as a cardiopulmonary resuscitation device, this means of CPR also serves to prevent postperfusion injury during CPR since it enhances release of nitric oxide from the endothelium and endocardium.

Myocardial Hibernation

Ischemic myocardium does not inevitably undergo necrosis but rather can survive through downregulation of contractile function, ie, "hibernate." Upregulation of nitric oxide reduces myocardial oxygen consumption thereby improving regional myocardial function for any given level of myocardial blood flow, oxygen consumption and energetics. This preserves contractile cacium sensitivity during myocardial ischemia without effect on myocardial energetics. Thus, added pulses to the circulation are beneficial in the treatment of myocardial ischemia.

Systemic Hypertension

Obesity Related

The antihypertensive effect of aerobic exercise in obesity related hypertension is associated with improved vasodilatation. This is due to upregulation of nitric oxide and prostacyclin release from endothelium. The improved basal arterial tone after training can be attributed to the alleviation of hyperlipidemia and insulin resistance but hyperinsulinaemia per se may remain unaffected.

In obesity related hypertension, the antihypertensive effect of aerobic exercise is associated with improved vasodilation which is also accomplished by chronic treatment with external addition of pulses to the circulation; this upregulates endothelial release of nitric oxide and prostacyclin release thereby bringing about the same result albeit without reduction in body weight.

Renal Failure

Arterial stiffening is very pronounced in patients with renal failure and carotid artery stiffening is a powerful predictor of future cardiovascular mortality. Measures of arterial stiffening correlate much better with left ventricular mass in dialysis patients than do conventional measurements of brachial artery blood pressure. Arterial stiffness and endothelial dysfunction are well-correlated vascular abnormalities.

Chronic treatment with external addition of pulses to the circulation in patients with renal failure complicated by arterial stiffness upregulates endothelial release of nitric oxide, prostacyclin, and endothelial dependent hyperpolarizing factor, all of which diminish arterial stiffness.

Cerebrovascular Accidents

Atrial Fibrillation

Many elderly patients with recurrent intermittent AF have substantial rates of stroke and are likely benefit from anticoagulation. However, in such patients, anticoagulant therapy is complicated by a high incidence of internal bleeding.

Chronic treatment with external addition of pulses to the circulation has potential to prevent stroke in patients with atrial fibrillation because of upregulation of endothelial release of nitric oxide, prostacyclin, endothelial dependent hyperpolarizing factor and t-PA from endothelium, all of which have fibrinolytic properties.

Stroke

In patients in whom treatment with endothelial nitric oxide might be beneficial but where eNOS upregulation is not acutely possible because of acquired or genetic defects, external induction of pulses (motion platform) with analysis of the digital pulse wave provides a rapid, screening means to determine endothelial dependent vasodilation. This helps to make a decision as to whether it is best to pursue this approach or chose a nitric oxide donor drug with endothelial independent vasodilator properties. For example, in ischemic stroke following middle cerebral artery occlusion, nitric oxide released with eNOS limits the extent of the stroke. But if eNOS is absent, agents that upregulate or prolong its action are ineffective. Here a nitric oxide donor drug that has endothelial independent vasodilator properties should be administered.

L-arginine induces sustained cerebral blood flow increases in normal brain as well as in a marginally perfused brain region distal to arterial occlusions. L-arginine-induced increases in cerebral blood flow decrease cerebral infarction volume in both normotensive and hypertensive subjects.

External addition of pulses to the circulation increases cerebral blood flow through release of nitric oxide from vascular endothelium as well as prostacyclin and tissue plasminogen activator, all of which are effective in treating ischemic strokes.

Subarachnoid Hemorrhage

Low-dose transdermal nitroglycerin patches improve cerebral vasospasm after subarachnoid hemorrhage without significant alterations in systemic hemodynamics. Addition of pulses to the circulation by means of intraaortic balloon pumping improves cerebral blood flow in patients with cerebral vasospasm.

External addition of pulses to the circulation by releasing nitric oxide from vascular endothelium relieves cerebral vasospasm associated with subarachnoid hemorrhage.

Pulmonary Hypertension

Primary Pulmonary Hypertension

Compared to normal subjects, patients with primary pulmonary hypertension have raised levels of circulating endothelin-1, a vasoconstrictor mediator and a trend toward lower levels of nitric oxide.

External addition of pulses to the circulation by stimulating endothelial release of nitric oxide and prostacylin, both pulmonary vasodilators, and suppressing endothelin-1, bring pulmonary arterial pressures in primary pulmonary hypertension toward normal levels. Further, the release of t-PA helps prevent the complication of pulmonary arterial thrombosus.

Secondary Pulmonary Hypertension

Compared to normal subjects, patients with secondary pulmonary hypertension have raised levels of circulating endothelin-1, a vasoconstrictor mediator and a trend toward lower levels of nitric oxide.

External addition of pulses to the circulation by stimulating endothelial release of nitric oxide and prostacylin, both pulmonary vasodilators, and suppressing endothelin-1, bring pulmonary arterial pressures in seconday pulmonary hypertension toward normal levels.

Neonatal Pulmonary Hypertension

Increased oxygenation but more importantly increased pulmonary blood flow with increased shear stress induce eNOS gene expression and contribute to pulmonary vasodilation after birth through nitric oxide release. Genetic deficiency of eNOS is associated with failure to diminish the pulmonary hypertension present in fetal life and closure of the patent ductus arteriosis. Inhaled nitric oxide reduces the extent to which extracorporeal membrane oxygenation is needed in neonates with hypoxemic respiratory failure and pulmonary hypertension. However, prolonged use of inhaled nitric oxide may increase the intraavelolar activation of the coagulation system by increasing the pulmonary expression of tissue factor and thrombin. This phenomenon has been implicated in the pathogenesis of acute lung injury and would be considered an adverse effect of inhaled nitric oxide.

External addition of pulses to the circulation helps to restore eNOS in neonates with genetic deficiency of eNOS without the potential for injury as could be associated with inhaled nitric oxide therapy. Added pulses also release endothelial prostacylin, a mediator that both reduces pulmonary hypertension and promotes closure of the patent ductus arteriosus.

Bronchopulmonary Dysplasia

Severe bronchopulmonary dysplasia (BPD), which is associated with high mortality and morbidity, is thought to be the result of mechanical, inflammatory, and oxidant injury to the immature lung, and includes the development of pulmonary hypertension with vascular remodeling. There is increased pulmonary vascular smooth muscle and microvascular filtration pressure. This may relate to diminished eNOS and soluble guanylate cyclase in the pulmonary circulation. BPD has a component of endothelium dysfunction. Inhaled nitric oxide improves oxygenation in some infants with severe BPD allowing decreased FIO2 and ventilator support without evidence of adverse effects. However, the management of inhaled nitric oxide is extremely labor-intensive and without careful monitoring, toxic effects may occur.

External addition of pulses to the circulation upregulates endothelial release of nitric oxide and prostacyclin thereby alleviating the secondary pulmonary hypertension of bronchopulmonary dysplasia.

Pulmonary Embolism

Inhaled nitric oxide has rapidly reversible inhibitory effect on platelet aggregation after acute massive pulmonary embolism appears beneficial. It is also effective in lowering the pulmonary hypertension that complicates multiple small pulmonary emboli.

External addition of pulses to the circulation releases nitric oxide, prostacyclin, tissue plasminogen activator and endothelial dependent hyperpolarizing factor, all of which are beneficial in treatment of pulmonary embolism/pulmonary emboli and the complications. In addition, distribution of the added pulses through the circulation is independent of ventilation/perfusion mismatch that hamper effectiveness of inhaled nitric oxide Further, gaseous nitric oxide for inhalation is also more difficult to properly administer.

Portal Hypertension

Although excessive levels of nitric oxide appear to account for the vasodilation present in patients with cirrhosis and portal hypertension, administration of organic nitrates that release nitric oxide are effective in reducing portal hypertension and esophageal variceal bleeding. This paradox may relate to which NOS isoform contributing nitric oxide. In some patients, iNOS in polymorphonuclear leukocytes and monocytes is upregulated and in others eNOS in endothelium is upregulated. However, it appears that portal hypertension is related to downregulation of eNOS.

External addition of pulses to the circulation to upregulate eNOS in portal venous endothelium in conjunction with specific iNOS inhibitors has potential to be beneficial in treatment of portal hypertension and esophageal varices.

Renal Failure

Nitric oxide increases renal medullary blood flow and promotes excretion of sodium and water. External addition of pulses to the circulation through nitric oxide release from endothelium has a diuretic action in renal failure.

Venous Stasis

Prolonged bed rest or immobility causes venous stasis that may lead to thrombosis and possible pulmonary emboli. Intermittent treatment with added pulses to the circulation using the motion platform not only upregulates endothelial release of nitric oxide, prostacyclin and tissue plasminogen activator from venous endothelium but also increases venous return, all of which mitigate the risk of thrombosis since stasis of blood flow is prevented.

Deep Venous Thrombosis

In patients with spontaneous or recurrent deep vein thrombosis without known organic disease as the basis for the thrombosis and without known defects of antithrombin III, heparin cofactor II, protein C, or protein S, poor fibrinolytic response to 10 minutes of venous occlusion occurs in about 35% of such patients. Poor responders fall into two categories, 25% with deficient t-PA release who have a high risk for recurrent venous thrombosis, and 75% with increased PA inhibitor levels associated with hypertriglyceridemia.

Chronic treatment with external addition of pulses to the circulation that upregulates endothelial release of nitric oxide, prostacycline, and tissue plasminogen activator while suppressing tissue plasminogen inhibitor (Dai G, et al. An in vitro cell culture system to study the influence of external pneumatic compression on endothelial function. J. Vasc. Surg. 2000;32:977–87) is indicated in patients with spontaneous or recurrent deep venous thrombosis because such patients often are deficient in tissue plasminogen activator and have hypertriglyceridemia.

Peripheral Arterial Occlusive Disease

L-arginine treatment diminishes intermittent claudication of patients with peripheral arterial occlusive disease as evidenced by improvement of walking distance before experiencing calf pain.

Chronic treatment with external addition of pulses to the circulation in patients with peripheral arterial occlusive disease who have endothelial dysfunction restores such function by upregulating basal synthesis of nitric oxide, prostacyclin, and tissue plasmiogen activator and downregulating basal synthesis of endothelin-1 and tissue plasminogen inhibitor.

Shock

Hemorrhagic Shock

The manifestations of hemorrhagic shock are mainly due to two factors: (1) Excessive production of peroxynitrite that can initiate a wide range of toxic oxidative reactions, toxicities that are likely to play a role in the pathophysiology of hemorrhagic shock. Peroxynitrite is a potent trigger of DNA single strand breakage, with subsequent activation of the nuclear enzyme poly (ADP ribose) synthetase (PARS), leading to eventual severe energy depletion of the cells, and necrotic-type cell death. Pharmacological inhibition of PARS, with 3-aminobenzamide or 5-iodo-6-amino-1,2-benzopyrone, improves hemodynamic status and prolongs survival time in rodent and porcine models of severe hemorrhagic shock. (2) Upregulation of iNOS takes place during sustained shock. iNOS expressed during shock contributes to vascular decompensation. In addition, the presence of even low levels of iNOS at the time of resuscitation enhances the inflammatory response that follows the reperfusion state. Pharmacological inhibition of iNOS with N6(iminoethyl)-L-lysine or genetic inactivation of iNOS (iNOS knockout mice) attenuates the activation of the transcription factors nuclear factor kappa B (NFkappaB) and Signal Transducer and Activator of Transcription 3 (STAT3), and ameliorates the increases in interleukin-6 and G-CSF messenger RNA levels in the lungs and liver. Inhibition of iNOS results in a marked reduction of lung and liver injury produced by hemorrhagic shock. Thus, induced nitric oxide, in addition to being a "final common mediator" of hemorrhagic shock, is essential for the up-regulation of the inflammatory response in resuscitated hemorrhagic shock. Furthermore, a picture of a pathway is evolving that contributes to tissue damage both directly via the formation of peroxynitrite, with its associated toxicities, and indirectly through the amplification of the inflammatory response. A combined anti-inflammatory agent, mercaptoethylguanidine, which selectively inhibits iNOS and scavenges peroxynitrite, prevents the delayed vascular decompensation and the cellular energetic failure associated with late hemorrhagic shock.

The adjuvant use of L-arginine restores the depressed cardiac output and organ blood flow and decreased plasma levels of interleukin-6 in hemorrhagic fluid loss due to trauma. The effectiveness of L-NMMA as a pressor suggests that nitric oxide contributes to hypotension following hemorrhage. However, reversing hypotension with L-NMMA does not improve survival. In contrast, L-arginine does not cause further lowering of blood pressure and has significant survival benefit. This suggests a possible protective effect of nitric oxide after hemorrhage, perhaps by improving the distribution of capillary blood flow and/or by decreasing platelet aggregation and leukocyte adhesion within the microcirculation.

External addition of pulses to the circulation in conjunction with the administration of an iNOS inhibitor and scavenger of peroxynitrate, e.g., mercaptoethylguanidine, serves as a useful adjunct to fluid resuscitation by preventing the inflammatory consequences of hemorrhagic shock.

Septic Shock

NO can have both beneficial and detrimental effects on many organ systems in sepsis and attempts to nonselectively block all its actions may therefore not yield positive results on outcome. Both nitric oxide donors and inhibitors have been employed without success. Septic shock is characterized by systolic overloading of the right heart owing to pulmonary hypertension. Here nitric oxide relieves pulmonary hypertension but in the systemic arteries, nitric oxide causes a further unacceptable fall in systemic arterial pressure.

Bacterial endotoxin (LPS) releases many mediators such as interleukins, tumour necrosis factor, oxygen free radicals, toxic eicosanoids, platelet activating factor, and nitric oxide. LPS is a potent inducer of inducible nitric oxide synthase (iNOS). Large amounts of nitric oxide (made by iNOS) and peroxynitrite, among other factors, are responsible for the late phase of hypotension, vasoplegia, cellular suffocation, apoptosis, lactic acidosis and multiorgan failure in endotoxic shock. In lungs, nitric oxide released by eNOS plays a protective role against the pneumotoxic effects of LPS-released lipids such as thromboxane, leukotrienes and PAF. This is why selective iNOS inhibitors like aminoguanidine or thiourea derivatives might be preferred over nonselective NOS inhibitors for the treatment of septic shock. However, since iNOS-derived nitric oxide seems to have more than just a destructive action, the selective iNOS inhibition may be not as beneficial as expected. Accordingly, administration of nitric oxide through external septic shock might be a complementary treatment to the use of NOS inhibitors.

The combination of a selective inhibitor of iNOS plus stimulation of eNOS through external added pulses to the circulation in order to lower pulmonary vascular resistance provides a basis for treatment of septic shock. Further, nitric oxide in the blood stream inhibits formation of Interleukin-6, a cytokine that is responsible for many of the manifestations of septic shock.

Raynaud's Phenomenon

Raynaud's phenomenon is a condition marked by intense vasoconstriction of digital arteries in response to cold exposure as well as emotional stress. These patients have endothelial dysfunction.

External addition of pulses to the circulation to release both nitric oxide and prostacylin constitute treatment for this disorder.

Dysmenorrhea

Nitroglycerin transdermal patches relieve dysmenorrhea.
External addition of pulses to the circulation by releasing endothelial nitric oxide relieves the symptoms of dysmenorrhea.

Pregnancy

Preeclampsia

Increase in intraluminal flow leads to dilatation of isolated myometrial arteries from healthy gravid women, whereas flow-mediated dilatation is absent in arteries from gravid patients with preeclampsia. Thus, preeclamptic women have endothelial dysfunction and dysfunction of the nitric oxide-L-arginine-pathway. Transdermal administration of nitroglycerin appears to be beneficial in patients with preeclampsia who have increased uteroplacental impedance. Although L-arginine administration to non-preeclamptic, pregnant women causes increased nitric oxide production and hypotension, patients with preeclampsia may benefit from L-arginine because hypertensive symptoms are improved.

Chronic treatment with external addition of pulses to the circulation to promote endothelial release of nitric oxide relieves the manifestations of preeclampsia.

Preterm Cervical Dilatation

Transdermal nitroglycerin patches delay delivery from pregnant women with premature cervical dilatation. The only maternal side effect is headache. But it is well known that prolonged usage of transdermal nitroglycerin is ineffectiveness related to drug tolerance. The latter does not occur in the therapeutic usage of added pulses that release nitric oxide from vascular endothelium. Nor are added pulses associated with high prevalence of headache as with nitroglycerin.

External addition of pulses to the circulation to promote endothelial release of nitric oxide in patients with preterm cervical dilatation appropriately delays onset of labor.

Neurologic Diseases

Alzheimer's Disease

Alzheimer's disease (AD)+cerebrovascular disease may account for 20–40% of clinical AD. Constitutively reduced cerebrovascular eNOS expression and nitric oxide production as a result of cerebrovascular atherosclerosis could also lead to cerebral hypoperfusion due to impaired vasodilator responses, and diminished capacity to remove respiratory waste products and toxins from the extracellular space due to reduced capillary permeability. Furthermore, ultrastructural abnormalities of cerebral capillaries are causally related to decreased cerebral blood flow and create a condition that favors neurodegenerative mechanisms including the development of dementias such as Alzheimer's disease. Diminished cerebral blood flow and beta-amyloid plaques that accumulate in the brain are present in Alzheimer's disease. Interleukin-6, an inflammatory cytokine promotes the formation of beta-amyloid. IL-6 is detectable in a significant proportion of plaques in the brains of demented patients. In AD patients, IL-6 was found in diffuse plaques in a significant higher ratio as would have been expected from a random distribution of IL-6 among all plaque types. This suggests that IL-6 may precede neuritic changes, and that immunological mechanism may be involved both in the transformation from diffuse to neuritic plaques in AD and in the development of dementia.

From review of the literature, it appears that disorders associated with deposition of insoluble β-amyloid aggegates reflect a $NO/O_2^-$ imbalance. It has been stated that treatments might include NO supplementation with $O_2^-$ resistant donors or the elimination of $O_2^-$ with either NAP(P)H oxidase inhibitors or SOD mimetics (an extracellular SOD mimetic might be best). Scavengers of $OONO^-$, the oxidizing product of $NO/O_2^-$ could be beneficial. Alternatively, antioxidants such as vitamin E, which both preserves endothelial function and attenuates the neurotoxicity of P-amyoid could be tried. A deficit of endothelial-derived nitric oxide might contribute to the clinical syndrome of Alzheimer's disease, recalling that NO might be also involved in memory. Beta-amyloid interacts with endothelial cells to produce an excess of superoxide radicals that scavenge endothelium-derived nitric oxide. Thus, increasing the level of circulating nitric oxide through upregulation of eNOS by external addition of pulses might ameliorate Alzheimer's disease as well as improve memory in patients with the so-called "senior moment."

The monoamine oxidase-B (MAO-B) inhibitor L-deprenyl (Selegiline) is effective in treating Parkinson's disease and possibly Alzheimer's disease, with a concomitant extension of life span. The therapeutic efficacy of L-deprenyl may involve actions other than the inhibition of the enzyme MAO-B. Stimulation of nitric oxide (NO) production could be central to the action of the drug. L-Deprenyl induced rapid increases in NO production in brain tissue and cerebral blood vessels. In vitro or in vivo application of L-deprenyl produced vasodilatation. The drug also protects the vascular endothelium from the toxic effects of amyloid-beta peptide. Because NO modulates activities including cerebral blood flow and memory, and reduced NO -production has been observed in the Alzheimer's Disease brain, stimulation of NO production by L-deprenyl could contribute to the enhancement of cognitive function in Alzheimer's Disease. MAO-B inhibitors are unique in that they exert protective effects on both vascular and neuronal tissue and thus warrant further consideration in the treatment of vascular and neurodegenerative diseases associated with aging. They might be used in conjunction with external addition of pulses to the circulation to provide an additive or synergistic effect on cognitive function.

Measurement of the nitric oxide degradation products, nitrite and nitrate in cerebrospinal fluid of Alzheimer's disease reveals significantly decreased nitrate but not nitrite levels compared to controls. This suggests a decreased nitric oxide production in the central nervous system and makes another case for long-term treatment with external addition of pulses into the circulation as a means to increase nitric oxide release from endothelium.

Estrogen deficiency, hyperinsulinemia, type II diabetes, atherosclerosis, and a past history of elevated blood pressure may be associated with increased risk of Alzheimer's disease (AD). Common to all of these risk factors is a diminished capacity of vascular endothelium to generate nitric oxide (NO). Vascular NO has the potential to enhance the membrane polarization of cerebral neurons by increasing the open probability of calcium-activated potassium channels; this may protect neurons from the excessive calcium influx, potentiated by beta-amyloid peptides that are thought to mediate neuronal damage in AD. The possibility that NO/cyclic guanosine 3', 5'-phosphate (cGMP) may modulate the synthesis or processing of the amyloid precursor protein, also merits evaluation. The neurodegenerative plaques of Alzheimer's disease (AD) are characterized by a self-sustaining acute-phase reaction in which both interleukin-1 (IL-1) and interleukin-6 (IL-6) are upregulated. The fact that IL-6 is detectable in early stage diffuse plaques encourages the speculation that the acute-phase process is crucial to the pathogenesis of AD. The epidemiological association of AD with estrogen deficiency, as well as with various disorders characterized by vascular endotheliopathy, suggest a protective role for vascular nitric oxide (NO). NO has an autocrine anti-inflammatory impact on endothelium, owing in part to antagonism of NF-kappaB activity; since induction of IL-6 is dependent on NF-kappaB, this may explain recent evidence that NO inhibits macrophage IL-6 production. It is reasonable to postulate that, analogously, cerebrovascular NO decreases IL-6 production in the brain. Vascular NO may also have direct neuroprotective activity.

Estrogen that acts through the nitric oxide L-arginine pathway, prevents vascular deposition of A beta, endothelial and vessel wall disruption with plasma leakage, platelet and mast cell activation, and characteristic features of an inflammatory reaction: adhesion and transmigration of leukocytes. The vascular actions of estrogen include: improved lipid profile, enhancement of nitric oxide-mediated endothelial function, increased vasodilation and blood flow, inhibition of smooth muscle proliferation and platelet adhesiveness.

With progression of Alzheimer's disease, impaired frontal lobe blood flow occurs; this appears to be an important factor causing postural and gait disturbance in the late stage of disease.

Chronic treatment with external addition of pulses to the circulation in fully developed Alzheimer's disease or in patients with increasingly impaired cognitive function or memory deficits through release of endothelial nitric oxide increases cerebral blood flow, improves cerebral vessel endothelial function and suppresses formation of Interleukin-6, thereby potentially treating and preventing this disease. This treatment may be more effective when combined with estrogens and specific iNOS and nNOS inhibitors, such as the monoamine oxidase-B inhibitor L-deprenyl. The added pulses to the circulation serves both as preventative and therapeutic measures in Alzheimer's disease and in patients with increasingly impaired cognitive function or memory deficits.

Parkinson's Disease

Ultrastructural abnormalities of cerebral capillaries are causally related to decreased cerebral blood flow and create a condition that favors neurodegenerative mechanisms including the development of dementias such as Parkinson's disease. The nitric oxide degradation products, nitrite and nitrate in cerebrospinal fluid of Parkinson's disease indicate significantly decreased nitrate but not nitrite levels compared to controls. This suggests a decreased nitric oxide production in the central nervous system and makes another case for long-term treatment with external addition of pulses into the circulation as a means to increase nitric oxide release from endothelium.

The monoamine oxidase-B inhibitor L-deprenyl (Selegiline) is effective in treating Parkinson's disease and possibly Alzheimer's disease. The neuroprotective property of L-deprenyl may be unrelated to the inhibition of monoamine oxidase-B. Since nitric oxide (NO) modulates activities including cerebral blood flow and memory, the effect of L-deprenyl on nitric oxide was examined. L-Deprenyl induced rapid increases in NO production in brain tissue and cerebral vessels. Vasodilation was produced by endothelial NO-dependent as well as NO-independent mechanisms in cerebral vessels. The drug also protects the vascular endothelium from the toxic effects of amyloid-beta peptide.

Chronic treatment with external addition of pulses to the circulation in Parkinson's disease through release of endothelial nitric oxide increases cerebral blood flow, and improves cerebral vessel endothelial function thereby potentially treating and preventing this disease. This treatment may be more effective when combined with specific iNOS and nNOS inhibitors such as the monoamine oxidase-B inhibitor, L-deprenyl.

Multiple Sclerosis

Plasma nitrates levels have been reported as either normal or low in multiple sclerosis and cerebrospinal fluid nitrates normal. In patients with low plasma nitrate values, these value increased during successful treatment of clinical exacerbations but did not change when treatment was unsuccessful.

Chronic treatment with external addition of pulses to the circulation has potential to provide benefits in multiple sclerosis through endothelial release of nitric oxide promoting vasodilation in areas of the central nervous system. This treatment may be more effective when combined with specific iNOS and nNOS inhibitors.

Traumatic Brain Injury

Traumatic brain injury is associated with upregulation of all three forms of nitric oxide synthase. The expression of iNOS (inducible NOS) in polymorphonuclear cells and macrophages, cells that invade injured brain tissue, is a therapeutic target in brain contusions.

Neural NOS (nNOS) is unexpectedly present in these cells as well. Thus, selective NOS inhibitors for the neuronal and inducible forms of NOS are indicated in traumatic brain injuries.

External addition of pulses to the circulation has potential to benefit this disease through endothelial release of nitric oxide and its effect of increasing cerebral blood flow to damaged areas of the central nervous system. This treatment may be more effective when combined with specific iNOS and nNOS inhibitors to limit tissue damage and restore diminished response to hypercapnia associated with brain trauma.

Psychiatric Diseases

Short-term exercise training in patients with depressive reactions improves this condition. Further, brain stem blood flow is reduced in some cases of organic depressive reaction. Since external addition of pulses to the circulation markedly increase brain stem blood flow in anesthetized animals due to nitric oxide release from vascular endothelium, this technology has potential to treat depressive reactions. In addition, evidence has been reported that brain-derived neurotrophic factor (BDNF) ameliorates depressive reactions. Endothelial cells are a source of BDNF but it is unclear whether this mediator is expressed by increases in tangential or circumferential shear stress. Chronic addition of external pulses to the circulation is equivalent to exercise in terms of improvement of endothelial function. Therefore, other mental conditions that show psychological improvement with exercise ought to improve with external addition of pulses to the circulation. Beneficial psychological effects of exercise are best documented for mild to moderate forms of unipolar depression and chronic fatigue syndrome; in these disorders, exercise is an alternative to traditional forms of treatment. A therapeutic effect may also be achieved in panic and generalised anxiety disorder, schizophrenia, conversion and somatoform pain disorder, and alcohol abuse and dependence.

External addition of pulses to the circulation has potential to improve depressive reactions, chronic fatigue syndrome, panic and generalised anxiety disorder, schizophrenia, conversion and somatoform pain disorder, and alcohol abuse and dependence.

Pain Management

External addition of pulses to the circulation to promote endothelial release of nitric oxide acts synergistically with narcotics in the relief of cancer pain. Nitric oxide may also prevent morphine tolerance.

Sleep

In animal models, nitric oxide appears to increase NREM sleep as evidenced by suppression with L-NAME, an agent that inhibits nitric oxide release from eNOS. There are variable effects on REM sleep. Sleep is under the control of circadian and homeostatic regulatory processes. The homeostastic component of NREM serves to provide a compensatory increase in NREM after sleep loss. Its existence can be demonstrated by sleep deprivation studies and is independent of circadian influences. Nitric oxide plays a role as a signaling molecule in the homeostatic regulation of NREM.

Acute and chronic treatment with external addition of pulses to the circulation to promote endothelial release of nitric oxide promotes NREM sleep particularly in the presence of sleep deprivation.

Glaucoma and other Eye Diseases

In glaucoma patients with wide and narrow anterior chamber angle, nitroglycerin causes a fall in intraocular pressure within 30 minutes after administration.

Intraocular pressure depends upon rate of aqueous production and reflects the pressure head necessary to overcome the intrinsic tissue resistance of the outflow system to drain sufficient fluid out of the eye. Most of the resistance to outflow resides in the trabecular meshwork and it is here that the lesion associated with pathologic increases in intraocular pressure first manifests. The trabecular meshwork acts like a valve by distending when required to drain large amounts of fluid and narrowing down when drainage rate is low. Meshwork cells have many characteristics in common with smooth muscle cells and they contract with cholinergic agonists but relax with nitric oxide donors. Much of the nitric oxide activity, which is due to eNOS in the outflow system, is associated with the meshwork tissue involved in maintenance of intraocular pressure. Estrogen, that acts through the nitric oxide-L-arrginine pathway, cause vasodilation with lowering of s intraocular pressure. Deficiency of nitric oxide or nitric oxide containing cells occurs in primary open-angle glaucoma.

In the human ophthalmic artery, endothelium-derived nitric oxide and endothelin 1 are very potent modulators of vascular tone, suggesting that they play an important role in the regulation of local blood flow in the eye. Hence, endothelium dysfunction may represent a new pathogenic mechanism in disease states associated with altered blood flow to the eye, such as diabetic retinopathy, macular degeneration, hypertensive retinopathy, and some forms of low-tension glaucoma.

Chronic treatment with external addition of pulses to the circulation to upregulate eNOS in the trabecular meshwork of the eye and the ophthalmic artery has potential to ameliorate glaucoma, diabetic retinopathy, macular degeneration and hypertensive retinopathy.

Ear Diseases

Sudden Deafness and Meniere's Disease

Reduced cochlear blood flow has been implicated in various pathologies of the inner ear, including sudden deafness, noise-induced hearing loss and Meniere's disease. The aim of some current therapeutic regimens to treat these conditions is to increase cochlear blood flow thereby improve oxygenation of the inner ear tissues. Most vasodilating agents in clinical use do not have specific experimental evidence to support their effects on cochlear blood flow. Topical administration of sodium nitroprusside, a nitric oxide donor drug, is the most effective vasodilator compared to several non-organic nitrate vasodilators.

Chronic treatment with external addition of pulses to the circulation to upregulate eNOS in the cochlear arterial endothelium of the ear has potential to ameliorate sudden deafness and Meniere's disease.

Lymphedema

In chronic heart failure, as venous pressure increases, so does lymphatic pressure. Although lymph flow may continue, the flow is decreased, contributing to central or peripheral edema. Disorders of the lymphatic circulation can be divided into anatomical and functional. The anatomic include congenital lymphedema (Milroy's) and lymphedema precox (before 35 years) and lymphedema tarda (after 35 years), lymphangitis, neoplastic invasion, irradiation, and posttraumatic. Functional diseases include chronic heart failure, lymphangiospasm, causalgia among others that produce low lymph flow and edema. High output heart failure, cirrhosis and renal failure may be associated with high lymph flow and edema. In addition, lymphedema may be surgically induced by resection of lymph nodes and lymph channels in the treatment of neoplastic disorders such as breast cancer and melanoma. For the latter, localized compressive pumps are currently used for mechanically increasing lymphatic drainage.

Chronic treatment with external addition of pulses to the body's fluid channels has potential to treat diseases associated with anatomically impaired lymphatic drainage such as Milroy's lymphedema, lymphedema precox, lymphedema tarda, lymphangitis, neoplastic lymphatic invasion, irradiation induced narrowing of lymphatic channels, post-surgical resection of lymph nodes and lymph channels, and, post-traumatic injury to lymphatic channels or functionally impaired lymphatic drainage that occurs in chronic heart failure, lymphangiospasm and causalgia. This is because the added pulses stimulate lymphatic endothelium to release nitric oxide as well as other mediators that promote lymphatic drainage. Monitoring of change in extremity volume can be assessed with limb inductive plethysmography that reflects changes in cross-sectional area of the arms or legs.

Adult Respiratory Distress Syndrome

Inhaled nitric oxide reduces pulmonary hypertension and may increase arterial oxygen tension in Adult Respiratory Distress Syndrome (ARDS). The latter is achieved by improved matching of ventilation and perfusion. Responses to inhaled nitric oxide (iNO) as evidenced by improvements in oxygenation are variable. This is because the effect is a function of ventilation/perfusion inequalities. If iNO is preferentially distributed to lung regions that are well perfused, then its effects on matching ventilation to perfusion in other lung regions will not occur. Thus oxygenation will not improve because of continuing ventilation/perfusion mismatch.

External addition of pulses to the circulation to release nitric oxide and supress endothelin-1 from pulmonary vascular endothelium reduces pulmonary hypertension associated with Adult Respiratory Distress Syndrome. The vascular distribution of these mediators is independent of mismatched ventilation to perfusion ratios and more effective than the currently advocated treatment of this condition with inhaled nitric oxide that has such limitations.

Meconium Aspiration Syndrome

Meconium aspiration syndrome is a complication of birth in newborns who aspirated meconium, their own sterile fecal material into the lung during labor. In experimental meconium aspiration syndrome accomplished by instilling meconium into the trachea of anesthetized animals, after treatment with surfactant, administration of inhaled nitric oxide improves oxygenation without significantly decreasing pulmonary arterial pressure. Increase in oxygenation is secondary to improvement of ventilation/perfusion mismatch, since the primary etiology of hypoxemia in this model is a combination of parenchymal lung disease and pulmonary hypertension.

In contrast to the failure to reverse pulmonary hypertension with inhaled nitric oxide, externally added pulses to the circulation by means of a motion platform completely reversed pulmonary hypertension in an animal as reported by Adams et al. (Hemodynamic effects of periodic Gz acceleration in meconium aspiration in pigs. J. Appl. Physiol. 2000; 89:2447–2452). The hemodynamic effects of periodic acceleration in the spinal axis (pGz) induced with a motion platform were studied in a piglet model of meconium aspiration. Animals were anesthetized, paralyzed, intubated, and supported by conventional mechanical ventilation (CMV). Thirty minutes after tracheal instillation of meconium solution (6 ml/kg), either CMV was continued in one group or pGz was initiated in another. Changes in systemic and pulmonary hemodynamics, and arterial blood gases were tracked for two hours after aspiration. Thermodilution cardiac output and heart rate were not significantly different after meconium aspiration in the pGz group relative to the CMV controls. Aortic pressure and systemic vascular resistance was significantly lower (~30%) after meconium aspiration in pGz animals relative to CMV animals. Pulmonary artery pressure and pulmonary vascular resistance were also significantly lower by 100% after aspiration of meconium in the NIMV animals compared to the CMV controls. Meconium aspiration significantly decreased total respiratory compliance and increased total respiratory resistance in both CMV and pGz animals but such alterations did not differ between the two groups. Periodic acceleration in the spinal axis decreased systemic and pulmonary vascular resistance in piglets after meconium aspiration. The different effects on reversal of pulmonary hypertension between inhaled nitric oxide and pGz may relate to the fact that 1) added pulses to the circulation cause release of both nitric oxide and prostacyclin from endothelium that act synergistically as pulmonary vasodilators and 2) superior distribution of mediators to vasculature than inhaled nitric oxide whose distribution depends upon ventilation/perfusion ratios.

External addition of pulses to the circulation to release nitric oxide and supress endothelin-1 from pulmonary vascular endothelium reduces pulmonary hypertension associated with meconium aspiration syndrome. The vascular distribution of these mediators is independent of mismatched ventilation to perfusion ratios and more effective than the currently advocated treatment with inhaled nitric oxide that has such limitations.

Bone, Joint and Muscle Diseases

Osteoporosis

In osteoporosis, upregulation of nitric oxide slows bone remodeling and bone loss. Because nitroglycerin and other nitrates increase nitric oxide levels, organic nitrates administered to patients with osteoporosis produce greater bone mineral density and decreased risk of fracture. Estrogen deficiency is another important factors in the pathogenesis of osteoporosis. The major effect of estrogen is to inhibit osteoclastic bone resorption. It has been found that estrogen stimulates eNOS RNA and eNOS activity in cultured human osteoblasts. Taken together with other work indicating that anabolic effects of estrogen on bone are blocked by a NOS inhibitor, modulation of the estrogen-nitric oxide pathway represents an approach to postmenopausal osteoporosis. Since the protective effect of estrogens against bone loss is mediated through nitric oxide, the bone loss associated with ovariectomy is counteracted by nitric oxide. Further, nitric oxide is also effective in corticostroid induced bone loss.

Chronic treatment with external added pulses to the circulation that also are transmitted to fluid channels of bone stimulates nitric oxide release from osteoblasts. Activation of osteoblasts leads to increase in bone mineral density and diminished risk to bone fracture.

Fracture Repair and Prevention

Increased eNOS in bone blood vessels is likely to mediate the increased blood flow during fracture healing. eNOS expression in osteocytes may occur in response to changes in either mechanical or local fluid shear stress. The finding that eNOS is increased and iNOS reduced in early healing of fractures may be important in their successful repair. If nitric oxide release is impaired because of hypertension, diabetes, atherosclerosis, hypercholestrolemia, etc., then the initial maximum vasodilation, a necessary component of early fracture healing, will be blunted or not take place with subsequent delayed fracture healing. Further, nitric oxide upregulation in osteoblasts that promotes new bone formation acts to prevent fractures, notably hip fractures in elderly patients.

Chronic treatment with added pulses to the circulation to release endothelial nitric oxide from bone blood vessels and osteoblasts in bone fractures prevents delayed healing and speeds up repair.

Rheumatoid and Juvenile Arthritis

The inflammatory process in rheumatoid arthritis and juvenile arthritis is marked by upregulation of iNOS from Interleukin-1 and excessive production of Interleukin-6. The latter is suppressed by nitric oxide.

Chronic treatment with external addition of pulses to the circulation causes release of nitric oxide and prostacyclin from vascular endothelium thereby suppressing the inflammatory response in rheumatoid and juvenile arthritis. Treatment with specific iNOS inhibitors further suppresses the inflammatory process.

Osteoarthritis

In osteoarthitis, metalloproteases in cartilage and production of Interleukin-1beta by synovium play a major role in the pathophysiology of OA structural changes. L-NIL, an inhibitor of iNOS attenuates the progression of experimental osteoarthritis. Nitroglycerin ointment, spread over the surface of joints associated with painful osteoarthritis relieves the pain.

Chronic treatment with external addition of pulses to the circulation causes release of nitric oxide and prostacyclin from vascular endothelium thereby suppressing the inflammatory response and relieving pain in osteoarthritis. Treatment with specific iNOS inhibitors further suppresses the inflammatory process.

Fibromyalgia

Fibromyalgia is a disorder characterized by diffuse widespread musculoskeletal aching and stiffness and multiple tender points. There is a positive effect of aerobic endurance exercise on fitness and well-being in patients with this disorder.

Chronic treatment with external addition of pulses to the circulation causes release of nitric oxide and prostacyclin from vascular endothelium thereby providing analogous benefits to exercise in fibromyalgia.

Wound Healing eNOS plays a significant role in facilitating wound repair and growth factor-stimulated angiogenesis. Nitric oxide is an important regulator of wound collagen accumulation and may directly or through the release of other mediators affect collagen synthesis or collagen breakdown in the wound.

Chronic treatment with external addition of pulses to the circulation increases endothelial release of nitric oxide thereby facilitatating wound healing through increased blood flow and laying down of reparative wound collagen.

Bed Sores

Endothelial dysfunction predisposes patients to develop bed sores during periods of intercurrent illness.

Chronic treatment with external addition of pulses to the circulation increases endothelial release of nitric oxide thereby facilitatating bed sore healing through increased blood flow.

Anal Fissure

Topical nitroglycerin provides rapid, sustained relief of pain in patients with anal fissure. Over two-thirds of patients treated in this way avoided surgery which would otherwise have been required for healing.

Chronic treatment with external addition of pulses to the circulation stimulates endothelial release of nitric oxide that provides both relief of pain in anal fissure as well as facilitated healing.

Tendon Healing

The enzyme eNOS that converts L-arginine to nitric oxide is upregulated in tendon healing. Its inhibition with L-NAME delays tendon healing.

Chronic treatment with external addition of pulses to the circulation by causing endothelial release of nitric oxide facilitates tendon healing.

Acute Gastric Injury

Endogenous nitric oxide through upregulation of eNOS contributes to the healing of acute gastric injury by mediating the mucosal hyperemic responses associated with acid back-diffusion and by facilitating acid disposal in the damaged mucosa.

HIV-1 Infection

Nitric oxide may have a role in the treatment of AIDS by inhibiting acute infection, reactivating latent virus, or both. Evidence suggests that nitric oxide may regulate HIV-1 replication by affecting the sulphydryl redox state. In this respect, it has been demonstrated that nitric oxide donors inactivate the HIV-1-encoded protease and reverse transcriptase in vitro. Further, viral and host nitric oxide targets may be envisaged. Although no data are available on the anti-HIV-effect of NO in vivo, NO-releasing drugs, clinically used in the treatment of cardiovascular disorders, may represent a novel class of molecules for decreasing virus replication.

Chronic treatment with external addition of pulses to the circulation to release endothelial nitric oxide has potential to aid in the treatment of HIV-1 infection.

Erectile Dysfunction

A basal level of NO synthesis is required for activation and relaxation of the corporeal smooth muscle. Activation of eNOS to release nitric oxide from endothelium is a means to achieve penile erection. Long-term treatment with external counterpulsation, a technology that adds a pulse in diastole to the naturally systolic pulse of the vascular circulation improves erectile dysfunction. Since external counterpulsation liberates nitric oxide from vascular endothelium, other methods that add pulses to the circulation should also be effective. Further, a higher frequency of added pulses with varied intensity to be tuned according to tests of efficacy of nitric oxide released promises greater effectiveness of treatment.

Nitric oxide promotes erection in probably by mediating filling of the corpora cavernosa. Nitric oxide may also inhibit seminal emission probably by decreasing sympathetic nervous system activity. This may help prevent premature ejaculation.

Chronic treatment with external addition of pulses to the circulation to upregulate eNOS and and prostacyclin synthesis in endothelium is effective in erectile dysfunction.

Microgravity

Effects

Muscle sympathetic nerve activity (MSNA) measured with microneurography, plasma nitrite/nitrate concentrations, and leg vascular resistance by venous occlusion plethysmography were assessed in healthy male volunteers before and after 14 days of 6° head-down bed rest (HDBR), the ground-based analogue of microgravity. MSNA increased, while plasma nitrite/nitrate concentrations decreased after HDBR. A significant positive correlation observed between MSNA and plasma nitrite/nitrate concentrations before HDBR disappeared after HDBR. Leg vascular resistance increased after HDBR. Thus, an imbalance between sympathetic vasoconstrictor traffic and NO release appears to contribute to elevated peripheral vascular resistance following HDBR. Further, this study suggests that vascular endothelium releases less nitric oxide in microgravity.

In microgravity, bone and muscle loss occurs due to deficient nitric oxide production. Gravity upregulates the basal activity of eNOS to release nitric oxide that acts upon osteoblasts. The loss of stimuli for nitric oxide production and release causes bone and muscle wasting in microgravity. Nitric oxide activates osteoblasts to make new bone and depresses activity of osteoclasts to resorb bone. Skeletal muscle is improved by nitric oxide through its effect on supplying blood borne nutrients to muscle tissue.

Chronic treatment with external addition of pulses to the circulation in microgravity relieves the bone and skeletal muscle loss associated with space flight by upregulating eNOS.

Exercise

Exercise represents the primary countermeasure in spaceflight to maintain or restore maximal aerobic capacity, musculoskeletal structure, and orthostatic function. However, no single exercise or combination of prescriptions has proven entirely effective in restoring cardiovascular and musculoskeletal functions to preflight levels following prolonged spaceflight.

Prolonged daily exercise presently used during spacefight is costly and drains life-support material. For example, the average daily exercise metabolic cost of 725 kcal during Russian missions represents about 24% of the total caloric intake of 3,150 kcal. If exercise time and ensuing energy costs could be halved, savings over a 6-month mission would be enough to support another crewmember with an additional 27 days of food, 23 days of water, and 13 days of oxygen. This issue will become critical on longer interplanetary flights. Time-intensive flight-exercise protocols, which can require as much as 2 hours per day, attenuate crewmembers' motivation.

Exercise methods currently being used in microgravity include: 1) cycle ergometer—weight 45 kg, 2) treadmill with resistance harness—weight 17 kg, and 3) isometric strength training devices. None have been successful in preventing bone and muscle loss and cardiac deconditioning.

In microgravity, external addition of pulses to the circulation to release nitric oxide and to act as a surrogate for aerobic exercise occupies less time and produces minimal change in oxygen consumption. It addresses the economic concerns of spaceflight. Further, added pulses mitigate bone loss by upregulating eNOS in osteoblasts. The addition of pulses could be accomplished with the motion platform or a pulsating garment.

In microgravity, treadmill exercise using a graded lower-body compression suit and 100 mm Hg lower body negative pressure provides equivalent or greater physiologic stress than similar upright exercise on Earth. It has been postulated that exercise within a lower body negative pressure chamber may provide a cost-effective and simple countermeasure to maintain the cardiovascular and neuro-musculoskeletal systems of astronauts during long-duration flight.

External addition of pulses from an air reservoir to the lower body negative compression chamber in order to stimulate endothelium and osteoblasts has potential to make this exercise countermeasure more effective.

Cancer

General Tumor Treatment

Nitric oxide donors inhibit angiogenesis, tumor growth and metastases in some animal tumor models.

Chronic treatment with external addition of external pulses to the circulation by increasing endothelial release of nitric oxide is effective in inhibiting growth of certain tumors.

Prostate Cancer

Prostate cancers have a high number of endothelin A receptors. These receptors mediate vasoconstriction asnd cell proliferation through endothelin-1. In osteoblastic tumor models, new bone formation is increased by endothelin-1 overexpression and decreased by endothelin A receptor blockade. The effectiveness of estrogens in treatment of osteoblastic prostatic bone metastasis has long been recognized. It has been found that estrogens increase levels of eNOS in human prostate cancer cells.

Since nitric oxide produced by eNOS inhibits endothelin 1, chronic treatment with external addition of external pulses to the circulation by increasing endothelial release of nitric oxide should be an effective treatment of prostatic cancers and possibly also be preventative.

Synergism with Chemotherapeutic Drugs

A major emphasis in cancer therapy research is finding mechanisms to enhance the effectiveness of clinically used chemotherapeutic agents. The flux of nitric oxide, as well as the amount of eNOS, is important in the NO-mediated enhancement of cisplatin cytotoxicity.

Chronic treatment with external addition of pulses to the circulation by releasing endothelial nitric oxide synergistically potentiates the chemotherapeutic effects of cisplatin.

Organ Preservation for Transplantation

Pulsatile perfusion of kidneys to be transplanted together with addition of PGE1 to perfusate is superior to cold storage in terms of subsequent graft function.

Inhaled nitric oxide and pentoxiphllline, a phosphodiesterase inhibitor that helps to preserves eNOS activity diminish allograft lung graft rejection after transplantation.

Nitric oxide diminishes myocardial oxygen consumption and in a heart deprived of blood supply can cause the heart to go into a state of hibernation.

External addition of pulses to the circulation of a prospective donor of organ(s) for transplantation helps to preserve such organs after death since as a result of endothelial release of nitric oxide, prostacyclin, and tissue plasminogen activator and suppression of endothelin-1 and tissue plasmiogen inhibitor that may place such organs into a state of hibernation.

Release of Prostacyclin

Pulmonary Hypertension

Nebulized prostacyclin appears to be more effective at reducing pulmonary artery pressure in patients with primary and secondary pulmonary hypertension than intravenous prostacyclin and inhaled nitric oxide. Further, treatment with inhaled nitric oxide has potential toxicity over the long-term. Prolonged use of inhaled nitric oxide may increase the intraavelolar activation of the coagulation system by increasing the pulmonary expressiom of tissue factor and thrombin. Activation of the coagulation system with enhanced thrombin generation in the lung has been implicated in the pathogenesis of acute lung injury.

Elevated pulmonary vascular resistance is a risk factor in heart transplantation and reversibility of high pulmonary vascular resistance is evaluated preoperatively in potential recipients using i.v. vasodilators or inhaled nitric oxide. Both inhaled nitric oxide and inhaled prostacyclin reduce mean pulmonary artery pressure and pulmonary vascular resistance. Other hemodynamic variables, including the systemic blood pressure, are unaffected by these agents. Inhaled prostacyclin induces a selective pulmonary vasodilation that is comparable to the effect of inhaled nitric oxide. Major advantages with inhaled prostacyclin are its lack of toxic reactions and easy administration as compared with the potentially toxic nitric oxide requiring more complicated delivery systems. Aerosolization of a prostacyclin analog, Iloprost, is more potent than inhaled nitric oxide in reducing pulmonary arterial pressure in patients with primary pulmonary hypertension.

Combined administration of inhaled nitric oxide and beraprost sodium, an oral prostacyclin analogue, results in a more intense decrease in pulmonary vascular resistance than nitric oxide given alone without serious systemic hypotension.

External addition of pulses to the circulation releases nitric oxide, prostacyclin and t-PA from endothelium, all of which are effective in treatment of both primary and secondary pulmonary hypertension.

Release of Tissue Plasminogen Activator (tPA)

Acute Myocardial Infarction

The restoration of coronary blood flow with tPA leads to improved survival in acute myocardial infarction. Experimental evidence indicates that Intra-Aortic Balloon Counterpulsation (IABC) enhances coronary reperfusion when used in conjunction with intravenous therapy with recombinant tissue plasminogen activator. This effect is unrelated to increased coronary blood flow but related to the elevation of diastolic pressure produced by the pulse from IABC (Gurbel P A et al. Arterial diastolic pressure augmentation by intra-aortic balloon counterpulsation enhances the onset of coronary artery reperfusion by thrombolytic therapy. Circulation 1994;89:361–65). This finding relates to the added pulses from balloon counterpulsation stimulating release of additional endogenous tPA, suppressing tPA inhibitors and antigens, and increasing nitric oxide release. In patients with cardiogenic shock complicating acute myocardial infarction, intraaortic balloon pumping in conjunction with administration of recombinant tPA decreased the odds of death by 18% (Barron J V et al The use of intra-aortic balloon counterpulsation in patients with cardiogenic shock complicating acute myocardial infarction. Am. Heart J.2001; 141:9330939)

Treatment with added pulses to the circulation to upregulate from endothelium the basal release of t-PA and inhibit the release of tPA antigen and tPA inhibitors as well as upregulate nitric oxide and prostacyclin release is indicated for the treatment of acute myocardial infarction and acute myocardial infarction with cardiogenic shock as a stand alone therapy or in conjunction with tPA or other "clotbusters."

Deep Venous Thrombosis

Prophylaxis against deep venous thrombosis currently involves two basic means, viz., pharmacologic (e.g., heparin and warfarin) and mechanical (e.g., elastic stockings and external pneumatic compression [ECP]). The latter compresses the legs a few seconds each minute. The compression collapses the veins, which increases venous blood flow during the period of the pulse. Although this treatment is accepted as effective, it has been found that pulsatile blood flow in a simulated in-vitro venous system produces much greater release of tPA as well as upregulation of eNOS (Dai G et al. An in vitro cell culture system to study the influence of external pneumatic compression on endothelial function. J.Vasc.Surg. 2000;32:977–87). Both pharmacological and mechanical interventions also prevent deep venous thrombosis.

Treatment with added pulses to the circulation to upregulate from endothelium the basal release of t-PA and inhibit the release of tPA antigen as well as upregulate nitric oxide and prostacyclin is indicated for the prevention and treatment of deep venous thrombosis.

Stroke

Intravenous administration of recombinant tissue plasminogen activator (t-PA) for stroke patients presenting within 3 hours after symptom onset is considered effective therapy. The duration of action of t-PA is prolonged by nitroprusside.

External addition of pulses to fluid circulation to release nitric oxide, prostacyclin, and t-PA from endothelium constitutes effective treatment of stroke without the potential of bleeding complications caused by intravenous administration of recombinant t-PA. Nitric oxide prolongs the action of t-PA.

Peripheral Arterial Occlusive Disease

Peripheral arterial disease (PAD) and its progression is associated with impaired fibrinolysis as determined with measurements of tissue plasminogen activator (t-PA) and its inhibitor plasminogen activator inhibitor-1 (PAI-1). tPA activity levels are significantly decreased in patients with severe claudication (SC) relative to those with mild intermittent claudication (MC) and the normal subjects. tPA antigen levels are significantly increased in the patients with SC compared with those with MC and the control subjects and there was a significant inverse correlation between tPA antigen levels and pain-free walking time in patients with claudication. All patients with peripheral arterial disease show significant reductions in endogenous fibrinolytic activity. Patients with SC had more impaired fibrinolytic activity than those with MC and the control subjects, suggesting that the progression to more severe levels of PAD may be associated with worsening endogenous fibrinolysis.

Longterm treatment with added pulses to the circulation to upregulate from endothelium the basal release of t-PA and inhibit the release of tPA antigen as well as upregulate nitric oxide and prostacyclin is indicated in patients with peripheral vascular disease.

Hepatic Veno-Occlusive Disease

Hepatic veno-occlusive disease often follows hematopoietic stem cell transplantation. This potentially fatal complication can be amelorated by early administration of recombinant t-PA. However, morbidity may be high due to bleeding associated with t-PA administration. Since hematopoietic stem cell transplantation is an elective procedure, pretreatment with external addition of pulses to the circulation has potential to prevent the complication of Hepatic veno-occlusive disease.

Pretreatment of patients undergoing hematopoetic stem cell transplantation with external addition of pulses to circulation by upregulating endothelial storage and release of tissue plasmiogen activator and suppression of tissue plasminogen inhibitor constitutes prophylaxis against a potentially fatal complication of this procedure, hepatic veno-occlusive disease.

Pulmonary Vascular Thrombosis

Pulmonary vascular thrombosis is a major complication of severe primary and secondary pulmonary hypertension.

External addition of pulses to the circulation has potential to prevent pulmonary vascular thrombosis through stimulation of endothelium to release t-PA, nitric oxide and prostacyclin and suppress tissue plasminogen inhibitor.

Decreased Release of Vascular Endothelial Growth Factor

Cancer

The growth of human tumors and development of metastases depend on the de novo formation of blood vessels. The formation of new blood vessels is tightly regulated by specific growth factors that target receptor tyrosine kinases (RTKs). Vascular endothelial growth factor (VEGF) and the Flk-1/KDR RTK have been implicated as the key endothelial cell-specific factor-signaling pathway required for pathological angiogenesis, including tumor neovascularization. By increasing shear stress to the endothelium, external addition of pulses to the circulation through nitric oxide modulatess release of VEGF but does not inhibit its release. The attenuation of VEGF is also found in skeletal muscle in trained subjects after an acute bout of exercise compared to higher values released during acute exercise in untrained subjects. Platelets are a storage means for biologically active VEGF. Platelets prevent circulating VEGF from inducing the development of new blood vessels except at sites where coagulation takes place. Interleukin 6 (IL-6), besides its thrombopoietic effect, also seems to affect the storage of VEGF in platelets. This is in accordance with the indirect angiogenic action of IL-6 reported previously. The interaction of IL-6 with the angiogenic pathways in cancer explains the stimulation of tumor growth occasionally observed during IL-6 administration.

External addition of pulses to the circulation modulates release of VEGF through nitric oxide release. Therefore, the external addition of pulses to the circulation might be used as an ancillary modality of treatment. For example, in several animal models, neutralizing anti-VEGF antibodies have encouraging inhibitory effects on solid tumor growth, ascites formation and metastatic dissemination. Targeting the VEGF signaling pathway by means of VEGF receptor tyrosine-kinase inhibitors has shown similar efficacy.

III. Treatments Using Combinations of Drugs or Devices and Mediators Produced by External Pulses L-Arginine L-arginine, the substrate for nitric oxide formation, also acts as an endothelium dependent vasodilator but is not a strict substitute since it often has different effects in specific vascular beds. For example, L-arginine does not reduce pulmonary arterial pressure in primary pulmonary hypertension whereas inhaled nitric oxide has this effect. L-arginine reduces pulmonary arterial pressure in secondary pulmonary hypertension. In patients with coronary artery disease, basal and acetylcholine-stimulated release of nitric oxide is reduced either as a result of depressed synthesis of nitric oxide or excessive degradation of nitric oxide by reactive oxygen species to biologically inactive or even toxic molecules. Serum nitric oxide in patients given oral -arginine (9 g/day for one month) was measured by a chemiluminescent technique and did not change brachial artery diameters and flow-mediated dilation nor nitroglycerin induced dilation. This failure to demonstrate an effect might have been due to other medical therapies that could not be stopped or too low of a dose. However, higher doses of L-arginine were associated with nausea, stomach cramps and diarrhea. Chronic L-arginine therapy of patients with coronary artery disease does not appear to be a major treatment rationale for coronary artery disease in terms of improving endothelial dysfunction. Further, most evidence indicates that the L-arginine-nitric oxide reaction is not rate-limited, meaning that there is sufficient circulating L-arginine such that eNOS always has a sufficient supply to form nitric oxide. Indeed, evidence has been obtained that the vascular effects of L-arginine are in fact due to its capability of increasing plasma insulin levels. This also explains the failure of L-arginine to improve reactive hyperemia in patients with atherosclerosis.

With regard to the negative findings of treatment of L-arginine in patients with coronary artery disease, the conflicting data of purported beneficial effects of L-arginine in other studies deserves the following comments. The availability of L-arginine for reaction with eNOS does not appear to be rate limiting. The intracellular levels of amino acid are in the millimolar range whereas the enzyme's Km for substrate is in the micromolar range. A possible mechanism relevent to atheriosclerotic disease is that oxidized LDL and lysophosphatidylcholine decrease L-arginine into endothelial cells. L-arginine competes with other cationic amino acids for transport into cells, especially L-glutamine, and increased L-arginine substrate might increase intracellular substrate by competitively enhancing cellular uptake in this setting. But by far the most attractive hypothesis is the following. The beneficial effects of L-arginine to increase nitric oxide even though the reaction is not rate-limited might result from its inhibition of intracellular NOS inhibitors, chief of which is asymmetrical dimethlarginine (ADMA). This accounts for the so-called L-arginine paradox.

Proposed indirect mechanisms by which L-arginine increase nitric oxide includes the following. L-arginine increases insulin secretion, which itself promotes vasodilation. L-arginine stimulates histamine release from mast cells that also evokes a vasodilator response. L-arginine can attenuate norepinephrine activity thereby enhancing the effects of endogenous vasodilators. Several explanations as to why the coronary artery study described above was negative include: 1) serum nitrates were unchanged by the added L-arginine, 2) the co-existing atherosclerosis in the patients might have limited both NO activity and production, 3) the patient's prior drug regimen may have improved endothelial function to a degree beyond which further improvement could not be realized.

The combination of L-arginine and external addition of pulses to the circulation provides additive and possibly synergistic vasodilator, antiplatelet aggregation and antileukocyte adhesion actions to endothelial release of mediators.

Insulin

Insulin has vasodilating properties in skeletal muscle vasculature, mediated by increased nitric oxide released from endothelium that subsequently stimulates prostaglandin release.

Augmentation index, a dimensionless parameter of systemic hypertension severity, is the difference between the second and first systolic peaks of the pulse divided by the pulse pressure. Administration of insulin diminishes augmentation index within an hour after beginning its infusion. Systemic systolic or diastolic blood pressure, forearm blood flow and vascular resistance do not change until 2 to 3 hours after insulin infusion. This effect is similar to nitroglycerin that also decreases augmentation index but in low doses has no effect on brachial arterial blood pressure or forearm blood flow. Augmentation index (A.I.) increases with age and usually has a positive valueafter age 40 years. In young subjects 25 years of age, A.I is negative at baseline and becomes even more negative with insulin. These augmentation changes reflect insulin action, which initially increases distensibility of large arteries, followed by increased distensibility of smaller resistance arteries.

The combination of insulin and external addition of pulses to the circulation provides additive and possibly synergistic vasodilator, antiplatelet aggregation and antileukocyte adhesion actions to endothelial release of mediators.

Adenosine

Adenosine is released by skeletal and cardiac muscles when their metabolism increases in order to couple oxygen supply with demand by causing vasodilatation. During systemic hypoxia, adenosine is predominantly released from the endothelium and acts on endothelial A1 receptors to produce dilatation in a nitric oxide-dependent manner. A1 receptor stimulation increases the synthesis of nitric oxide by a process initiated by opening of ATP-sensitive K+ (KATP) channels. Prostaglandins also make a major contribution to the hypoxia-induced dilatation, but the dilator pathways for adenosine, NO and prostaglandins are interdependent. In addition, adenosine released from the skeletal muscle fibers contributes indirectly to the dilatation by stimulating A1 and A2 receptors on the muscle fibers, opening KATP channels and allowing efflux of K+, which is a vasodilator.

Parasympathomimetics

Other endothelium dependent vasodilators include acetylcholine and methacholine parasympathomimetic drugs. These agents are administered by localized injection into the vascular stream for testing the integrity of endothelium dependent vasodilation and cannot be used to treat endothelial dysfunction. Neither drug is effective orally. Systemic injection causes undesirable side effects including provocation of bronchospasm.

Nitric Oxide Donors

Compounds such as nitroglycerin, nitroprusside and other organic nitrate compounds release nitric oxide through enzymatic degradation and act directly on vascular endothelium to cause vasodilation. These compounds are designated endothelium independent vasodilators since they relax vascular smooth muscle even though vascular endothelium may be dysfunctional or destroyed at a given site of action. However, enzyme conversion may not be complete at different sites or other vasoactive compounds may be formed leading to different actions on different vascular beds and drug tolerance. The latter leads to less effectiveness for a given dose of organic nitrate within a few days of usage.

Nitric oxide donors are more potent in veins and the radial artery (vessels with minimal basal NO-mediated dilatation) than in the resistance vascular bed (where basal NO is a major determinant of vascular tone). In contrast, 8-bromoguanosine 3',5'-cyclic monophosphate (cGMP mimetic) is approximately equipotent in resistance arteries and veins and less potent in the radial artery. Inhibition of phosphodiesterase V with dipyridamole does not alter the arteriovenous profile of nitroglycerin. Increasing the local concentration of nitric oxide in veins (by infusing sodium nitroprusside) reduces sensitivity to nitroglycerin but not to 8-bromoguanosine 3', 5'-cyclic monophosphate. Conversely, reducing endogenous nitric oxide production in the resistance vessels leads to time-dependent increases in the response to nitroglycerin. Soluble guanylate cyclase rather than cGMP-dependent protein kinase or phosphodiesterase V appears to be the site for the second messenger pathway that determines the arteriovenous profile of nitric oxide donors. Moreover, the sensitivity of soluble guanylate cyclase to nitric oxide donors might be regulated by the ambient concentration of nitric oxide, with increased local nitric oxide downregulating the dilator response to nitric oxide donors. Therefore, the combination of nitric oxide donors and externally added pulses to the circulation constitutes a relative contraindication.

Beta 2 Adrenergic Agonists.

Beta-2 adrenergic agonists such as albuterol, salbutamol and isoproterenol are endothelial dependent vasodilators that act through the nitric oxide-L-arginine pathway. Their side effects and diverse range of actions prevent them from being used for treatment of endothelial dysfunction.

Angiotensin Converting Enzyme (ACE) Inhibitors

Fosinopril, an ACE inhibitor, reduces blood pressure and Augmentation Index, a measure that reflects arterial vascular stiffness and signifies systolic blood pressure above that measured by conventional means due to wave reflection. Release of nitric oxide diminishes arterial stiffness and the Augmentation Index.

The ACE inhibitor, enalaprilat, augments nitric oxide induced vasodilation in healthy volunteers. Although angiotensin converting enzyme inhibitors alone do not affect basal forearm blood flow or vascular resistance, they significantly augments the increase in blood flow and reduction in vascular resistance induced by acetylcholine, an endothelial dependent vasodilator. Coinfusion of enalaprilat does not enhance sodium nitroprusside-induced vasodilation. Pretreatment with the NOS inhibitor, NG-monomethyl-L-arginine, blocks augmentation of blood flow induced by the angiotensin converting enzyme inhibitor.

Angiotensin converting enzyme (ACE) inhibitors not only reduce angiotensin II, but also increase bradykinin levels, since the angiotensin converting enzyme is identical to kininase II, an enzyme that degrades bradykinin. ACE inhibition improves flow-dependent, endothelium-mediated vasodilation and this beneficial effect of ACE inhibition is bradykinin dependent. The beneficial effects of ACE inhibition in heart failure and coronary artery disease are partly due to improved endothelial function.

In end stage renal disease patients, ACE inhibition results in a long-lasting, blood pressure-independent decrease in arterial wave reflections. The consequence of this is a decrease in pulsatile pressure load in the central arteries with increased aortic distensibility. The increased aortic distensibility results from the decrease in blood pressure. The observed arterial hemodynamic alterations suggest that ACE inhibition induced diminution of arterial wave reflections from distal parts of the arterial tree. This is probably related to upregulation of eNOS.

The combination of angiotensin converting enzyme (ACE) inhibitors and external addition of pulses to the circulation provides additive and possibly synergistic vasodilator, antiplatelet aggregation and antileukocyte adhesion actions to endothelial release of mediators.

Angiotensin II Receptor Blockers (ARBs)

Angiotensin II receptor blockers (ARBs) represent a new class of effective and well tolerated orally active antihypertensive agents. The angiotensin II receptor blocker, candesartan, improves tonic nitric oxide release and reduces vasoconstriction to endogenous ET-1 in the forearm of hypertensive patients. The ARBs specifically block the interaction of angiotensin II at the AT1 receptor, thereby relaxing smooth muscle, increasing salt and water excretion, reducing plasma volume, and decreasing cellular hypertrophy. These agents exert their blood pressure-lowering effect mainly by reducing peripheral vascular resistance usually without a rise in heart rate. The renin-angiotensin system (RAS) represents one of the most strategic targets of the therapy of cardiovascular diseases. The use of ACE-inhibitors has led to significant improvements in the outcome/treatment of hypertension, congestive heart failure, ischemic heart disease and nephropathies. On the other hand, ACE-inhibitors are not specifically targeted to RAS since they interfere with an enzyme with multiple different substrates. Furthermore, inhibition of ACE does not prevent the formation of angiotensin II through alternative pathways, and thus the inhibition of RAS is often incomplete, especially under pathologic conditions stimulating RAS. Angiotensin II receptors antagonists, such as losartan, selectively inhibit the action of angiotensin II at the level of the AT1 subtype receptor. Inhibition of the AT(1) receptor in patients with atherosclerosis reverses endothelial dysfunction by improving nitric oxide availability and therefore may have long-term therapeutic benefits.

The combination of angiotensin II receptor blockers and external addition of pulses to the circulation provides additive and possibly synergistic vasodilator, antiplatelet aggregation and antileukocyte adhesion actions to endothelial release of mediators.

Angiotensin-(1-7)

Angiotensin-(1-7) formed from Angiotensin I and Angiotensin II by itself does not have vasodilating properties but acts as a angiotensin receptor antagonist when the renin-angiotensin system is activated. Angiotensin-(1-7) acts as a local synergistic modulator of kinin-induced vasodilation by inhibiting angiotensin converting enzyme and releasing nitric oxide.

The combination of Angiotensin-(1-7) and external addition of pulses to the circulation provides additive and possibly synergistic vasodilator, antiplatelet aggregation and antileukocyte adhesion actions to endothelial release of mediators.

Beta Blockers

Atenolol a beta blocker, reduces blood pressure to the same extent as the ACE Inhibitor, Fosinopril. It decreases Augmentation Index, a measure that reflects stiffness of arterial blood vessels but to a lesser extent than does the ACE inhibitor. Other beta blockers may not have even less effect than atenolol.

The combination of certain beta blockers and external addition of pulses to the circulation provides additive and possibly synergistic vasodilator, antiplatelet aggregation and antileukocyte adhesion actions to endothelial release of mediators.

Calcium Antagonists

Nitric oxide synthesis in vascular endothelium of patients with hypertension is altered. Calcium antagonists have been shown to improve endothelial function in hypertensive patients. Pranidipine, one of the latest long-acting calcium antagonists in the dihydropyridine group, enhances the actions of nitric oxide released from endothelial cells (ECs). Pranidipine significantly enhanced cGMP accumulation in vascular smooth muscle cells cocultured with endothelial cells, whereas amlodipine and nifedipine had no significant effects. In addition, pranidipine suppresses basal and thrombin-stimulated endothelin-1 production. Pranidipine also enhances cGMP accumulation in rat aortic segments with endothelium but not in endothelium-denuded vessels. This drug has no effect in the presence of N(G)-monomethyl-L-arginine, an inhibitor of nitric oxide synthesis. Pranidipine does not affect the basal expression of endothelial nitric oxide synthase in endothelial cells. However, pranidipine upregulates the activity of superoxide dismutase in endothelial cells. Thus, pranidipine enhances nitric oxide action through inhibition of superoxide-induced nitric oxide decomposition in the vessel wall.

The combination of pranidipine and other calcium antagonists that upregulate the activity of superoxide dismutase along with external addition of pulses to the circulation provides additive and possibly synergistic vasodilator, antiplatelet aggregation and antileukocyte adhesion actions to endothelial release of mediators.

Statins

These drugs diminish plasma cholesterol levels and upregulate eNOS leading to increased levels of plasma nitrite/nitrate after two weeks oral therapy. In non-hypercholesterolemic animals, the upregulation of eNOS is associated with increased coronary blood flow. Epidemiological studies indicate that there is lower incidence of bone fractures in elderly patients taking statins that is independent of cholesterol lowering action, a benefit that is probably linked to the upregulation of eNOS in osteoblasts. Examples of statin drugs include atorvastatin, pravastatin and simvastatin. These drugs also reduce platelet aggregation and act as vasodilators. These effects reflect the antiplatelet aggregation and antileukocyte adhesive actions to endothelium as mediated by nitric oxide release. Further, statins inhibit basal and stimulated Plasminogen Activator Inhibitor and promote release of tPA from endothelium. These effects mimic the action of adding pulses to the circulation.

Chronic treatment with statins elevates cerebral blood flow by upregulation of eNOS leading to increased nitric oxide generation. In mice, after eNOS upregulation by chronic treatment, L-arginine increased brain blood flow 38%. Upregulation of neuronal and inducible nitric ocide synthases, NNOS and iNOS, respectively, did not occur. The improved blood flow effect was enhanced by L-arginine in experimental cerebral ischemia.

The combination of statins and external addition of pulses to the circulation provides additive and possibly synergistic vasodilator, antiplatelet aggregation, antileukocyte adhesion actions, and bone building to the endothelial release of mediators brought about the addition of pulses.

Estrogens

Endogeneous and exogenous estrogens cause vasodilation by acting through the nitric oxide-L-arginine pathway. Short-term unopposed estrogen rerplacement therapy favorably enhances arteriolar distensibility, baroreceptor sensitivity and blood pressure in postmenopausal women.

The combination of estrogens and external addition of pulses to the circulation provides additive and possibly synergistic vasodilator, antiplatelet aggregation and antileukocyte adhesion actions to endothelial release of mediators.

Atrial Natriuretic Peptide (ANP)

Atrial natriuretic peptide (ANP) increases nitric oxide synthesis capability and production probably through the cGMP pathway. The nitric oxide pathway could be an intercellular messenger in the ANP endothelium-dependent vasorelaxation mechanism.

The combination of atrial natriuretic peptide and external addition of pulses to the circulation provides additive and possibly synergistic vasodilator, antiplatelet aggregation and antileukocyte adhesion actions to endothelial release of mediators.

Phosphodiesterase Inhibitors

Sildenafil (Viagra) is a PDE-5 inhibitor (phosphodiesterase-3 inhibitor) that increases the availability of cyclic guanosine monophosphate (cGMP), an intracellular messenger of nitric oxide, by blocking its degradation. Dipyridamole is also a PDE-5 inhibitor that has been used in combination with inhaled NO to decrease pulmonary artery pressure in patients with pulmonary hypertension.

Milrinone is a PDE-3 inhibitor (phosphodiesterase-3 inhibitor). PDE-3 inhibitors increase concentrations of cAMP in cardiac and vascular smooth muscle, producing inotropic and systemic and pulmonary vasodilator effects. Milrinone is an effective pulmonary vasodilator and its reduction of pulmonary arterial pressure in pulmonary hypertension is additive to inhaled nitric oxide.

Phosphodiesterase inhibitors (PDE-4) include a large family of enzymes, e.g., theophylline, that consist of acidic proteins which exclusively hydrolyse cAMP and are inhibited by nanomolar concentrations of rolipram. PDE-4 inhibitors potentiate the action of nitric oxide.

L-arginine is additive to the vasodilator action of PDE-3 inhibitors, amrinone and milrinone and synergistic with PDE-5 inhibitors, zaprinast and sildenafil. Amrinone and milrinone, are cAMP-dependent phosphodiesterase inhibitors whereas zaprinast and sildenafil are cGMP-dependent phosphodiesterase inhibitors. Therefore, external addition of pulses to the circulation in combination with PDE-3 inhibitors provides an additive effect to nitric oxide action and in combination with PDE-5 inhibitors a synergistic one.

The combination of phosphodiesterase inhibitors-3 or -4 or -5 and external addition of pulses to the circulation provides additive and synergistic vasodilator, antiplatelet aggregation and antileukocyte adhesion actions to endothelial release of mediators.

Xanthine Oxidase Inhibitors

Xanthine oxidase inhibitors such as allopurinal enhance action of nitric oxide by decreasing $O_2$-that oxidizes nitric oxide. Xanthine oxidase-generated superoxide anions are partly responsible for the impaired endothelial vasodilator function of hypercholesterolemic patients but this mechanism does not appear to play a significant role in essential hypertension.

The combination of xanthine oxidase inhibitors and external addition of pulses to the circulation provides additive and possibly synergistic vasodilator, antiplatelet aggregation and antileukocyte adhesion actions to endothelial release of mediators.

Monamine Oxidase Inhibitors

The monoamine oxidase-B (MAO-B) inhibitor L-deprenyl (Selegiline) is effective in treating Parkinson's disease and possibly Alzheimer's disease, with a concomitant extension of life span. The therapeutic efficacy of L-deprenyl may involve actions other than the inhibition of the enzyme MAO-B. Stimulation of nitric oxide production could be central to the action of the drug. L-Deprenyl induces rapid increases in nitric oxide production in brain tissue and cerebral blood vessels. In vitro or in vivo application of L-deprenyl produces vasodilatation. The drug also protects the vascular endothelium from the toxic effects of amyloid-beta peptide. Because nitric oxide modulates activities including cerebral blood flow and memory, and reduced nitric oxide production has been observed in brains of Alzheimer's Disease, stimulation of nitric oxide production by L-deprenyl could contribute to the enhancement of cognitive function in Alzheimer's Disease. MAO-B inhibitors are unique in that they exert protective effects on both vascular and neuronal tissue and thus warrant further consideration in the treatment of vascular and neurodegenerative diseases associated with aging.

The combination of the monamine oxidase-B inhibitor, L-deprenyl and external addition of pulses to the circulation provides additive and possibly synergistic effects on the prevention and treatment of Alzheimer's disease.

Endothelin Receptor Antagonists

There are a number of experimental drugs that antagonize endothelin receptors. Since endothelins are vasoconstrictive mediators, their action potentiates the vasodilator effect of nitric oxide.

The combination of endothelin receptor antagonists and external addition of pulses to the circulation provides additive and possibly synergistic vasodilator, antiplatelet aggregation and antileukocyte adhesion actions to endothelial release of mediators.

Superoxide Dismutase (SOD)

Physiological levels of shear stress increase expression of Cu/Zn SOD in the endothelium. This adaptation to shear stress augments the effect of locally produced NO and thereby promotes the antiatherogenic and anti-inflammatory properties of the endothelial cell. The effective half-life of nitric oxide and the relaxation of aortic rings by NO is enhanced by a reduction in the concentration of superoxide radicals with superoxide dismutase. SC52608, a newly synthesized SOD mimic, potentiates the actions of nitric oxide on vascular tone, cyclic GMP, and blood pressure by enhancing the half-life of nitric oxide through a mechanism that mimics the action of SOD.

The combination of SC52608, a synthesized superoxidase dismutase mimic, and external addition of pulses to the circulation provides additive and possibly synergistic vasodilator, antiplatelet aggregation and antileukocyte adhesion actions to endothelial release of mediators.

Prolonged Slow Release of Nitric Oxide

During exposure to elevated physiological levels of nitric oxide, vascular endothelium produces peroxynitrite (ONOO—), a species that seems to participate in prolonging the initial vascular smooth muscle relaxation to nitric oxide through a thiol-dependent trapping and/or regeneration of nitric oxide.

Furoxans are prodrugs that increase the level of cyclic GMP via formation of nitric oxide and may therefore be classified as nitrovasodilators. Along with the generation of nitric oxide, nitrite and nitrate ions and S-nitrosothiols are formed. Furoxans release nitric oxide upon reaction with thiols.

The combination of furoxins or S-nitrosothiol derivatives that release nitric oxide slowly and external addition of pulses to the circulation provides additive and possibly synergistic vasodilator, antiplatelet aggregation and antileukocyte adhesion actions to endothelial release of mediators.

Nitric Oxide Synthase Inhibitors

Non-Specific. Several generalized nitric oxide inhibitors for administration into the body. These include among others L-NAME and L-NMMA, and are related to L-arginine in chemical structure. Most studies in humans have focused on their effects upon the vascular system. Here, because of their inhibition of eNOS, these agents diminish basal release of nitric oxide from endothelium thereby causing vasoconstriction and hypertension. Their treatment of conditions associated with increased release of nitric oxide such as portal cirrhosis and septic shock has been disappointing.

Specific. Experimental agents for selective inhibition of iNOS and nNOS have become available. These drugs have promise to beneficially treat certain conditions in conjunction with drugs or externally added pulses to the circulation. For example, experimental cerebral contusion is associated with activation of all three NOS isoforms. Endothelial NOS is expressed exclusively in endothelial cells, whereas iNOS is expressed in neutrophils and macrophages. Neuronal NOS is predominantly detected in neurons but also in polymorphonuclear cells. The most striking finding regarding nitric oxide producing enzymes is the expression of iNOS in polymorphonuclear cells and macrophages, cells that invade and destroy both injured and normal brain tissues. iNOS is thus implicated as a therapeutic target in contusional injuries. This pattern of NOS expression cannot be generalized to all types of brain injuries. The different compartments and cells that can produce nitric oxide are differentially regulated; therefore, compartmentalization can explain why nitric oxide is beneficial or detrimental, depending on the circumstances. Thus vasodilation of cerebral blood vessels to increase blood flow to damaged brain tissue through upregulation of eNOS is beneficial in brain contusion whereas upregulation of iNOS is harmful. Therefore, a therapeutic strategy to treat brain contusion is to combine iNOS inhibitor with external addition of pulses to the circulation as a means to upregulate eNOS, prostacyclin, and t-PA.

Glutamate excitotoxicity, oxidative stress, and mitochondrial dysfunctions are common features leading to neuronal death in cerebral ischemia, traumatic brain injury, Parkinson's disease, Huntington's disease, Alzheimer's disease and amyotrophic lateral sclerosis. Nitric oxide (NO) alone or in cooperation with superoxide anion and peroxynitrite is emerging as a predominant effector of neurodegeneration. The use of NO synthase (NOS) inhibitors and mutant mice lacking each NOS isoform have provided evidence for the injurious effects of NO derived from neuronal or inducible isoforms. New neuroprotective strategies have been proposed with selective NOS inhibitors for the neuronal (ARL17477) or the inducible (1400 W) isoforms or with compounds combining in one molecule selective nNOS inhibition and antioxidant properties (BN 80933), in experimental ischemia-induced acute neuronal damage. The efficacy of these new strategies is well established in acute neuronal injury but remains to be determined in more chronic neurological diseases.

Septic and hemorrhagic shock is another example where the combination of a selective iNOS inhibitor to mitigate the inflammatory response and external added pulses to the circulation to decrease pulmonary vascular resistance provides beneficial treatment.

The combination of specific as yet experimental, iNOS (1400 W, aminoguanidine, radicicol, L-NIL, and interferon-β) and nNOS (ARRI 7338, ARL17477) inhibitors among others together with external addition of pulses to the circulation as a means to provide solely nitric oxide from eNOS, provides therapeutic benefits to acute brain injuries and chronic neurodegenerative disease. Acute brain injuries include stroke and brain contusion among others. Chronic neurodegenerative diseases include Parkinson's disease, Huntington's disease, Alzheimer's disease, amyotrophic lateral sclerosis, and multiple sclerosis among others. eNOS nitric oxide acts beneficially as a vasodilator, inhibitor of platelet aggregation and leukocyte adhesion, and suppresses interleukin-6. nNOS and particularly iNOS release nitric oxide in brain tissue creates damage in itself.

Prostacyclin

Prostacyclin is liberated from endothelium by shear stress and relaxes vascular smooth muscle as an endothelium independent vasodilator. In most blood vessels, the contribution of prostacyclin to endothelial-dependent vasodilation is small and its effect is additive to nitric oxide. However, in terms of preventing platelet aggregation, leukocyte adhesion to endothelium, and susceptibility to thrombosis, the action of prostacyclin and nitric oxide are synergistic. Nitric oxide has an inhibitory effect on prostacyclin production under shear stress but vessel homeostasis is maintained through an increase in prostacyclin production when nitric oxide synthesis is impaired in endothelial cells as in atherosclerosis.

Shear stress independent of perfusion pressure increases gene expression of prostacyclin synthesis-related enzymes cyclooxygenases (COX-1 and COX-2), prostacyclin synthase (PGS), and thromboxane synthase (TXS) and their metabolites prostaglandin (PGI(2)) and thromboxane A(2) (TXA(2)) in endothelium of intact conduit vessels.

With reactive hyperemia, radial arterial diameter increases but with combination of reactive hyperemia and L-NMMA, a NOS inhibitor, radial diameter decreases. In contrast to L-NMMA, cyclooxygenase inhibition with aspirin does not affect hyperemic response or flow dependent dilation of the radial artery. Thus, prostacyclin release does not appear to participate to a significant extent in flow dependent dilation of radial artery.

The combination of admistered prostaglandins and external addition of pulses to the circulation provides additive vasodilator action and synergistic, antiplatelet aggregation and antileukocyte adhesion actions to endothelial release of mediators.

In addition, synergism is present among three antiplatelet drugs with different modes of action: aspirin, an inhibitor of the cyclooxygenase pathway of platelet activation; iloprost, a stable analog of prostacyclin that increases platelet cAMP; and the nitric oxide donors SIN-1 and sodium nitroprusside (SNP), which both raise platelet cGMP.

The combination of aspirin, and/or iloprost along with external addition of pulses to the circulation provides synergistic antiplatelet aggregation properties.

YC-1

Nitric oxide, the physiological activator of soluble guanylyl cyclase (sGC), induces inhibitory effects on platelet activation via elevation of cGMP levels and stimulation of the cGMP-dependent protein kinase. YC-1, a benzylindazole derivative, activates sGC in intact platelets, resulting in inhibition of platelet aggregation. YC-1 not only stimulates purified sGC but also potentiates the stimulatory action of submaximally effective nitric oxide concentrations. YC-1 together with nitric oxide leads to complete inhibition of platelet aggregation at concentrations that are ineffective by either. YC-1 not only stimulates sGC but also inhibits cGMP-hydrolyzing phosphodiesterases in platelets. The combination of two effects, i.e., potentiation of nitric oxide-induced sGC stimulation and phosphodiesterase inhibition, of YC-1-like substances causes potent activation of the sGC/cGMP pathways.

The combination of YC-1, a platelet aggregation inhibitor and external addition of pulses to the circulation provides synergistic antiplatelet aggregation and antileukocyte adhesion actions to endothelial release of nitric oxide.

Light/Laser Therapy in Wound Healing (e.g., Acute Gastric Injury)

After release of nitric oxide from the endothelium, some of it combines with non-hemic iron in the red blood cell to form a nitrosyl complex of hemoglobin. This serves a temporary depot or possible transport form of nitric oxide. It has been shown that the MIRE device (BioScan™ that delivers 890 nanometer (nm) monochromatic infrared energy is effectivein treating recalcitrant dermal lesions, including venous ulcers, diabetic ulcers, and wounds related to scleroderma. The rate and quality of healing of these previously refractory wounds, following use of minimally thermic, monochromatic infrared energy, appears to relate to local increases in nitric oxide concentration probably released firm the nitrosyl complex of hemoglobin. Other light sources such as He-Cd laser irradiation (441 nm) also release nitric oxide from hemoglobin. Thus, the combination of light/laser therapy with external addition of pulses to the circulation has potential to provide additive or synergistic means to enhance wound healing Chronic addition of external pulses to the circulation in combination with light/laser therapy for treatment of recalcitrant dermal lesions, including venous ulcers, diabetic ulcers, and wounds related to scleroderma produces an additive or synergistic action in enhancing healing.

IV. Testing Efficacy of Treatments

Setup for Recognition that Pulses are Added to Circulation During Periodic Acceleration Ascertaining that pulses are being added to the circulation is ideally determined with a plethysmograph placed over the distal pad of the thumb. The inductive plethysmograph tranducer is the preferred sensor though other sensors will also acceptably perform. The thumb must be oriented horizontally with its tip facing the feet or head in the Gz plane or the added pulses on the patient's own pulse may be motion artifacts due to periodic acceleration. The validity of the added pulses can be tested by placing a pediatric blood pressure cuff on the proximal thumb and occluding the pulse during periodic acceleration produced by the motion platform. If true pulses are being added to the circulation, then the pulse waveform during periodic acceleration becomes flattened with minimal oscillations due to periodic acceleration. Pulses are added at oscillatory motion platform frequencies from approximately 150 to 240 per minute with pGz forces required to achieve these conditions in adults ranging from approximately ±0.25 to ±0.6.

Digital Pulse-Dicrotic Notch

Endothelial Function

The finger transmittance infrared photoplethysmograph can be used to obtain the digital pulse in response to systemic nitroglycerin and albuterol administration. Both drugs delay dicrotic notch appearance by reducing pressure wave reflection. The normal reflected waves that arise from small arteries are delayed relative to the direct wave and therefore produce an inflection point or second peak on the digital pulse volume trace, the dicrotic notch. Administration of small arterial vasodilators drugs reduces wave reflection thereby lowering the position of the dicrotic notch on the diastolic limb of the digital pulse wave in proportion to the degree of vasodilation. The vasodilator effects of nitroglycerin are mediated through its metabolism to nitric oxide and nitrosothiol compounds. Therefore, the descent of the dicrotic notch on the digital arterial pulse (or other systemic vessels) can be used to assess efficacy of nitric oxide action. Indeed, Smolen & Williams in 1973 prepared a document for FDA that utilized position of the dicrotic notch as a means to evaluate pharmacological effectiveness and comparative bioavailability of organic nitrate anti-anginal preparations.

Albuterol, a beta adrenergic agonist, produces vasodilation through a nitric oxide-L-arginine pathway and therefore its response might be blunted by endothelial dysfunction whereas nitroglycerin is endothelial independent. In type 2 diabetes, there are blunted responses to albuterol with regard to b/a ratio, a measure derived from the digital pulse height of the dicrotic notch upward inflection point from its point on the pulse wave downward to end-diastolic level (b) divided by the total amplitude of the pulse waveform (a). The dicrotic notch upward inflection point is best identified on the first or second mathematical derivatives of the digital pulse. In type 2 diabetics, the digital artery b/a ratio diminishes normally with nitroglycerin, a nitric oxide endothelial independent vasodilator. This blunted response of the dicrotic notch to systemic albuterol demonstrates endothelial dysfunction in diabetes type-2 since albuterol is a nitric oxide endothelial dependent vasodilator and nitric oxide is not normally released from dysfunctioning endothelium. The change in delay of the dicrotic notch correlates well with the pulse wave velocity between the foot of aortic bifurcation and subclavian artery (r=0.75). This measure reflects arterial stiffness that is lessened with nitric oxide vasodilation.

A more direct measurement of arterial stiffness is the Augmentation Index that also can be computed from the digital pulse (or other systemic arterial pulse waveforms). The Augmentation Index, a dimensionless parameter, is defined as the ratio of the amplitude of pressure wave between its initial systolic shoulder to the peak divided by the pulse amplitude and increases as a function of age. It reflects wave reflection as a function of arterial stiffness and correlates well to pulse wave velocity. Since nitric oxide decreases arterial stiffness, the pulse wave travels more slowly to the periphery and is reflected backwards more slowly such that Augmentation Index approaches zero. On the other hand, if L-NAME, a NOS inhibitor, or a vasopressor drug such as phenylephrine, is administered, the pulse wave travels more rapidly to the periphery and is reflected backward more rapidly such that it may arrive at the ascending aorta while the left ventricle is in the act of systole. This increases the Augmentation Index such that the left ventricle must contract against an "augmented" systolic pressure. Therefore, it is not surprising that Augmentation Index and left ventricular mass correlate well. External addition of pulses to the circulation in the presence of normal endothelial function release nitric oxide that delays wave reflection because of lessened arterial stiffness leading to diminution of the Augmentation Index.

External addition of pulses to the circulation causing release of nitric oxide from vascular endothelium serves as a test of endothelial function that can be assessed from position of the dicrotic notch and computation of the Augmentation Index. The digital pulse waveform (or pulse waveforms from other systemic arteries measured by plethysmographic, applanation tonometric, or imaging techniques) is recorded in conjunction with an electrocardiograph waveform. To compute the dicrotic notch ratio and Augmentation Index as markers of nitric oxide effect during external addition of pulses to the circulation, it is necessary to filter the added pulses from the fundamental digital pulse wave. Removal of added pulses is accomplished by ensemble averaging of several heartbeats of the digital pulse wave from an R-wave trigger of the electrocardiogram. The averaged digital pulse wave (or systemic arterial waveform) is displayed free of the externally added pulses thereby allowing identification of the dicrotic notch and computation of the Augmentation Index.

In the presence of normal endothelial function, external addition of pulses to the circulation stimulates endothelial cells and decreases this the b/a ratio due to vasodilation as a result of nitric oxide release because the value of (b) decreases much more than any changes of (a). The frequency, amplitude of added pulses, and peak acceleration of the "added pulses to the circulation devices" plotted against the b/a ratio provides graphs of dose-response curves. These can be compared to dose response curves from position of the dicrotic notch after nitroglyerin, a nitric oxide donor drug, as its effect is better determined with dicrotic notch position of an arterial waveform than plasma concentrations of the drug. Alternately, dose response curves during added pulses in a given subject can be compared to a normal control population. The dose response curves of the b/a ratio of the digital pulse can be calculated as follows. The estimated pharmacological effect is designated 'E' and 1n is the natural logarithm used to obtain linear dose response curves. E=1 n $(b_t/a_t - b_o/a_o)$ where o=baseline and t=any given dose. The dose of the "external added pulses devices" can be expressed as the value of frequency and amplitude of added pulses, or peak acceleration delivered by the "external added pulses devices" and dose response curves constructed for the b/a ratio.

The display of the averaged digital pulse waveform (or any systolic arterial waveform) allows computation of the Augmentation Index, a dimensionless number, defined as the ratio of the amplitude of pressure wave between its initial systolic shoulder to the peak divided by the pulse amplitude. It reflects wave reflection as a function of arterial stiffness and correlates well to pulse wave velocity. Since nitric oxide decreases arterial stiffness, the pulse wave travels more slowly to the periphery and is reflected backwards more slowly such that Augmentation Index approaches zero. In arterial stiffness as due to atherosclerosis or hypertension with endothelial dysfunction, Augmentation Index is elevated and is not lowered to the same extent by external addition of the pulses to the circulation as in the presence of normal functioning endothelium. The dose of the "external added pulses devices" can be expressed as the value of frequency and amplitude of added pulses, or peak acceleration delivered by the "external added pulses devices" and dose response curves constructed for the Augmentation Index.

Endothelial Dysfunction in Hypertension

Abnormalities of endothelial release of nitric oxide or deficiency of nitric oxide production in systemic hypertension serve as the first step in the process of vascular smooth muscle growth and eventual atherosclerosis. Testing for endothelial dysfunction may be a sensitive means for identifying individuals at risk for cardiovascular events. Current tests that involve response of forearm blood flow after brachial arterial infusion of acetylcholine or methacholine, endothelium dependent vasodilators, reactive hyperemia, or inhibition of nitric oxide synthesis through administration of L-NAME, a non-specific nitric oxide synthase (NOS) inhibitor to induce regional and systemic vasoconstriction directly related to the magnitude of basal nitric oxide are cumbersome and invasive. Analysis of the position of the dicrotic notch (b/a ratio) and computation of the Augmentation Index are other non-invasive tests that also assess endothelial function.

Because endothelial function is directly involved in maintaining a low arterial tone and preventing vascular smooth muscle hypertrophy, maintenance of a normal arterial compliance or distensibility depends on the adequacy of nitric oxide release and effect.

Cardiovascular events usually result from vascular accidents superimposed on the abnormal structure of the blood vessel. Thus, the health of the vasculature of individual patients with hypertension differentiates risk from non-risk patients. This is because hypertension is only one of many factors that contribute to the incidence of vascular events. Since offspring of essential hypertensive patients are characterized by a reduced response to acetylcholine linked to a defect in the nitric oxide pathway, this suggests that a genetic defect of eNOS might also be present.

Authorities in the field have stated that there is need for practical screening assessment of arterial wall structure in an at-risk population to monitor therapeutic interventions.

Thus, a drug regimen that does not favorably affect arterial structure in a given patient can be replaced by another drug regimen that might be more effective. The correction of the arterial wall abnormality could then serve as a guide to therapeutic efficacy rather than the absolute level of blood pressure, which now serves as a surrogate marker. The invention in this patent application deals with a practical screening test.

External addition of pulses to the circulation causing release of nitric oxide from vascular endothelium serves as a test of endothelial function that can be assessed from position of the dicrotic notch and computation of the Augmentation Index as described in the preceding section "Endothelial Function." Abnormal responses, e.g., little or no change in dicrotic notch position or Augmentation Index, over a wide range of externally applied pulses, occur in the following degenerative vascular diseases among others, coronary artery disease, diabetes mellitus, systemic hypertension, insulin resistance syndrome, atherosclerosis, hypertriglyceridemia, hypercholesterolemia, and chronic heart failure. Although endothelium dysfunction is present in typical angina pectoris, it can be normal in vasospastic (atypical) angina even though coronary blood vessels have endothelial dysfunction.

Digital Pulse Inductive Plethysmograph

The digital pulse inductive plethysmographic consists of wrapping an inductive plethysmographic sensor around a digit of the hand or foot. The technology is adapted from the expired patent for monitoring respiration with this inductive plethysmography. This expired patent is U.S. Pat. No. 4,308,872 Jan. 5, 1982: Method And Apparatus For Monitoring Respiration, Inventors: Herman L. Watson, Marvin A. Sackner & Frank D. Stott.

First Derivative

The upward inflection point of the dicrotic notch to compute the b/a ratio is better identified from the first derivative of the digital pulse waveform than the undifferentiated waveform. External addition of pulses to the circulation in the presence of normal endothelial function increases b/a by causing a moderate increase in 'a' and a marked increase in 'b'.

Second Derivative

The second derivative of the digital pulse plethysmograph provides another means to identify features of the digital pulse waveform. The sharp upward deflection at the initiation of the systolic upstroke and is labeled 'a'. This is followed by a sharp negative deflection that marks the rounding of the upstroke or first shoulder and is labeled 'b'. The next smaller upward wave though still negative with respect to the zero crossing marks the next rise or augmentation in the systolic peak and is labeled 'c'. The next wave labeled 'd,' a smaller downward deflection, represents the decline in systole to the beginning of the dicrotic notch. The next rounded upward deflection above the baseline labeled 'e' represents the dicrotic notch. The ratio of b/a of the second derivative of the plethysmogram or is positively correlated to age and atherosclerosis because the first shoulder is decreased in slope. Angiotensin decreases b/a ratio by causing a marked decrease in 'b' and a slight decrease in 'a' (note this is a different ratio than the dicrotic notch ratio of the undifferentiated digital pulse). External addition of pulses to the circulation in the presence of normal endothelial function increases b/a by causing a moderate increase in 'a' and a marked decrease in 'b'. The frequency and amplitude of the added pulses and the peak acceleration delivered by the added pulses device plotted against the b/a ratio enables construction of dose-response curves.

The 'a' and 'd waves of the second derivative of the digital pulse (low passed up to 10 Hz) are decisive in differentiating augmentation aspects after administration of vasoactive drugs. After IV injection of angiotensin, a vasopressor agent, there is a deepened 'd' wave in relation to the 'a' wave. This results from a higher second shoulder of the undifferentiated pulse. After nitroglycerin sublingually, there is marked reduction of the second shoulder with 'd' becoming shallower relative to 'a'. The ascending aortic pressure increases after angiotensin and decreases after nitroglycerin. The d/a ratio decreases after angiotensin and increases after nitroglycerin. The negative d/a increases with increases in both digital pulse plethysmographic and ascending aortic Augmentation Indices, confirming the validity of digital pulse wave assessments of vasoactive agents.

Oscillometric Plethysmograph

This consists of measuring the pressure changes in an inflatable cuff around the terminal phalynx with a cuff pressure of 50–60 mm Hg or 10 mm Hg below diastolic pressure. This oscillometric method, also called the pneumoplethysmographic method, is associated with a damped pulse waveform.

Piezoelectric Sensor

The transducer is held in place on the finger pulp with a surrounding cuff inflated to 50–60 mm Hg. This method is associated with a damped pulse waveform.

Strain Gauge

Strain gauge plethysmography consists of wrapping a mercury in silastic transducer around the finger with a degree of stretch. It is a good method but is influenced by environmental temperature and provides measurement of circumference rather than volume as does the digital pulse inductive plethysmograph.

Photoelectric Plethysmograph

The photoelectric pulse plethysmograph using either transmittance or incidence light measures mainly dermal and hypodermal blood flow. This contrasts with the digital pulse inductive plethysmograph, oscillometric plethysmograph, piezoelectric sensor, and strain gauge that measure global digital blood flow. This distinction may be important in assessing follow-up of effects of external addition of pulses to the circulation as vasodilator treatment for Raynaud's phenomenon.

Pulse Oximeter

The pulse waveform from this device is a variant of the photoelectric plethysmograph

Impedance Plethysmograph

This method is technically complex to set-up as a means to record the digital pulse.

Capacitance Condenser Microphone

This is also called the Infraton pulse pick-up. It cannot provide amplitude calibration in cm but accurately depicts pulse waveform and is simple to apply.

Electronic Pneumoplethysmography

This device consists of an air-filled cup method that can be calibrated to volume. It is technically difficult to set-up and is utilized only in a laboratory setting.

Systemic Arterial Pulse-Dicrotic Notch

Neck Inductive Plethysmograph

The neck inductive plethysmograph (U.S. Pat. No. 4,986,277—Method And Apparatus For Non-Invasive Monitoring Of Central Venous Pressure, Inventor Marvin A. Sackner; U.S. Pat. No. 5,040,540—Method And Apparatus For Non-InvasiveMonitoring Of Central Venous Pressure, And Improved Transducer Therefor, Inventor: Marvin A. Sackner) can be used to obtain the carotid arterial waveform. As with the digital pulse plethysmograph, during external addition of pulses to the circulation, it is necessary to record this parameter with an electrocardiograph. To compute the dicrotic notch ratio and Augmentation Index, markers of nitric oxide effect, during external addition of pulses to the circulation, it is necessary to filter them from the fundamental digital pulse wave since they distort the pulse waveform. The removal of added pulses is accomplished by digital band pass filtering and ensemble averaging of several heartbeats of the digital pulse wave from an R-wave trigger of the electrocardiogram. The averaged digital pulse wave is displayed without the externally added pulses and allows identification of the dicrotic notch and computation of the Augmentation Index. The b/a ratio is the height from upward inflection point of the dicrotic notch of the pulse to its end-diastolic level divided by the total height of the digital pulse tracing. In the presence of normal endothelial function, the external addition of pulses to the circulation increases this ratio due to vasodilation as a result of nitric oxide release. The frequency, amplitude of added pulses, and peak acceleration of the added pulses devices plotted against the b/a ratio provides graphs of dose-response curves.

The height from the upward deflection point of the dicrotic notch to the end-diastolic level divided by the total height of carotid pulse tracing can be computed (b/a ratio). The b/a ratio is lower in hypertensive patients than normal controls because the dicrotic notch moves upward on the diastolic limb of the pulse. Ascending aortic wall sclerosis is advanced in hypertension. The b/a ratio measured by carotid pulse tracing is a useful indicator in evaluating the ascending aortic wall distensibility in hypertension. Long-term treatment with added pulses to the circulation bring both the b/a ratio and aortic distensibility to normal values.

Applanation Tonometry

This technique consists of the operator pressing a probe that has a strain gauge sensor at its tip (Millar) over an artery, e.g., radial, brachial, carotid, subelavian, femoral with sufficient but not excessive pressure to display the arterial pulse.

Systemic Pressure Pulse

Chadwick RS et al. (Pulse-wave model of brachial arterial pressure modulation in aging and hypertension. Am. J. Physiol 1986;251:H1–11.) found that upward modulation of the brachial arterial dicrotic notch occurs after vasoconstriction with phenylephrine and downward with nitroglycerin in virtually all subjects. Pretreatment with atropine to prevent heart rate changes does not alter modulation of the dicrotic notch after phenylephrine or nitroglycerin. Atropine alone moves the dicrotic notch downward. In a few cases with combined atropine and nitroglycerin, the dicrotic notch moved so far away from the main wave that the dicrotic notch was lost in the subsequent main wave. Therefore, the latter must be taken into account when the dicrotic notch is low on the diastolic limb at baseline prior to any eNOS upregulation. The ascending aorta also shows downward descent of the dicrotic notch after nitroglycerin administration (Laskey WK, Kussmaul WG. Arterial wave reflection in heart failure. Circulation 1987;75:71 1–22).

Digital and Systemic Arterial Distensibility

During drug induced rises or falls in blood pressure within the first 5 heart beats, the carotid artery diameter, measured with ultrasound, decreased with nitroglycerin and increased with phenylephrine. The analogue trace reveals that as phenylephrine increased blood pressure on a beat by beat basis, the dicrotic notch of the arterial diameter moved upward on the arterial diameter trace and the Augmentation Index increased. Distensibility (2×systolic diameter−diastolic diameter/diastolic diameter×pulse pressure) decreased with phenylephrine and increased with nitroglycerin. Computation of distensibility requires an imaging device such as doppler ultrasound that captures changes of arterial diameter of a peripheral artery with each cardiac cycle.

Pulse Wave Velocity

The pulse wave velocity is obtained by dividing the distance between two remote arterial sites with the difference in time of onset of the two remote arterial waveforms. It is most accurately measured in descending order with applanation tonometry, imaging, or plethysmographic methods. It increases as a function of age. The external addition of pulses to the circulation through release of nitric oxide in normal vascular endothelium causes diminution of arterial stiffness with consequent slowing of pulse wave velocity. As with digital pulse waveform analysis, it is necessary to remove the externally added pulses from the two pulse waveforms displays by combination of digital bandpass filtering and electrocardiographic R-wave triggering for ensemble averaging. The pulse wave velocity is inversely proportional to arterial stiffness, e.g., the stiffer the arterial system, the faster the pulse wave velocity and vice-versa.

External addition of pulses to the circulation in the presence of normal endothelial function lengthens pulse wave velocity because nitric oxide release lessens arterial stiffness. As with the dicrotic notch and Augmentation Index, dose response curves can be constructed and compared to nitroglycerin response or to a normal control population. External addition of added pulses in the presence of endothelial dysfunction produces a diminished or absent change in pulse wave velocity since arterial stiffness and endothelial dysfunction are highly correlated variables.

Extremity Blood Flow

The forearm is the standard site for sensing changes in blood flow during endothelial dependent or independent vasodilation, e.g., nitric oxide release, reactive hyperemia, acetylcholine injection or nitroglycerin administration, respectively. Blood flow is measured by means of the venous occlusion method employing mercury in silastic or rubber strain gauges or limb inductive plethysmograph sensors. It also is measured directly using doppler imaging of the arterial blood vessel.

External addition of pulses to the circulation in the presence of normally functioning endothelium releases nitric oxide that causes vasodilation and increased forearm blood flow. The blood flow response is reduced in endothelial dysfunction. Dose response curves as described for the dicrotic notch of the digital pulse can be obtained in like manner for forearm blood flow.

Central Venous Pressure

Bedside estimation of the height at which the internal jugular veins collapse, referenced to a standard hemodynamic location, reflects central venous pressure (CVP). This phenomenon can be utilized to make this measurement with the neck inductive plethysmograph (NIP) (U.S. Pat. Nos. 4,986,277 and 5,040,540), a technology that simultaneously records several events in the neck including changes in pleural pressure due to respiration, contraction of neck muscles, internal jugular venous waveform and carotid arterial waveforms. In order to obtain the measurement in a resting subject, the respiratory distortion of these vascular waveforms is first eliminated or minimized by employing a digital bandpass filter, thereby allowing identification of the venous and arterial waveforms on the videoscreen of a personal computer. The upper torso is positioned above the horizontal while observing the videoscreen until the vascular waveform is seen as a mixed arteriovenous waveform, signifying intermittent internal jugular venous collapse. It is at this point that the height of the internal jugular vein above the phlebostatic axis is obtained by external measurement and recorded as CVP in cm $H_2O$.

During periods of induced added vascular pulses on the internal jugular venous or carotid arterial waveforms of NIP, it becomes almost impossible to discern the difference between the two pulses to allow an estimate of CVP. This measurement ca only be employed immediately after cessation of the externally added pulses to the circulation.

Since the major effect of induced added vascular pulses is to effect release of nitric oxide from vascular endothelium, the action on CVP is that of nitric oxide, a molecule that reduces CVP depending upon state of hydration to as much as 50% of the baseline value. In patients with stable coronary artery disease, intravenous nitroglycerin reduced central venous pressure from 4.7 mm Hg to 1.7 mm Hg. Organic nitrates and nitroglycerin ointment reduce central venous pressure in patients with acute myocardial infarction. For isosorbide dinitrate, CVP fell from 9 to 5.5 cm $H_2O$ and for nitroglycerin ointment from 8.4 to 4 cm $H_2O$.

External addition of pulses added to the circulation in the presence of normal endothelial function causes central venous pressure to decrease. This fall can quantified by noting the change in angle of the body to the horizontal when an ensemble averaged display of the neck inductive plethysmograph shows transition of an arterial pulse waveform to a venous pulse waveform immediately after cessation of the external addition of pulses to the circulation. As with the dicrotic notch of the digital pulse, dose response curves can be constructed. External addition of pulses to the circulation in the presence of endothelial dysfunction causes no or little decrease of central venous pressure.

Thoracocardiograph

The thoracocardiograph is an inductive plethysmographic method that captures the left ventricular volume curve (U.S. Pat. No. 5,178,151 Sackner M A: System for non-invasive detection of changes of cardiac volumes and aortic pulses, hereby incorporated by reference). Its appearance corresponds to curves obtained with radioangioraphy, nuclear angiography, and automated border edge echocardiography. The mathematical derivative of the thoracocardiograph ventricular volume curve closely resembles transmitral flow curves obtained with echo-doppler instruments.

Diastolic Cardiac Function

E/A ratios from the mathematical derivative of the thoracocardiograph ventricular waveform and Doppler echocardiography of transmitral blood flow are significantly correlated (R=0.53) despite differences in measurement site, i.e., ventricular wall and mitral valve. Both methods provide identical trends of changes in E/A ratios with interventions in 50 of 66 (76%) comparisons. Therefore, thoracocardiography reflects characteristics of left ventricular filling similar to Doppler echocardiography. The deceleration time of the E wave also inversely correlates with the pulmonary capillary wedge pressure and directly correlates with impaired diastolic relaxation.

Normal myocardial endothelial function is associated with normal diastolic function whereas myocardial endothelial dysfunction is associated with diastolic dysfunction. Early diastolic dysfunction is marked by prolongation of deceleration time because of impaired or slowed left ventricular relaxation. With disease progression, left ventricular compliance decreases, causing increased in left atrial pressure, increased E wave velocity and decreased deceleration time, thus mimicking a normal pattern. In normal subjects, Nitroglycerin, a nitric oxide donor, decreases both E and A wave velocity and prolongs deceleration time. E/A ratio decreases or remains unchanged. Diseased hearts with a "pseudonormal" pattern demonstrate a similar decline in E wave velocity but less or no decline in A wave velocity producing a decreased E/A ratio with an impaired relaxation pattern. Patients with markedly reduced ventricular compliance and severely restricted filling may or may not have the ability to alter their filling pattern depending on LV operating chamber compliance. However, when nitroglycerin acts on such hearts, deceleration time is lengthened toward normal values. Failure to revert to "pseudonormal" pattern with reduction of preload through nitroglycerin in patients with restrictive filling is associated with poor prognosis External addition of pulses to the circulation can be used to test the preceding possibilities using nitric oxide release from myocardial endothelium as analogous to nitroglycerin with the derivative of TCG as the dose-responsive measure. It is necessary to utilize digital bandpass filtering and electrocardiographic R wave triggering for ensemble averaging immediately after cessation of the external addition of pulses to the circulation therapy because the measure cannot be obtained during the treatment. There is no measure of the mathematical derivative of TCG that is specific for nitric oxide effect but diminution of E/A ratio and lengthening of deceleration time generally change with normal myocardial endothelium because these measures reflect pulmonary capillary wedge pressure. Nitric oxide's major effect is to diminish cardiac preloading through venous relaxation. This is marked by significant falls, e.g., up to 50% from baseline, in both pulmonary capillary wedge and central venous pressures. If the deceleration time is lengthened because of diastolic dysfunction, then it will decrease after repetitive treatments although with a single or a few treatment, there may be little or no change in the E/A ratio or deceleration time of the E wave.

Arterial Compliance Measured by Ultrasound-Doppler

Arterial compliance is the slope of change in diameter measured with ultrasound Doppler imaging to the change in pressure measured with digital blood pressure (Finapres) during diastole. Arterial compliance increases with nitric oxide released from normally functioning endothelium and shows little or no change when there is endothelial dysfunction.

External addition of pulses increases arterial compliance in the presence of normally functioning endothelium and does not change it or increases it to a lesser extent than the normal response in the presence of endothelial dysfunction when the measurement is carried out immediately after cessation of the externally added pulses to the circulation.

Biochemical Tests

Serum or Plasma Nitrate/Nitrite

In anesthetized piglets placed on a motion platform that oscillated headwards to footwards at a frequency of 4 Hz and a force of ~0.4 G, regional blood flows, as assessed by colored microspheres, were increased by pGz, relative to values obtained before pGz Adams et al. Regional Blood Flow during Periodic Gz Acceleration. Crit. Care Med. October 2001). Blood flow (ml/min/100 g) significantly increased to the epicardium (71%), endocardium (93%), cerebrum (183%), brain stem (177%), renal cortex (53%), ileal mucosa (69%), gastric antral mucosa (72%), and liver (86%). The blood flows returned to baseline 10 min after discontinuation of pGz, except in the myocardial layers where blood flow remained significantly elevated. There was no difference compared to baseline in heart rate, arterial blood gases and blood pressure, but serum nitrite concentration was significantly higher (58%) during pGz.

In humans, circulating nitrite represents an attractive estimate of regional endothelial NO formation, whereas nitrate, with some caution, appears useful in estimating overall nitrogen/NO turnover. There is a linear relationship between forearm blood flow and venous plasma nitrite+nitrate and between L-citrulline in an exercising arm. Venous plasma levels of nitrite+nitrate and L-citrulline in the non-exercising arm do not change. Thus, exercise-induced forearm vasodilation correlates with forearm plasma levels of nitrite+nitrate and L-citrulline, as in vivo markers of NO production. In another group of healthy adults, acetylcholine, an endothelium dependent vasodilator, dose-dependently increased resting forearm blood flow (from 3.0+/−0.3 to 10.4+/−0.9 ml/min per 100 ml tissue) and serum nitrite concentration (from 402+/−59 to 977+/−82 nmol/l, both p<0.05). A significant correlation was observed between the changes in forearm blood flow and the serum nitrite concentration (r=0.61, p<0.0001). L-NMMA, an agent that inhibits nitric oxide release by eNOS reduced resting forearm blood flow and endothelium-dependent vasodilation by 30% and this was paralleled by a significant reduction in serum nitrite concentration at the highest dose of acetycholine (p<0.001). Thus, plasma nitrite/nitrite levels can be used as biochemical markers of effectiveness of external addition of pulses to the circulation.

Therefore, the concentration of plasma nitrite/nitrate sensitively reflects changes in endothelial nitric oxide formation and can be used to measure effectiveness of treatment with external addition of pulses to the circulation.

Serum L-Citrulline

The level of this metabolic product of nitric oxide correlates with levels of forearm exercise and can be used as a biochemical test of effectiveness of external addition of pulses to the circulation.

Serum Nitric Oxide

This measure is reported much less frequently than plasma nitrite/nitrate levels. It utilizes a nitric oxide specific electrode or chemiluminescent technique.

Tissue-Type Plasminogen Activator

External addition of pulses to the circulation releases t-PA from vascular endothelium that causes an incremental increase of plasma t-PA. In treatment situations where a desired level of t-PA is an end-point, this parameter can be measured in plasma. Patients with endothelial dysfunction as in hypertension do not release t-PA to the same extent as normal subjects.

Blood Coagulation Tests

In patients with acute myocardial infarction or stroke, recombinant tissue plasma tissue activator (rt-PA) moderately decreases fibrinogen and fibrinogen degradation products. Therefore, the integrity of the vascular endothelium can be checked indirectly by measuring these parameters after external addition of pulses to the circulation. In addition, measurement of these parameters allows titration of treatment effectiveness in situations where the end-point is a desired level of fibrinolysis.

V. Diagnoses Using Mediators Produced by External Pulses

Atherosclerosis

Patients with atherosclerosis have endothelial dysfunction marked by impaired endothelium dependent vasodilator response.

External addition of pulses to the circulation reveals impaired nitric oxide release that can be detected by a variety of non-invasive hemodynamic tests as described below. The preferred test involves the digital pulse plethysmograph using the inductive plethysmograph as the sensor. Values of the Augmentation Index and the position of the dicrotic notch in the digital pulse are compared to normal subjects in order to ascertain whether nitric oxide release is impaired.

Hypertriglyceridemia

Patients with high triglyceride (of which very low density lipoproteins [VLDL] are the main carriers), but with normal low density lipoprotein (LDL) cholesterol levels, have impaired endothelium dependent vasodilator response.

External addition of pulses to the circulation reveals impaired nitric oxide release that can be detected by a variety of non-invasive hemodynamic tests as described below. The preferred test involves the digital pulse plethysmograph using the inductive plethysmograph as the sensor. Values of the Augmentation Index and the position of the dicrotic notch in the digital pulse are compared to normal subjects in order to ascertain whether nitric oxide release is impaired.

Systemic Hypertension

Studies of hypertensive patients indicate that depression of eNOS activity is linked with end-organ disease and is more common in salt-sensitive models of hypertension. The latter are more prone to develop left ventricular hypertrophy and renal disease. eNOS activity in response to hypertension might be genetically determined. Heterogenicity may partially explain the different rates of occurrence of end-organ disease in humans with hypertension of similar severity.

Testing for nitric oxide dose response to external addition of pulses to the circulation classifies hypertensives at higher risk to end-organ disease. External addition of pulses to the circulation reveals impaired nitric oxide release that can be detected by a variety of non-invasive hemodynamic tests as described below. The preferred test involves the digital pulse plethysmograph using the inductive plethysmograph as the sensor. Values of the Augmentation Index and the position of the dicrotic notch in the digital pulse are compared to normal subjects in order to ascertain whether nitric oxide release is impaired.

Hypercholesterolemia

Patients with hypercholesterolemia have impaired endothelium dependent vasodilator response.

External addition of pulses to the circulation reveals impaired nitric oxide release that can be detected by a variety of non-invasive hemodynamic tests as described below. The preferred test involves the digital pulse plethysmograph using the inductive plethysmograph as the sensor. Values of the Augmentation Index and the position of the dicrotic notch in the digital pulse are compared to normal subjects in order to ascertain whether nitric oxide release is impaired.

Insulin Resistance Syndrome

Insulin resistance syndrome (IRS), also termed "syndrome X," is a distinctive constellation of risk factors for the development of type 2 diabetes mellitus and cardiovascular disease. The syndrome's hallmarks are glucose intolerance, hyperinsulinemia, a characteristic dyslipidemia (high triglycerides; low high-density lipoprotein cholesterol, and small, dense low-density lipoprotein cholesterol), obesity, upper-body fat distribution, hypertension, and increased prothrombotic and antifibrinolytic factors. There is a significant association between endothelial dysfunction and insulin resistance in normoglycemic, young first-degree relatives of type-2 diabetes mellitus patients independent of the classic cardiovascular risk factors. Therefore, noninvasive measurement of endothelial dysfunction provides early identification of high-risk for atherosclerosis in subjects with a family history of type-2 diabetes.

External addition of pulses to the circulation in patients with Insulin Resistance Syndrome or normotensive, normoglycemic, non-hypercholesterolemic, first degree relatives of patients with type-2 diabetes reveals impaired nitric oxide release that can be detected by a variety of non-invasive hemodynamic tests as described below. The preferred test involves utilizing the digital pulse plethysmograph using the inductive plethysmograph as the sensor. Values of the Augmentation Index and the position of the dicrotic notch of the digital pulse are compared to normal subjects in order to ascertain whether nitric oxide release is impaired.

Arterial Smooth Muscle Dysfunction

Impaired endothelium-dependent vasodilation has been demonstrated in various vascular beds of different animal models of diabetes and in humans with type 1 and 2 diabetes. Several mechanisms of endothelial dysfunction have been reported, including impaired signal transduction or substrate availibility, impaired release of nitric oxide, increased destruction of nitric oxide, enhanced release of endothelium-1 and decreased sensitivity of vascular smooth muscle to nitric oxide (arterial smooth muscle dysfunction). The principal mediators of hyperglycemia-induced endothelial dysfunction might be activated protein kinase C, increased activity of the polyol pathway, non-enzymatic glycation and oxidative stress. Correction of these pathways, as well as administration of ACE inhibitors and folate, improves endothelium-dependent vasodilation in diabetes.

External addition of pulses to the circulation reveals impaired nitric oxide release or there is decreased sensitivity of vascular smooth muscle to nitric oxide. These conditions are detected by a variety of non-invasive hemodynamic tests as described below. The preferred test involves the digital pulse plethysmograph using the inductive plethysmograph as the sensor. Values of the Augmentation Index and the position of the dicrotic notch of the digital pulse are compared to normal subjects in order to ascertain whether nitric oxide release is impaired or there is decreased sensitivity of vascular smooth muscle to nitric oxide.

Microvascular Cerebral Disorders and Normal Pressure Glaucoma

The vascular reactivity to breathing carbon dioxide represents a widely used method to diagnose microvascular cerebral disorders. After exposure to carbon dioxide, the visual fields improve in patients who showed significant increase in ocular pulse amplitudes.

This phenomenon also occurs in some pressure glaucoma patients, i.e., significant increase of ocular pulse amplitudes and improvement of the central visual field. These phenomena are believed to be due to baseline ocular vasospasm, reversed by the vasodilator action of carbon dioxide. External addition of pulses to the circulation that releases nitric oxide from ocular arterial endothelium substitutes for carbon dioxide in vasodilating ocular vasospasm thereby allowing improvement in the visual field.

Baroreceptor Testing

Since external addition of pulses to the circulation stimulates endothelial release of nitric oxide, this method can be used to test integrity of barorceptors provided nitric oxide is released as determined by change in position of dicrotic notch of the digital pulse plethysmograph (b/a ratio). This application is a surrogate for nitroglycerin administration that causes a decrease in blood pressure followed by compensatory rise in heart rate from baroreceptor activation. The latter is impaired in atherosclerosis, diabetes, chronic heart failure, and smoking. The limitation of this method is that these conditions might also be complicated with endothelial dysfunction such that insignificant amounts of nitric oxide might be released in response to the added pulses.

During drug induced rises or falls in blood pressure within the first 5 heart beats, the carotid artery diameter, that was measured with ultrasound, decreased with nitroglycerin and increased with phenylephrine. Phenylephrine an alpha sympathetic agonist causes the the dicrotic notch of the arterial diameter to move upward on the arterial diameter trace and increases the augmentation index. Distensibililty (2×sys−diast diameter/diastolic diameter×pulse pressure) decreases with phenylephrine and increases with nitroglycerin. Plots of RR intervals against systolic arterial diameter correlated better than systolic blood pressure in term of baroreceptor sensitivity. During drug-induced changes in blood pressure, baroreceptor activity in humans is influenced more by passive stretch than by local smooth muscle contraction.

The fact that changes of systolic diameter arterial diameter correlate well with RR intervals as an index of baroreceptor sensitivity is the basis for the new findings that change in rate of arterial diameter correlate even better with RR intervals as a measure of baroreceptor sensitivity. Thus, Kornet et al (Physiologist 2000) reported that an increase in distension rate variability, i.e., increase in diameter during the cardiac cycle per systolic rise time of the carotid artery is superior to systolic digital blood pressure as a predictor of RR interval variability in assessment of baroreceptor function by the sequence method. Since the digital pulse plethysmograph measures change in cross-sectional area of the digital artery that is in turn a function of arterial diameter, and its upstroke time is analogous to the carotid rise time, it can utilized as a substitute for measuring baroreflex sensitivity using the sequence method.

Therefore, baroreceptor testing utilizing externally added pulses to change arterial stiffness through endothelial nitric oxide release and the plotting RR intervals of the electrocardiogram against the rate of arterial distension is applicable to detecting early abnormalities in atherosclerosis, diabetes, chronic heart failure, and smoking as an aid to prognosis and follow-up. Standard means for detecting baroreceptor activity using blood pressure and heart rate can also be obtained immediately after cessation of the external addition of pulses application.

Test of Endothelial Function for Selection of External Induction of Pulses Treatment In patients in whom treatment with endothelial released nitric oxide might be beneficial but where eNOS upregulation is not acutely possible because of acquired or genetic defects, external addition of pulses with analysis of the digital pulse wave provides a rapid, screening means to determine efficacy of endothelial dependent vasodilation. This helps to decide as to whether it is best to treatment with externally added pulses or chose a nitric oxide donor drug with endothelial independent vasodilator properties. For example, in ischemic stroke following middle cerebral artery occlusion, nitric oxide released from eNOS limits the extent of the stroke. But if eNOS is absent or severely downregulated, agents that acutely upregulate or prolong its action may be ineffective. Here a nitric oxide donor drug that has endothelial independent vasodilator properties should be administered.

The invention is not limited by the embodiments described above which are presented as examples only but can be applied and modified in various ways within the scope of protection defined by the appended patent claims.

We claim:

1. A method of medical treatment for a patient with a body, comprising the steps of:
   providing a periodic acceleration means for periodically accelerating one of the body and at least one part thereof to externally and non-invasively add a pulse to the body's fluid filled channels over the body's own pulse; and
   treating a disease, condition, or injury of the patient that is treatable by at least one endothelial released mediator by adding pulses, using the periodic acceleration means, to the body's fluid filled channels over the body's own pulse, thereby stimulating endothelial release of beneficial mediators and suppressing non-beneficial mediators;
   wherein the periodic acceleration means comprises a reciprocating movement platform which periodically accelerates the one of the body and at least one part thereof in a headwards-footwards direction at a frequency between about 1 Hz and about 6 Hz.

2. The method of medical treatment as recited claim 1, further comprising the step of:
   using the periodic acceleration means to control the frequency and intensity of said pulses.

3. The method of medical treatment as recited claim 1, wherein the step of adding pulses, using the periodic acceleration means, to the body's fluid filled channels over the body's own pulse comprises:
   adding pulses, using the periodic acceleration means, over the body's own pulse to at least one of the vascular circulation, heart, lymphatics, interstitial spaces, and bone interstices.

4. The method of medical treatment as recited in claim 1, further comprising the step of:
   repeatedly adding pulses, using the periodic acceleration means, to the body's fluid filled channels over the body's own pulse such that even during periods when pulses are not imparted, bioavailability of the beneficial mediators is greater than in the pretreatment period.

5. The method of medical treatment as recited in claim 1, wherein the step of adding pulses, using the periodic acceleration means, to the body's fluid filled channels over the body's own pulse comprises the step of:
   adding pulses, using the periodic acceleration means, to the body's fluid filled channels over the body's own pulse, thereby stimulating endothelial release of at least one of nitric oxide, prostacyclin, tissue plasminogen activator (t-PA), endothelial dependent hyperpolarizing factor (EDHF), endothelial dependent relaxing factor, endothelial growth factors, and transcription genes.

6. The method of medical treatment as recited in claim 1, wherein the step of adding pulses, using the periodic acceleration means, to the body's fluid filled channels over the body's own pulse comprises the step of:
   modulating vascular endothelial growth factor (VEGF).

7. The method of medical treatment as recited in claim 1, wherein the step of adding pulses, using the periodic acceleration means, to the body's fluid filled channels over the body's own pulse comprises the step of:
   adding pulses, using the periodic acceleration means, to the body's fluid filled channels over the body's own pulse, thereby suppressing at least one of endothelins, tissue plasminogen antigens, and tissue plasminogen inhibitors.

8. The method of medical treatment as recited in claim 1, wherein the step of adding pulses, using the periodic acceleration means, to the body's fluid filled channels over the body's own pulse comprises the step of:
   adding pulses, using the periodic acceleration means, to the body's fluid filled channels over the body's own pulse, thereby stimulating endothelial release of at least one of Cu/Zn superoxide dismutase, prostacyclin synthesis-related enzymes cyclooxygenases (COX-1 and COX-2), prostacyclin synthase (PGS), and thromboxane synthase (TXS).

9. The method of medical treatment as recited in claim 1, wherein the step of adding pulses, using the periodic acceleration means, to the body's fluid filled channels over the body's own pulse comprises the step of:

adding pulses, using the periodic acceleration means, to the body's fluid filled channels over the body's own pulse, thereby stimulating endothelial release of at least one of metabolites prostaglandin (PGI(2)) and thromboxane (TXA(2)) in endothelial cells.

10. The method of medical treatment as recited in claim 1, wherein the step of providing a periodic acceleration means for periodically accelerating one of the body and at least one part thereof comprises the step of:
providing a periodic acceleration means for pulsing with a periodic acceleration up to about ±0.6 g.

11. The method of medical treatment as recited in claim 10, wherein the step of providing a periodic acceleration means for periodically accelerating one of the body and at least one part thereof comprises the step of:
providing a periodic acceleration means for periodically accelerating one of the body and at least one part thereof to externally and non-invasively add a pulse to the body's fluid filled channels over the body's own pulse such that the added pulses are visible over the patient's own pulse waveform on a vascular pulse waveform trace display.

12. The method of medical treatment as recited in claim 1, wherein the step of providing a periodic acceleration means for periodically accelerating one of the body and at least one part thereof comprises the step of:
providing a reciprocating movement platform for shifting the patient to and fro in headwards-footwards direction using a horizontal platform driven by a controllable fly wheel-motor mechanism.

13. The method of medical treatment as recited in claim 12, wherein the step of providing a periodic acceleration means for periodically accelerating one of the body and at least one part thereof comprises the step of:
providing a means for fixing the patient to the movement platform with a vertical foot-board along with attachments to immobilize at least one of the feet and legs such that movement which is transmitted by the platform is conveyed to the patient without substantial out-of-phase body movement relative to platform movement.

14. The method of medical treatment as recited in claim 1, wherein the step of providing a periodic acceleration means for periodically accelerating one of the body and at least one part thereof comprises the step of:
providing a seat within a wheel chair driven by an adjustable frequency movement means, wherein the adjustable frequency movement means comprises a cam adjustable for vertical displacement and one of a rotary motor mechanism and a flywheel drive motor assembly.

15. The method of medical treatment as recited in claim 1, wherein the step of providing a periodic acceleration means for periodically accelerating one of the body and at least one part thereof comprises the step of:
providing a means for shifting the patient's legs up and down while the patient is seated, the means for shifting comprising an adjustable frequency, cam adjustable for vertical displacement, rotary motor mechanism.

16. The method of medical treatment as recited in claim 1, wherein the medical treatment is for a prospective donor of at least one organ for transplantation; and wherein the step of adding pulses, using the periodic acceleration means, to the body's fluid filled channels over the body's own pulse causes endothelial release of nitric oxide, prostacyclin, and tissue plasminogen activator and suppression of endothelin-1, tissue plasminogen inhibitor and antigen thereby helping to prevent graft rejection.

17. The method of medical treatment as recited in claim 16, further comprising the step of:
dosing the patient with phosphodiesterase inhibitors.

18. The method of medical treatment as recited in claim 16, further comprising the step of:
preserving the at least one organ after the donor dies.

19. The method of medical treatment as recited in claim 1, wherein the medical treatment is for depressive reactions, chronic fatigue syndrome, panic and generalized anxiety disorder, schizophrenia, conversion and somatoform pain disorder, and alcohol abuse and dependence.

20. The method of medical treatment as recited in claim 1, wherein the step of providing a periodic acceleration means for periodically accelerating one of the body and at least one part thereof comprises the step of:
providing a means to utilize high frequency oscillatory ventilation with bias flow and added apparatus dead space which adds pulses to the body's fluid channels through the lungs.

21. The method of medical treatment as recited in claim 1, wherein the step of adding pulses, using the periodic acceleration means, to the body's fluid filled channels over the body's own pulse comprises the step of:
adding pulses, using the periodic acceleration means, to the body's fluid filled channels over the body's own pulse to thereby add pulses over the body's own pulse to the body's fluid filled channels, thereby stimulating endothelial release of beneficial mediators and suppress non-beneficial mediators, such that the pulses do not entrain to the patient's own pulse wave.

22. The method of medical treatment as recited in claim 1, wherein the beneficial mediator is nitric oxide, further comprising the step of:
testing a response of the patient by at least one of analyzing a dicrotic notch present on a diastolic limb of an arterial pulse, analyzing an Augmentation Index of the patient's arterial pulse, analyzing arterial pulse wave velocity, analyzing central venous pressure, analyzing E wave deceleration time, analyzing peripheral blood flow, utilizing biochemical markers, and utilizing blood coagulation tests.

23. The method of medical treatment as recited in claim 1, wherein the beneficial mediator is nitric oxide, further comprising the step of:
testing a response of the patient by utilizing biochemical markers, wherein the biochemical markers are released as products or metabolites from endothelial tissue and comprise at least one of serum nitric oxide, nitrite/nitrates, tissue plasminogen activator (tPA), and prostacycline.

24. The method of medical treatment as recited in claim 1, further comprising the step of:
dosing the patient with a drug;
wherein the combination of dosing and providing pulses is for at least one of potentiating an effect of the drug, limiting the dosing of the drug, minimizing unwanted side effects, and obtaining unique beneficial effects of a combination of dosing and pulsing.

25. The method of medical treatment as recited in claim 24, wherein the drug is at least one of L-Arginine, insulin, an angiotensin converting enzyme (ACE) inhibitor, an angiotensin II receptor blocker, Angiotensin-(1-7), aspirin, an iloprost, a beta blocker, a calcium antagonist that upregulate the activity of superoxide dismutase, statin, an estrogen, an atrial natriuretic peptide, an intravenous clot buster, phosphodiesterase inhibitor-3 or -4 or -5, a xanthine oxidase inhibitor, an endothelin receptor antagonist, SC52608 (a synthesized superoxidase dismutase mimic), a platelet aggregation inhibitor, a furoxins or S-nitrosothiol derivative that releases nitric oxide slowly, and a prostaglandin; and wherein the step of adding pulses, using the periodic acceleration means, to the body's fluid filled channels over the body's own pulse, in conjunction with the step of dosing the patient with the drug, provides at least one of additive and synergistic vasodilator, antiplatelet aggregation and antileukocyte adhesion actions.

26. The method of medical treatment as recited in claim 25, wherein the calcium antagonist that upregulates the activity of superoxide dismutase is pranidipine.

27. The method of medical treatment as recited in claim 25, wherein the platelet aggregation inhibitor is YC-1.

28. The method of medical treatment as recited in claim 25, wherein the intravenous clot buster is recombinant tPA.

29. The method of medical treatment as recited in claim 24, wherein the drug is a statin; and wherein the step of adding pulses, using the periodic acceleration means, to the body's fluid filled channels over the body's own pulse, in conjunction with the step of dosing the patient with the drug, provides at least one of additive and synergistic vasodilator, antiplatelet aggregation, antileukocyte adhesion actions and bone building.

30. The method of medical treatment as recited in claim 24, wherein the medical treatment is for Alzheimer's disease and the drug is a monamine oxidase-B inhibitor, L-deprenyl.

31. The method of medical treatment as recited in claim 24, wherein the medical treatment is for at least one of acute brain injury and a chronic neurogenerative disease, and the drug is a nitric oxide synthase (NOS) inhibitor.

32. The method of medical treatment as recited in claim 31, wherein the acute brain injury comprises one of stroke and brain contusion.

33. The method of medical treatment as recited in claim 31, wherein the chronic neurodegenerative disease comprises one of Parkinson's disease, Huntington's disease, Alzheimer's disease, amyotrophic lateral sclerosis, and multiple sclerosis.

34. The method of medical treatment as recited in claim 31, wherein the NOS inhibitor is one of macrophage or smooth muscle inducible NOS (iNOS) and neuronal NOS (nNOS) inhibitor.

35. The method of medical treatment as recited in claim 34, wherein the iNOS inhibitor is one of 1400 W, aminoguanidine, radicicol, L-NIL, and interferon-β.

36. The method of medical treatment as recited in claim 34, wherein the nNOS inhibitor is one of ARR17338 and ARL17477.

37. The method of medical treatment as recited in claim 24, wherein the medical treatment is to prevent the inflammatory consequences of hemorrhagic shock, the drug is both a macrophage or smooth muscle inducible NOS (iNOS) inhibitor and a scavenger of peroxynitrate; and wherein the step of adding pulses, using the periodic acceleration means, to the body's fluid filled channels over the body's own pulse, in conjunction with the step of dosing the patient with the drug, provides a useful adjunct to appropriate electrolyte and fluid balance.

38. The method of medical treatment as recited in claim 37, wherein the scavenger of peroxynitrate is mercaptoethylguanidine.

39. The method of medical treatment as recited in claim 24, wherein the medical treatment is for septic shock, and the drug is a macrophage or smooth muscle inducible NOS (iNOS) inhibitor; and wherein the step of adding pulses, using the periodic acceleration means, to the body's fluid filled channels over the body's own pulse, in conjunction with the step of dosing the patient with the drug, provides lower pulmonary vascular resistance.

40. The method of medical treatment as recited in claim 1, wherein the medical treatment is for the treatment of heart diseases, heart conditions, and heart disorders.

41. The method of medical treatment as recited in claim 40, wherein the heart diseases, conditions, and disorders comprise one of left ventricular hypertrophy, cardiac allograft, heart failure, diastolic dysfunction, and intracardiac thrombosis.

42. The method of medical treatment as recited in claim 1, wherein the medical treatment is for impaired lymphatic drainage; and wherein the step of adding pulses, using the periodic acceleration means, to the body's fluid filled channels over the body's own pulse causes sustained relaxation and dilation of lymph channels.

43. The method of medical treatment as recited in claim 42, further comprising the step of:

measuring volume changes by means of a limb plethysmograph in order to test the efficacy of the medical treatment.

44. The method of medical treatment as recited in claim 1, wherein the medical treatment is for promoting bone growth in states where mediator release is deficient; and wherein the step of adding pulses, using the periodic acceleration means, to the body's fluid filled channels over the body's own pulse causes release of nitric oxide and prostacyclin from bone osteoblasts.

45. The method of medical treatment as recited in claim 44, wherein the state where mediator release is deficient is osteoporosis.

46. The method of medical treatment as recited in claim 1, wherein the medical treatment is to provide at least one of cerebrospinal fluid drainage, vasodilation, and increased blood flow; and wherein the step of adding pulses, using the periodic acceleration means, to the body's fluid filled channels over the body's own pulse releases mediators from endothelial pia matter.

47. The method of medical treatment as recited in claim 1, wherein the medical treatment is for chronic heart failure; and wherein the step of adding pulses, using the periodic acceleration means, to the body's fluid filled channels over the body's own pulse upregulates endothelial nitric oxide synthase (eNOS) basal activity to release greater amounts of nitric oxide from dysfunctioning endothelium.

48. The method of medical treatment as recited in claim 1, wherein the medical treatment is for acute myocardial infarction; and wherein the step of adding pulses, using the periodic acceleration means, to the body's fluid filled channels over the body's own pulse upregulates endothelial nitric oxide synthase (eNOS) basal activity to release greater amounts of nitric oxide for at least one of coronary vasodilation, stimulating release of tPA from the endothelium to enhance myocardial reperfusion, and suppressing release of tPA inhibitors and antigens.

49. The method of medical treatment as recited in claim 1, wherein the medical treatment is for vasopathic angina; and
wherein the step of adding pulses, using the periodic acceleration means, to the body's fluid filled channels over the body's own pulse upregulates coronary vascular endothelial nitric oxide synthase (eNOS) to release nitric oxide thereby diminishing the frequency and intensity of coronary spasm episodes.

50. The method of medical treatment as recited in claim 1, wherein the medical treatment is for one of coronary atherosclerosis and asymptomatic coronary artery disease.

51. The method of medical treatment as recited in claim 1, wherein the medical treatment is for diastolic dysfunction; and
wherein the step of adding pulses, using the periodic acceleration means, to the body's fluid filled channels over the body's own pulse upregulates endothelial nitric oxide synthase (eNOS) in myocytes and endocardial endothelium to release nitric oxide thereby improving diastolic function.

52. The method of medical treatment as recited in claim 1, wherein the medical treatment is for systemic hypertension; and
wherein the step of adding pulses, using the periodic acceleration means, to the body's fluid filled channels over the body's own pulse downregulates endothelial release of endothelin-1 and upregulates endothelial nitric oxide synthase (eNOS) in endothelium to increase at least one of basal production of nitric oxide and genes that increase prostacyclin and tissue plasminogen activator (t-PA).

53. The method of medical treatment as recited in claim 1, wherein the medical treatment is for pulmonary hypertension; and
wherein the step of adding pulses, using the periodic acceleration means, to the body's fluid filled channels over the body's own pulse stimulates endothelial release of nitric oxide, prostacylin, and tissue plasminogen activator (t-PA), while suppressing endothelin-1 and tissue plasminogen inhibitor, in order to bring pulmonary arterial pressures down toward normal levels and inhibit thrombus formation.

54. The method of medical treatment as recited in claim 1, wherein the medical treatment is for Raynaud's phenomenon; and
wherein the step of adding pulses, using the periodic acceleration means, to the body's fluid filled channels over the body's own pulse stimulates endothelial release of nitric oxide, prostacyclin, and tissue plasminogen activator (t-PA), and suppresses endothelin-1 release.

55. The method of medical treatment as recited in claim 1, wherein the medical treatment is for proliferative retinopathy; and
wherein the step of adding pulses, using the periodic acceleration means, to the body's fluid filled channels over the body's own pulse upregulates endothelial nitric oxide synthase (eNOS) in endothelium and downregulates release of vascular endothelial growth factor from vascular endothelium.

56. The method of medical treatment as recited in claim 1, wherein the medical treatment is for insulin resistance syndrome; and
wherein the step of adding pulses, using the periodic acceleration means, to the body's fluid filled channels over the body's own pulse upregulates beneficial mediator release from vascular endothelium.

57. The method of medical treatment as recited in claim 1, wherein the medical treatment is for wide-angle glaucoma; and
wherein the step of adding pulses, using the periodic acceleration means, to the body's fluid filled channels over the body's own pulse upregulates beneficial mediator release from vascular endothelium.

58. The method of medical treatment as recited in claim 1, wherein the medical treatment is for macular degeneration; and
wherein the step of adding pulses, using the periodic acceleration means, to the body's fluid filled channels over the body's own pulse upregulates eNOS thereby effecting an increase of choroidal blood flow through the nitric oxide pathway.

59. The method of medical treatment as recited in claim 1, wherein the medical treatment is for angina pectoris; and
wherein the step of adding pulses, using the periodic acceleration means, to the body's fluid filled channels over the body's own pulse upregulates endothelial nitric oxide synthase (eNOS) of epicardial arteries and endothelial dependent hyperpolarizing factor release.

60. The method of medical treatment as recited in claim 1, wherein the medical treatment is for acute myocardial infarction and restenosis; and
wherein the step of adding pulses, using the periodic acceleration means, to the body's fluid filled channels over the body's own pulse stimulates endothelium to release nitric oxide, prostacyclin, and tissue plasminogen activator (t-PA); suppresses tissue plasminogen inhibitor; and inhibits activation of platelet fibrinogen receptors because of nitric oxide and prostacycline, thereby resulting in an action that is counter to thrombosis formation and propagation.

61. The method of medical treatment as recited in claim 60, further comprising:
dosing the patient with Platelet Glycoprotein GPIIb-IIIa Complex inhibitor.

62. The method of medical treatment as recited in claim 1, wherein the medical treatment is for a vasospastic angina; and
wherein the step of adding pulses, using the periodic acceleration means, to the body's fluid filled channels over the body's own pulse upregulates release of endothelial nitric oxide synthase (eNOS) of epicardial arteries, endothelial dependent hyperpolarizing factor, and tissue plasminogen activator (t-PA) in vasospastic arteries.

63. The method of medical treatment as recited in claim 1, wherein the medical treatment is for preparing the myocardium for redo coronary bypass graft surgery; and
wherein the step of adding pulses, using the periodic acceleration means, to the body's fluid filled channels over the body's own pulse upregulates release of endothelial nitric oxide synthase (eNOS), endothelial dependent hyperpolarizing factor, and tissue plasminogen activator (t-PA) in coronary arteries.

64. The method of medical treatment as recited in claim 1, wherein the medical treatment is for graft failure in coronary revascularization procedures; and
wherein the step of adding pulses, using the periodic acceleration means, to the body's fluid filled channels over the body's own pulse upregulates endothelial nitric oxide synthase (eNOS) for release of nitric oxide from endothelium as well as endothelial dependent hyperplolarizing factor and tissue plasminogen activator (t-PA) to prevent venous graft failure by maintaining patency.

65. The method of medical treatment as recited in claim 1, wherein the medical treatment is for type-2 diabetes mellitus; and wherein the step of adding pulses, using the periodic acceleration means, to the body's fluid filled channels over the body's own pulse stimulates endothelial release of nitric oxide, prostacyclin, and tissue plasminogen activator (t-PA) thereby improving the patient's coagulation profile.

66. The method of medical treatment as recited in claim 1, wherein the medical treatment is for preconditioning the patient's heart to minimize reperfusion injury in case myocardial ischemia or cardiac arrest should take place; and wherein the step of adding pulses, using the periodic acceleration means, to the body's fluid filled channels over the body's own pulse upregulates endothelial nitric oxide synthase (eNOS).

67. The method of medical treatment as recited in claim 1, wherein the medical treatment is for myocardial ischemia; and wherein the step of adding pulses, using the periodic acceleration means, to the body's fluid filled channels over the body's own pulse induces beneficial hibernation of the myocardium, thereby reducing myocardial oxygen consumption and improving regional myocardial function for any given level of myocardial blood flow, oxygen consumption and energetics.

68. The method of medical treatment as recited in claim 1, wherein the medical treatment is for obesity related hypertension; and wherein the step of adding pulses, using the periodic acceleration means, to the body's fluid filled channels over the body's own pulse upregulates endothelial release of nitric oxide and prostacyclin.

69. The method of medical treatment as recited in claim 1, wherein the medical treatment is for renal failure complicated by arterial stiffness; and wherein the step of adding pulses, using the periodic acceleration means, to the body's fluid filled channels over the body's own pulse upregulates endothelial release of nitric oxide, prostacyclin, and endothelial dependent hyperpolarizing factor, all of which diminish arterial stiffness, and increases renal blood flow, which has a diuretic effect.

70. The method of medical treatment as recited in claim 1, wherein the medical treatment is for chronic atrial fibrillation; and wherein the step of adding pulses, using the periodic acceleration means, to the body's fluid filled channels over the body's own pulse upregulates endothelial release of nitric oxide, prostacyclin, endothelial dependent hyperpolarizing factor and tissue plasminogen activator (tPA) from endothelium, all of which have fibrinolytic properties.

71. The method of medical treatment as recited in claim 1, wherein the medical treatment is for ischemic stroke; and wherein the step of adding pulses, using the periodic acceleration means, to the body's fluid filled channels over the body's own pulse increases cerebral blood flow through release of nitric oxide from vascular endothelium as well as prostacyclin and tissue plasminogen activator (tPA).

72. The method of medical treatment as recited in claim 1, wherein the medical treatment is for subarachnoid hemorrhage; and wherein the step of adding pulses, using the periodic acceleration means, to the body's fluid filled channels over the body's own pulse releases nitric oxide from vascular endothelium thereby relieving cerebral vasospasm.

73. The method of medical treatment as recited in claim 1, wherein the medical treatment is of a neonatal patient with neonatal pulmonary hypertension caused by a genetic deficiency of endothelial nitric oxide synthase (eNOS); and wherein the step of adding pulses, using the periodic acceleration means, to the body's fluid filled channels over the body's own pulse helps to restore eNOS and releases endothelial prostacylin, thereby reducing pulmonary hypertension and promoting closure of the patent ductus arteriosus.

74. The method of medical treatment as recited in claim 1, wherein the medical treatment is for bronchopulmonary dysplasia; and wherein the step of adding pulses, using the periodic acceleration means, to the body's fluid filled channels over the body's own pulse upregulates endothelial release of nitric oxide and prostacyclin thereby alleviating secondary pulmonary hypertension.

75. The method of medical treatment as recited in claim 1, wherein the medical treatment is for pulmonary embolism; and wherein the step of adding pulses, using the periodic acceleration means, to the body's fluid filled channels over the body's own pulse releases nitric oxide, prostacyclin, tissue plasminogen activator (tPA) and endothelial dependent hyperpolarizing factor.

76. The method of medical treatment as recited in claim 1, wherein the medical treatment is for portal hypertension; and wherein the step of adding pulses, using the periodic acceleration means, to the body's fluid filled channels over the body's own pulse upregulates endothelial nitric oxide synthase (eNOS) in portal venous endothelium.

77. The method of medical treatment as recited in claim 76, further comprising:

dosing the patient with inducible nitric oxide synthase (iNOS) inhibitors.

78. The method of medical treatment as recited in claim 1, wherein the medical treatment is for venous stasis; and wherein the step of adding pulses, using the periodic acceleration means, to the body's fluid filled channels over the body's own pulse upregulates endothelial release of nitric oxide, prostacyclin and tissue plasminogen activator (tPA) from venous endothelium and increases venous return, thereby mitigating risk of venous thrombosis.

79. The method of medical treatment as recited in claim 1, wherein the medical treatment is for a patient with one of deep venous thrombosis and a high risk of deep venous thrombosis; and wherein the step of adding pulses, using the periodic acceleration means, to the body's fluid filled channels over the body's own pulse upregulates endothelial release of nitric oxide, prostacycline, and tissue plasminogen activator (tPA) while suppressing tissue plasminogen inhibitor.

80. The method of medical treatment as recited in claim 79, further comprising the step of:

dosing the patient with one of heparin, a heparin-like product, a recombinant tissue plasminogen activator, and a streptokinase in order to provide one of additive and synergistic action.

81. The method of medical treatment as recited in claim 1, wherein the medical treatment is for endothelial dysfunction caused by peripheral arterial occlusive disease; and
wherein the step of adding pulses, using the periodic acceleration means, to the body's fluid filled channels over the body's own pulse restores endothelial function by upregulating basal synthesis of nitric oxide, prostacyclin, and tissue plasminogen activator (tPA) and downregulating basal synthesis of endothelin-1 and tissue plasminogen inhibitor.

82. The method of medical treatment as recited in claim 1, wherein the medical treatment is for dysmenorrhea; and
wherein the step of adding pulses, using the periodic acceleration means, to the body's fluid filled channels over the body's own pulse releases endothelial nitric oxide thereby relieving symptoms of dysmenorrhea.

83. The method of medical treatment as recited in claim 1, wherein the medical treatment is for preeclampsia; and
wherein the step of adding pulses, using the periodic acceleration means, to the body's fluid filled channels over the body's own pulse promotes endothelial release of nitric oxide thereby relieving manifestations of preeclampsia.

84. The method of medical treatment as recited in claim 1, wherein the medical treatment is for preterm cervical dilitation; and
wherein the step of adding pulses, using the periodic acceleration means, to the body's fluid filled channels over the body's own pulse promotes endothelial release of nitric oxide thereby delaying onset of labor.

85. The method of medical treatment as recited in claim 1, wherein the medical treatment is for Alzheimer's disease; and
wherein the step of adding pulses, using the periodic acceleration means, to the body's fluid filled channels over the body's own pulse releases endothelial nitric oxide, increases cerebral blood flow, improves cerebral vessel endothelial function and suppresses formation of Interleukin-6.

86. The method of medical treatment as recited in claim 85, further comprising the step of:
dosing the patient with at least one of inducible nitric oxide synthase (iNOS) and neuronal nitric oxide synthase (nNOS) inhibitors.

87. The method of medical treatment as recited in claim 1, wherein the medical treatment is for Parkinson's disease; and
wherein the step of adding pulses, using the periodic acceleration means, to the body's fluid filled channels over the body's own pulse releases endothelial nitric oxide, increases cerebral blood flow, and improves cerebral vessel endothelial function.

88. The method of medical treatment as recited in claim 87, further comprising the step of:
dosing the patient with at least one of inducible nitric oxide synthase (iNOS) and neuronal nitric oxide synthase (nNOS) inhibitors.

89. The method of medical treatment as recited in claim 1, wherein the medical treatment is for multiple sclerosis; and
wherein the step of adding pulses, using the periodic acceleration means, to the body's fluid filled channels over the body's own pulse releases endothelial nitric oxide promoting vasodilation in areas of the central nervous system.

90. The method of medical treatment as recited in claim 89, further comprising the step of:
dosing the patient with at least one of inducible nitric oxide synthase (iNOS) and neuronal nitric oxide synthase (nNOS) inhibitors.

91. The method of medical treatment as recited in claim 1, wherein the medical treatment is for traumatic brain injury; and
wherein the step of adding pulses, using the periodic acceleration means, to the body's fluid filled channels over the body's own pulse releases endothelial nitric oxide thereby increasing cerebral blood flow to damaged areas of the central nervous system.

92. The method of medical treatment as recited in claim 91, further comprising the step of:
dosing the patient with at least one of inducible nitric oxide synthase (iNOS) and neuronal nitric oxide synthase (nNOS) inhibitors.

93. The method of medical treatment as recited in claim 92, further comprising the step of:
dosing the patient with a narcotic.

94. The method of medical treatment as recited in claim 1, wherein the medical treatment is for pain management; and
wherein the step of adding pulses, using the periodic acceleration means, to the body's fluid filled channels over the body's own pulse promotes endothelial release of nitric oxide.

95. The method of medical treatment as recited in claim 1, wherein the medical treatment is for depressive reactions; and
wherein the step of adding pulses, using the periodic acceleration means, to the body's fluid filled channels over the body's own pulse releases endothelial nitric oxide thereby increasing hippocampal blood flow, and releases endothelial brain-derived neurotrophic factor (BDNF).

96. The method of medical treatment as recited in claim 1, wherein the medical treatment is for sleep deprivation and
wherein the step of adding pulses, using the periodic acceleration means, to the body's fluid filled channels over the body's own pulse releases endothelial nitric oxide thereby promoting NREM sleep.

97. The method of medical treatment as recited in claim 1, wherein the medical treatment is for one of sudden deafness and Meniere's disease; and
wherein the step of adding pulses, using the periodic acceleration means, to the body's fluid filled channels over the body's own pulse upregulates endothelial nitric oxide synthase (eNOS) in the cochlear arterial endothelium.

98. The method of medical treatment as recited in claim 1, wherein the medical treatment is for lymphatic damage; and
wherein the step of adding pulses, using the periodic acceleration means, to the body's fluid filled channels over the body's own pulse releases mediators that promote lymphatic drainage.

99. The method of medical treatment as recited in claim 98, wherein the lymphatic damage is caused by at least one of Milroy's lymphedema, lymphedema precox, lymphedema tarda, lymphangitis, neoplastic lymphatic invasion, irradiation induced narrowing of lymphatic channels, post-traumatic injury to lymphatic channels, chronic heart failure, lymphangiospasm, causalgia, and the surgical resection of lymph nodes and lymph channels.

100. The method of medical treatment as recited in claim 1, wherein the medical treatment is for one of adult respiratory distress syndrome and meconium aspiration syndrome; and
  wherein the step of adding pulses, using the periodic acceleration means, to the body's fluid filled channels over the body's own pulse releases nitric oxide and suppresses endothelin-1 from pulmonary vascular endothelium thereby reducing pulmonary hypertension.

101. The method of medical treatment as recited in claim 1, wherein the medical treatment is for osteoporosis; and
  wherein the step of adding pulses, using the periodic acceleration means, to the body's fluid filled channels over the body's own pulse causes nitric oxide release and upregulation of endothelial nitric oxide synthase (eNOS) which is transmitted to fluid channels of bone, thereby increasing bone mineral density and diminishing bone fracture risk.

102. The method of medical treatment as recited in claim 1, wherein the medical treatment is for bone fractures; and
  wherein the step of adding pulses, using the periodic acceleration means, to the body's fluid filled channels over the body's own pulse releases endothelial nitric oxide from bone blood vessels and osteoblasts in the bone fractures.

103. The method of medical treatment as recited in claim 1, wherein the medical treatment is for rheumatoid and juvenile arthritis; and
  wherein the step of adding pulses, using the periodic acceleration means, to the body's fluid filled channels over the body's own pulse releases nitric oxide and prostacyclin from vascular endothelium thereby suppressing the inflammatory response.

104. The method of medical treatment as recited in claim 103, further comprising the step of:
  dosing the patient with iNOS inhibitors.

105. The method of medical treatment as recited in claim 1, wherein the medical treatment is for osteoarthritis; and
  wherein the step of adding pulses, using the periodic acceleration means, to the body's fluid filled channels over the body's own pulse releases nitric oxide and prostacyclin from vascular endothelium thereby suppressing the inflammatory response.

106. The method of medical treatment as recited in claim 105, further comprising the step of:
  dosing the patient with iNOS inhibitors.

107. The method of medical treatment as recited in claim 1, wherein the medical treatment is for fibromyalgia; and
  wherein the step of adding pulses, using the periodic acceleration means, to the body's fluid filled channels over the body's own pulse releases nitric oxide and prostacyclin from vascular endothelium thereby providing benefits analogous to benefits from exercise.

108. The method of medical treatment as recited in claim 1, wherein the medical treatment is for wounds; and
  wherein the step of adding pulses, using the periodic acceleration means, to the body's fluid filled channels over the body's own pulse increases endothelial release of nitric oxide thereby facilitating wound healing through increased blood flow and laying down of reparative wound collagen.

109. The method of medical treatment as recited in claim 108, further comprising the step of:
  providing one of light and laser therapy to provide one of additive and synergistic actions in the promotion of wound healing.

110. The method of medical treatment as recited in claim 1, wherein the medical treatment is for bed sores; and
  wherein the step of adding pulses, using the periodic acceleration means, to the body's fluid filled channels over the body's own pulse increases endothelial release of nitric oxide thereby facilitating healing.

111. The method of medical treatment as recited in claim 1, wherein the medical treatment is for anal fissure; and
  wherein the step of adding pulses, using the periodic acceleration means, to the body's fluid filled channels over the body's own pulse stimulates endothelial release of nitric oxide thereby providing pain relief and facilitated healing.

112. The method of medical treatment as recited in claim 1, wherein the medical treatment is for tendon damage; and
  wherein the step of adding pulses, using the periodic acceleration means, to the body's fluid filled channels over the body's own pulse causes endothelial release of nitric oxide thereby facilitating tendon healing.

113. The method of medical treatment as recited in claim 1, wherein the medical treatment is for acute gastric injury; and
  wherein the step of adding pulses, using the periodic acceleration means, to the body's fluid filled channels over the body's own pulse releases nitric oxide from endothelium.

114. The method of medical treatment as recited in claim 1, wherein the medical treatment is for HIV-1 infection; and
  wherein the step of adding pulses, using the periodic acceleration means, to the body's fluid filled channels over the body's own pulse releases endothelial nitric oxide.

115. The method of medical treatment as recited in claim 1, wherein the medical treatment is for erectile dysfunction; and
  wherein the step of adding pulses, using the periodic acceleration means, to the body's fluid filled channels over the body's own pulse upregulates endothelial nitric oxide synthase (eNOS) and prostacyclin synthesis in endothelium.

116. The method of medical treatment as recited in claim 1, wherein the medical treatment is for cancer; and
  wherein the step of adding pulses, using the periodic acceleration means, to the body's fluid filled channels over the body's own pulse increases endothelial release of nitric oxide thereby inhibiting growth of tumors.

117. The method of medical treatment as recited in claim 1, wherein the medical treatment is for prostate cancer with an overexpression of endothelin-1; and
  wherein the step of adding pulses, using the periodic acceleration means, to the body's fluid filled channels over the body's own pulse increases endothelial release of nitric oxide thereby inhibiting growth of the prostate cancer.

118. The method of medical treatment as recited in claim 114, further comprising the step of:
  dosing the patient with cisplatin.

119. The method of medical treatment as recited in claim 1, wherein the medical treatment is for a patient with hepatic veno-occlusive disease who is undergoing hematopoetic stem cell transplantation; and
  wherein the step of adding pulses, using the periodic acceleration means, to the body's fluid filled channels over the body's own pulse upregulates endothelial storage and release of tissue plasmiogen activator and suppresses tissue plasminogen inhibitor.

120. The method of medical treatment as recited in claim 1, wherein the medical treatment is for the improvement of memory and cognitive function.

121. A method of medical treatment for a patient with a body, comprising the steps of:
providing a pulse means for externally and non-invasively pulsing one of the body and at least one part thereof; and
treating a disease, condition, or injury of the patient that is treatable by at least one endothelial released mediator by adding pulses, using the pulse means, to the body's fluid filled channels over the body's own pulse, said added pulses not being synchronized with the body's own pulse, thereby stimulating endothelial release of beneficial mediators and suppressing non-beneficial mediators;
wherein the periodic acceleration means comprises a reciprocating movement platform which periodically accelerates the one of the body and at least one part thereof in a headwards-footwards direction at a frequency between about 1 Hz and about 6 Hz.

122. The method of medical treatment as recited in claim 121, wherein the step of providing a pulse means for externally and non-invasively pulsing one of the body and at least one part thereof comprises the step of:
providing a compression means for providing external intermittent compression of at least one of the legs, thighs, and buttocks.

123. The method of medical treatment as recited in claim 122, further comprising the step of:
providing at least one of air and liquid filled bladders, the at least one bladder attached to reservoirs and pumps, and placed around at least one of legs, thighs, and buttocks.

124. The method of medical treatment as recited in claim 122, further comprising the step of:
exercising, by the patient, on a treadmill within a lower body negative pressure chamber in order to maintain bone, neuromuscular and cardiovascular fitness on long space flights in microgravitational fields.

125. A method of medical diagnosis for a subject with a body, comprising the steps of:
providing a periodic acceleration means for periodically accelerating one of the body and at least one part thereof;
treating a disease, condition, or injury of the patient that is treatable by at least one endothelial released mediator by adding pulses, using the periodic acceleration means, to the body's fluid filled channels over the body's own pulse to thereby add pulses over the body's own pulse to the body's fluid filled channels; and
testing a physiological response of the subject either during or immediately after the step of adding pulses, using the periodic acceleration means, to the body's fluid filled channels over the body's own pulse;
wherein the periodic acceleration means comprises a reciprocating movement platform which periodically accelerates the one of the body and at least one part thereof in a headwards-footwards direction at a frequency between about 1 Hz and about 6 Hz.

126. The method of medical diagnosis as recited claim 125, wherein the periodic acceleration means controls the frequency and intensity of said pulses.

127. The method of medical diagnosis as recited in claim 125, wherein the testing step comprises the step of:
analyzing a dicrotic notch present on a diastolic limb of an arterial pulse;
wherein an amount of downward descent of the dicrotic notch is a function of nitric oxide released and absent or diminished descent of dicrotic notch relative to response of normally functioning endothelium is caused by endothelial dysfunction.

128. The method of medical diagnosis as recited in claim 127, wherein the testing step comprises:
computing a b/a ratio, wherein the b/a ratio is the height of the dicrotic notch upward inflection point from its location on arterial pulse to the end-diastolic level (b) divided by total pulse amplitude height (a).

129. The method of medical diagnosis as recited in claim 127, wherein the dicrotic notch is determined using non-invasive sensors, wherein the non-invasive sensors are placed on at least one of thumbs or fingers, toes, neck and skin or over at least one of radial, brachial, carotid, subclavian, and femoral arteries.

130. The method of medical diagnosis as recited in claim 129, wherein the non-invasive sensors comprise a digital inductive plethysmograph.

131. The method of medical diagnosis as recited in claim 129, wherein the non-invasive sensors comprise at least one of oscillometric plethysmographs, piezoelectric sensors, mercury in rubber or silastic strain gauges, photoelectric plethysmographs, pulse oximeters, impedance plethysmographs, capacitance condenser microphones, and electronic pneumoplethysmographs.

132. The method of medical diagnosis as recited in claim 125, wherein the testing step comprises:
computing dose response curves by plotting frequency, amplitude of added pulses, and peak acceleration of the externally added pulses against a b/a ratio, wherein the b/a ratio is the height of a dicrotic notch upward inflection point from its location on arterial pulse to the end-diastolic level (b) divided by total pulse amplitude height (a); and
comparing the computed dose response curves to control dose response curves.

133. The method of medical diagnosis as recited in claim 132, wherein the control dose response curves comprise one of dose response curves of the subject after applying a nitric oxide donor drug that relaxes vascular smooth muscle independent of endothelial participation and dose response curves of a normal population.

134. The method of medical diagnosis as recited in claim 125, further comprising the steps of:
displaying on a display the arterial pulse of the subject during external addition of pulses; and
removing device driven, externally added pulses from the display of the arterial pulse.

135. The method of medical diagnosis as recited in claim 134, wherein the step of removing external pulses from the display comprises the step of:
using triggered electrocardiographic R-wave ensemble-averaging in order to remove device driven, externally added pulses from the display of the arterial pulse and to display an averaged vascular pulse.

136. The method of medical diagnosis as recited in claim 134, wherein the step of removing external pulses from the display comprises the steps of:
triggered ensemble-averaging of input from at least one of linear displacement, velocity, or acceleration sensors mounted either to the means for externally and non-invasively adding external pulses into the body's fluid filled channels or the subject to obtain an averaged externally added pulse output; and subtracting the averaged externally added pulses output from an averaged vascular pulse output while accounting for differences of phase and gain characteristics between the two outputs.

137. The method of medical diagnosis as recited in claim 134, further comprising the step of:

displaying at least one of an averaged vascular pulse, an averaged mathematical first derivative from the averaged vascular pulse, and an averaged mathematical second derivative from the averaged vascular pulse, along with an averaged electrocardiographic waveform for timing purposes.

138. The method of medical diagnosis as recited in claim 125, wherein the testing step comprises the step of:

analyzing an Augmentation Index of the subject's arterial pulse, wherein the Augmentation Index is a ratio of the amplitude of pressure wave between its initial systolic shoulder to the peak divided by the pulse amplitude;

wherein an increase in a baseline of the Augmentation Index relative to a response of normally functioning endothelium is caused by endothelial dysfunction.

139. The method of medical diagnosis as recited in claim 125, wherein the testing step comprises the step of:

analyzing arterial pulse wave velocity, wherein arterial pulse wave velocity is computed by dividing the distance between two remote arterial sites by difference in time of onset of two remote arterial waveforms;

wherein an increase in arterial pulse wave velocity relative to a response of normally functioning endothelium is caused by endothelial dysfunction.

140. The method of medical diagnosis as recited in claim 125, wherein the testing step comprises the step of:

analyzing central venous pressure;

wherein a decrease in central venous pressure is caused by normal endothelial function and little or no change occurs in the presence of endothelial dysfunction.

141. The method of medical diagnosis as recited in claim 140, wherein a means for measuring the central venous pressure is a neck inductive plethysmograph.

142. The method of medical diagnosis as recited in claim 125, wherein the testing step comprises the step of:

analyzing E wave deceleration time, wherein E wave deceleration time is computed from the mathematical derivative of the left ventricular volume curve;

wherein, because of endothelial dysfunction of the heart corresponding to diastolic dysfunction, the E wave deceleration time during the addition of external pulses is substantially unchanged relative to a response of normally functioning endothelium.

143. The method of medical diagnosis as recited in claim 142, wherein a means for measuring the left ventricular volume curve is a thoracic inductive inductive plethysmograph (thoracocardiograph).

144. The method of medical diagnosis as recited in claim 125, wherein the testing step comprises the step of:

analyzing blood flow of the subject;

wherein, during the addition of external pulses, a lesser increase in blood flow relative to a response of normally functioning endothelium is caused by endothelial dysfunction.

145. The method of medical diagnosis as recited in claim 144, wherein a means for measuring the blood flow comprises one of venous occlusion plethysmography with a limb inductive plethysmograph, mercury on rubber or silastic strain gauges, and doppler ultrasound imaging.

146. The method of medical diagnosis as recited in claim 125, wherein the testing step comprises the step of:

utilizing biochemical markers to test the response of the subject.

147. The method of medical diagnosis as recited in claim 146, wherein the biochemical marker comprises a marker of one of urinary serum, blood serum, plasma nitrite/nitrate, or nitric oxide.

148. The method of medical diagnosis as recited in claim 146, wherein, during the addition of external pulses, the extent of the change, if any, in levels of the biochemical object of the biochemical marker is indicative of endothelial function.

149. The method of medical diagnosis as recited in claim 146, wherein the biochemical marker comprises at least one of L-citrulline, prostacyclin, and tissue plasminogen activator (t-PA), and wherein, during the addition of external pulses, the at least one of L-citrulline, prostacyclin, and tissue plasminogen activator (t-PA) remains substantially unchanged relative to a response of normally functioning endothelium because of endothelial dysfunction and rises relative to a response of normally functioning endothelium because of normal endothelial function.

150. The method of medical diagnosis as recited in claim 125, wherein the testing step comprises the step of:

utilizing a blood coagulation test;

wherein, during the addition of external pulses, a decrease in fibrinogen or increase in fibrinogen degradation products is a response of normally functioning endothelium whereas little or no change in fibrinogen or fibrinogen degradation products occurs in the presence of endothelial dysfunction.

151. The method of medical diagnosis as recited in claim 125, wherein at least one of the following conditions is being tested for: atherosclerosis, hypertriglyeridemia, systemic hypertension, hypercholesterolemia, insulin resistance syndrome, arterial smooth muscle dysfunction, microvascular cerebrovascular disorders, and normal pressure glaucoma.

152. The method of medical diagnosis as recited in claim 125, wherein the testing step comprises the step of:

analyzing baroceptor sensitivity as a plot of RR intervals of an electrocardiogram against a rate of arterial distension from a thumb or finger inductive plethysmograph.

153. The method of medical diagnosis as recited in claim 152, wherein at least one of the following conditions is being screened for: atherosclerosis, diabetes, and chronic heart failure.

154. The method of medical diagnosis as recited in claim 125, wherein the periodic acceleration means comprises running or jumping by the subject.

155. The method of medical diagnosis as recited in claim 125, wherein the subject is a baby and wherein the periodic acceleration means comprises a carriage which is pushed back and forth by a caregiver.

156. The method of medical diagnosis as recited in claim 125, wherein the periodic acceleration means comprises running or jumping by the subject.

* * * * *